(12) United States Patent
Cochran et al.

(10) Patent No.: US 10,370,653 B2
(45) Date of Patent: Aug. 6, 2019

(54) MICRO-SCREENING APPARATUS, PROCESS, AND PRODUCTS

(71) Applicant: The Board of Trustees of the Leland Stanford Junior University, Palo Alto, CA (US)

(72) Inventors: Jennifer R. Cochran, Stanford, CA (US); Thomas M. Baer, Mountain View, CA (US); Bob Chen, Stanford, CA (US); Spencer Caleb Alford, Mountain View, CA (US); Arvind Kannan, Stanford, CA (US); Sungwon Lim, Stanford, CA (US); Ivan Dimov, Union City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 155 days.

(21) Appl. No.: 15/050,142

(22) Filed: Feb. 22, 2016

(65) Prior Publication Data

US 2016/0244749 A1    Aug. 25, 2016

Related U.S. Application Data

(60) Provisional application No. 62/119,251, filed on Feb. 22, 2015, provisional application No. 62/120,803, filed on Feb. 25, 2015, provisional application No. 62/250,478, filed on Nov. 3, 2015, provisional application No. 62/281,545, filed on Jan. 21, 2016.

(51) Int. Cl.
| | |
|---|---|
| *C12N 15/10* | (2006.01) |
| *C40B 30/06* | (2006.01) |
| *C40B 30/08* | (2006.01) |
| *G01N 33/50* | (2006.01) |
| *G01N 33/53* | (2006.01) |
| *G01N 33/543* | (2006.01) |
| *C40B 60/12* | (2006.01) |

(52) U.S. Cl.
CPC .......... *C12N 15/1079* (2013.01); *C40B 30/06* (2013.01); *C40B 30/08* (2013.01); *G01N 33/502* (2013.01); *G01N 33/5304* (2013.01); *G01N 33/54366* (2013.01); *G01N 33/54386* (2013.01); *B01J 2219/00286* (2013.01); *B01J 2219/00317* (2013.01); *C40B 60/12* (2013.01)

(58) Field of Classification Search
CPC ............................ C12N 15/1079; C40B 30/06
USPC ....................................................... 506/10
See application file for complete search history.

(56) References Cited

U.S. PATENT DOCUMENTS

| | | |
|---|---|---|
| 4,115,535 A | 9/1978 | Giaever |
| 4,731,337 A | 3/1988 | Luotola et al. |
| 4,758,523 A | 7/1988 | Harjunmaa |
| 4,777,145 A | 10/1988 | Luotola et al. |
| 5,351,332 A | 9/1994 | Cook |
| 5,538,848 A | 7/1996 | Livak et al. |
| 5,639,606 A | 6/1997 | Willey |
| 5,643,765 A | 7/1997 | Willey |
| 5,846,717 A | 12/1998 | Brow et al. |
| 5,876,978 A | 3/1999 | Willey et al. |
| 5,962,223 A | 10/1999 | Whiteley et al. |
| 5,985,557 A | 11/1999 | Prudent et al. |
| 5,994,069 A | 11/1999 | Hall et al. |
| 6,001,567 A | 12/1999 | Brow et al. |
| 6,023,540 A | 2/2000 | Walt et al. |
| 6,027,873 A | 2/2000 | Schellenberger et al. |
| 6,090,543 A | 7/2000 | Prudent et al. |
| 6,133,436 A | 10/2000 | Koster et al. |
| 6,716,629 B2 | 4/2004 | Hess et al. |
| 6,794,127 B1 | 9/2004 | Lafferty et al. |
| 6,838,056 B2 | 1/2005 | Foster |
| 6,866,824 B2 | 3/2005 | Lafferty et al. |
| 6,964,872 B2 | 11/2005 | Sakurai et al. |
| 7,122,384 B2 | 10/2006 | Prober et al. |
| 7,264,972 B2 | 9/2007 | Foster |
| 7,572,640 B2 | 8/2009 | Goix et al. |
| 8,460,878 B2 | 6/2013 | Rissin et al. |
| 8,460,879 B2 | 6/2013 | Rissin et al. |
| 8,492,098 B2 | 7/2013 | Rissin et al. |
| 8,632,768 B2 | 1/2014 | Ildstad et al. |
| 9,314,764 B2 | 4/2016 | Hess et al. |
| 9,395,359 B2 | 7/2016 | Walt et al. |
| 9,452,184 B2 | 9/2016 | Ildstad et al. |
| 9,523,076 B2 | 12/2016 | Schoenbrunn et al. |
| 9,643,180 B2 | 5/2017 | Abrams et al. |
| 9,657,290 B2 | 5/2017 | Dimov et al. |
| 9,658,219 B2 | 5/2017 | Verschuren et al. |
| 9,746,457 B2 | 8/2017 | Hare et al. |

(Continued)

FOREIGN PATENT DOCUMENTS

| | | |
|---|---|---|
| CN | 1030139 A | 1/1989 |
| CN | 1032399 A | 4/1989 |

(Continued)

OTHER PUBLICATIONS

Heim et al.(Nature, Feb. 23, 1995, vol. 373, pp. 663-664). (Year: 1995).*

(Continued)

*Primary Examiner* — Karla A Dines

(74) *Attorney, Agent, or Firm* — McDonnell Boehnen Hulbert & Berghoff LLP

(57) ABSTRACT

Microcavity arrays and methods for quantitative biochemical and biophysical analysis of populations of biological variants. Examples include high-throughput analysis of cells and protein products use a range of fluorescent assays, including binding-affinity measurement and time-resolved enzyme assays. Laser-based extraction of microcavity contents.

19 Claims, 41 Drawing Sheets

Specification includes a Sequence Listing.

(56) References Cited

U.S. PATENT DOCUMENTS

| | | | |
|---|---|---|---|
| 2002/0045270 | A1 | 4/2002 | Schurenberg et al. |
| 2002/0094533 | A1 | 7/2002 | Hess |
| 2002/0155439 | A1 | 10/2002 | Rodriguez et al. |
| 2003/0096220 | A1 | 5/2003 | Lafferty et al. |
| 2005/0009101 | A1 | 1/2005 | Blackburn |
| 2005/0196376 | A1* | 9/2005 | Loomis ............. A61K 31/785 424/78.27 |
| 2006/0078998 | A1 | 4/2006 | Puskas |
| 2007/0259448 | A1 | 11/2007 | Rissin et al. |
| 2008/0032401 | A1 | 2/2008 | Edinger et al. |
| 2008/0280285 | A1 | 11/2008 | Chen et al. |
| 2010/0300559 | A1 | 12/2010 | Schultz et al. |
| 2011/0298883 | A1 | 12/2011 | Ohyama |
| 2012/0122149 | A1 | 5/2012 | Kocagoz |
| 2014/0011690 | A1 | 1/2014 | Dimov et al. |
| 2014/0273207 | A1 | 9/2014 | Chan et al. |
| 2014/0295421 | A1* | 10/2014 | Link ................. B01F 5/0646 435/6.11 |
| 2014/0345364 | A1 | 11/2014 | Lin et al. |
| 2015/0011406 | A1* | 1/2015 | Rich .................. G01N 33/582 506/9 |
| 2016/0040123 | A1 | 2/2016 | Kanemura et al. |
| 2016/0245805 | A1 | 8/2016 | Baer et al. |
| 2016/0281061 | A1 | 9/2016 | Beachley et al. |
| 2016/0303564 | A1 | 10/2016 | Gilbert et al. |
| 2017/0000825 | A1 | 1/2017 | Ildstad et al. |
| 2017/0246277 | A1 | 8/2017 | Schneck et al. |
| 2017/0292915 | A1 | 10/2017 | Dimov et al. |

FOREIGN PATENT DOCUMENTS

| | | |
|---|---|---|
| CN | 1360638 A | 7/2002 |
| CN | 1491359 A | 4/2004 |
| CN | 102224260 A | 10/2011 |
| EP | 2163640 | 7/2011 |
| EP | 2306191 B1 | 12/2012 |
| EP | 2606120 B1 | 10/2015 |
| EP | 3037522 A1 | 6/2016 |
| JP | H0750113 B2 | 5/1995 |
| JP | 2004510996 A | 4/2004 |
| JP | 2010512534 A | 4/2010 |
| WO | WO-1986004684 | 8/1986 |
| WO | WO-1987007386 | 12/1987 |
| WO | WO-2000063404 | 10/2000 |
| WO | 2001038583 | 5/2001 |
| WO | 200231203 | 4/2002 |
| WO | WO-2004004637 A2 | 1/2004 |
| WO | WO-2004044232 A1 | 5/2004 |
| WO | 2006110098 | 10/2006 |
| WO | 2007035586 | 3/2007 |
| WO | 2007098148 | 8/2007 |
| WO | 2012007537 | 1/2012 |
| WO | WO-2014008056 A2 | 1/2014 |
| WO | WO-2016133907 A1 | 8/2016 |
| WO | WO-2016134370 A1 | 8/2016 |
| WO | WO-2018053485 A1 | 3/2018 |
| WO | WO-2018089953 A1 | 5/2018 |

OTHER PUBLICATIONS

Huft et al., "Three-dimensional large-scale microfluidic integration by laser ablation of interlayer connections", Lab Chip, 10:2358-2365 (2010).

Andersson, et al., "Micromachined flow-through filter-chamber for chemical reactions on beads", Sensors and Actuators, 67:203-208 (2000).

Lim, et al., "Bead-based microfluidic immunoassays: The next generation", Biosensors and Bioelectronics, 22:1197-1204 (2007).

Miraglia, et al., "Homogeneous Cell- and Bead-Based Assays for High Throughput Screening Using Fluorometric Microvolume Assay Technology", The Journal of Biomolecular Screening, 4:193-204 (1999).

Murakami, et al., "On-chip micro-flow polystyrene bead-based immunoassay for quantitative detection of tacrolimus (FK506)", Analytical Biochemistry, 334:111-116 (2004).

Thompson, et al., "Polymeric microbead arrays for microfluidic applications", J. Micromech. Microeng. 20:1-8 (2010).

Zaytseva, et al., "Development of a microfluidic biosensor module for pathogen detection", Lab Chip, 5:805-811 (2005).

Chalfie, et al., "Green Fluorescent Protein as a Marker for Gene Expression", Science, 263:802-805 (1994).

Galajda, et al., "A Wall of Funnels Concentrates Swimming Bacteria", Journal of Bacteriology, 189:8704-8707 (2007).

Groisman, et al., "A microfluidic chemostat for experiments with bacterial and yeast cells", Nature Methods, 2:685-689 (2005).

Xia, et al.,, "Combined microfluidic-micromagneitc separation of living cells in continuous flow", Biomed Microdevices 8:299-308 (2006).

Bao, et al., "A microfluidic deveice for physical trapping and electrical lysis of bacterial cells", Applied Physics Letters, 92:1-3 (2008).

Mandal, et al., "Encapsulation of Magnetic and Fluorescent Nanoparticles in Emulsion Droplets", Langmuir, 21:4175-4179 (2005).

Laurell, et al., "Chip integrated strategies for acoustic separation and manipulation of cells and particles", Chem. Soc. Rev., 36:492-506 (2007).

Steinberg, et al., "Early Keratinocyte Differentiation on Micropillar Interfaces", Nano Letters, 7:287-294 (2007).

Keilberg, V., Tech Note No. 14: Cryopreservation of Mammalian Cells Protocols, Thermo Scientific, (2010).

Wolf, et al., "Quantitative Analysis of Digital Microscope Images", Methods Cell Biol., 114:337-67 (2007).

Huse, et al., "Application of a Filamentous Phage pVlll Fusion Protein System Suitable for Efficient Production, Screening and Mutagenesis of F(ab) Antibody Fragments," J. Immunol 149:3914-3920 (1992).

Kariolis, M. S. et al., "An engineered Axl 'decoy receptor' effectively silences the Gas6/Axl signaling axis", Nat. Chem. Biol. 10:977-83 (2014).

Van Deventer, et al., "Yeast Surface Display for Antibody Isolation: Library Construction, Library Screening and Affinity Maturation", Monoclonal Antibodies: Methods and Protocols, Methods in Molecular Biology, Chapter 10, vol. 1131:151-181 (2014).

Chao, et al., "Isolating and engineering human antibodies using yeast surface display", Nat. Protoc. 1:755-68 (2006).

Zinchenko, et al., "One in a Million: Flow Cytometric Sorting of Single Cell-Lysate Assays in Monodisperse Picolitre Double-Emulsion Droplets for Directed Evolution", Anal. Chem. 86:2526-33 (2014).

Fischlechner, M., et al. "Evolution of enzyme catalysts caged in biomimetic gel-shell beads", Nat. Chem., 6:791-796 (2014).

Ai, et al., "Engineering and characterizing monomeric fluorescent proteins for live-cell imaging applications", Nat. Protoc., 9:910-28 (2014).

Shaner, et al., "Improved monomeric red, orange and yellow fluorescent proteins derived from *Discosoma* sp. red fluorescent protein", Nat. Biotechnol. 22:1567-72 (2014).

Alford, et al., "Dimerization-Dependent Green and Yellow Fluorescent Proteins", ACS Synth. Biol., 1:569-75 (2012).

Alford, et al., "A Fluorogenic Red Fluorescent Protein Heterodimer", Chem. Biol., 19:353-60 (2012).

Brune, et al., "Direct, Real-Time Measurement of Rapid Inorganic Phosphate Release Using a Novel Fluorescent Probe and Its Application to Actomyosin Subfragment 1 ATPase", Biochemistry, 33:8262-71 (1994).

O'Brien, et al., "Functional Interrelationships in the Alkaline Phosphatase Supertamily: Phosphodiesterase Activity of *Escherichia coli* Alkaline Phosphatase", Biochemistry, 40:5691-5699 (2001).

Alberstein, et al., "Removing allosteric feedback inhibition of tomato 4-coumarate:CoA ligase by directed evolution", Plant J. 69:57-69 (2012).

Yang, J., et al., "Rational Engineering of Enzyme Allosteric Regulation through Sequence Evolution Analysis", PLoS Comput. Biol., 8:e1002612 (2012).

(56) References Cited

OTHER PUBLICATIONS

Hu et al., "Engineering of a fungal β-galactosidase to remove product inhibition by galactose", Appl. Microbiol. Biotechnol. 87:1773-82 (2010).

Andrews, et al., "Probing the Origins of Catalytic Discrimination between Phosphate and Sulfate Monoester Hydrolysis: Comparative Analysis of Alkaline Phosphatase and Protein Tyrosine Phosphatases", Biochemistry, 53:6811-6819 (2014).

Anderson et al., "Memory CD4+ T cells do not induce graft-versus-host disease," The Journal of Clinical Investigation 112(1):101-108, 2003.

Chen et al., "High-throughput analysis and protein engineering using microcapillary arrays," Nature Chemical Biology 12:76-81, 2016. Published Dec. 7, 2015. (9 pages).

De Freitas et al. Pulsatile dynamic stiffness of cartilage-like materials and use of agarose gels to validate mechanical methods and models. 78B(2):347-357 (2006).

EP13813011.7 Extended European Search Report dated Jun. 24, 2016.

Fitzgerald et al. Exploiting Highly Ordered Subnanoliter Volume Microcapillaries as Microtools for the Analysis of Antibody Producing Cells. Anal Chem 87:997-1003 (2015). Published Dec. 5, 2014.

PCT/US2013/047792 International Search Report dated Jan. 16, 2014.

PCT/US2016/018954 International Search Report dated Jun. 24, 2016.

PCT/US2017/052218 International Search Report dated Dec. 5, 2017.

PCT/US2017/061414 International Search Report dated Mar. 8, 2018.

EP16753225.8 Extended European Search Report dated Jun. 21, 2018.

U.S. Appl. No. 13/791,967 Notice of Allowance dated Feb. 13, 2017.

U.S. Appl. No. 13/791,967 Notice of Allowance dated Jan. 10, 2017.

U.S. Appl. No. 13/791,967 Office Action dated Dec. 9, 2015.

U.S. Appl. No. 13/791,967 Office Action dated May 24, 2016.

U.S. Appl. No. 15/050,130 Office Action dated Jun. 11, 2018.

U.S. Appl. No. 15/050,130 Office Action dated Nov. 1, 2017.

\* cited by examiner

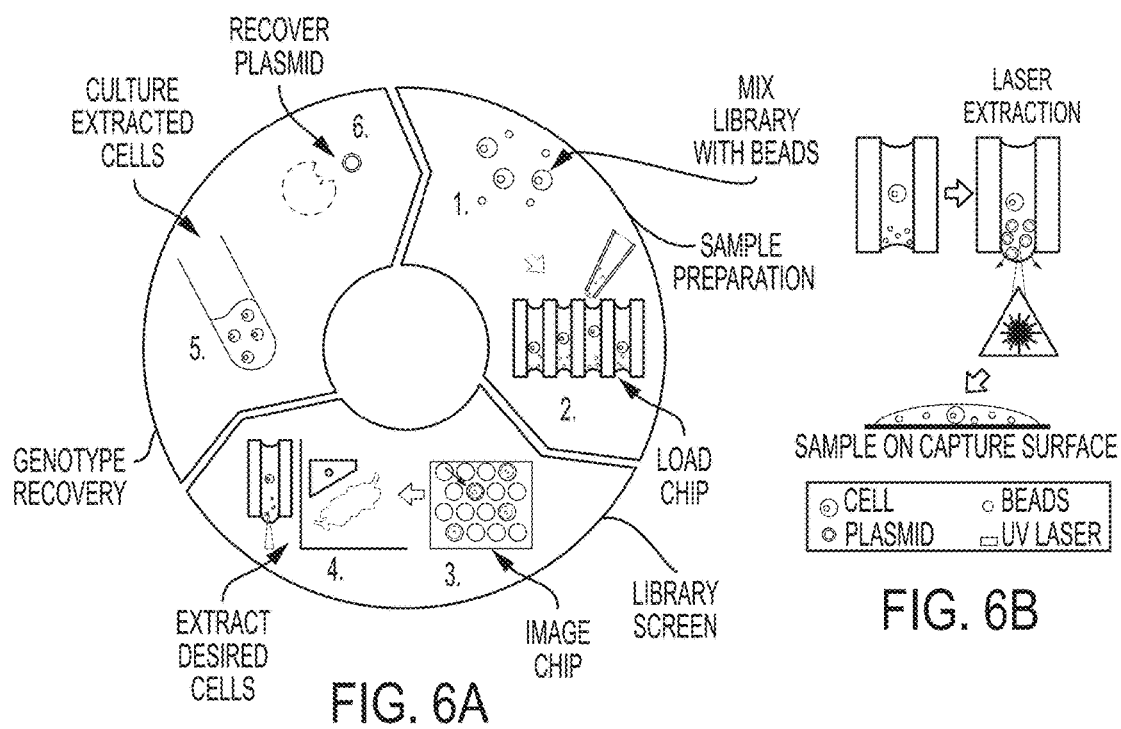
FIG. 6A
FIG. 6B
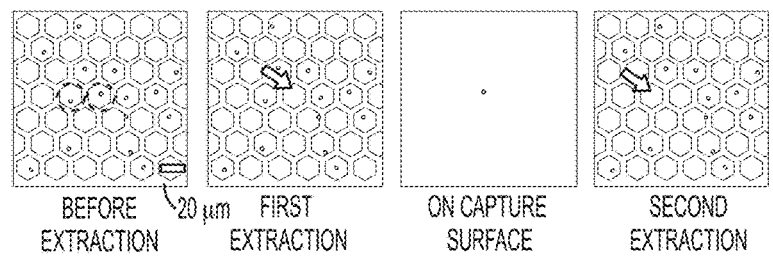
FIG. 6C
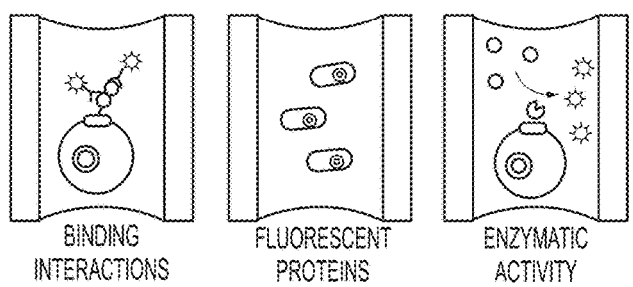
FIG. 6D

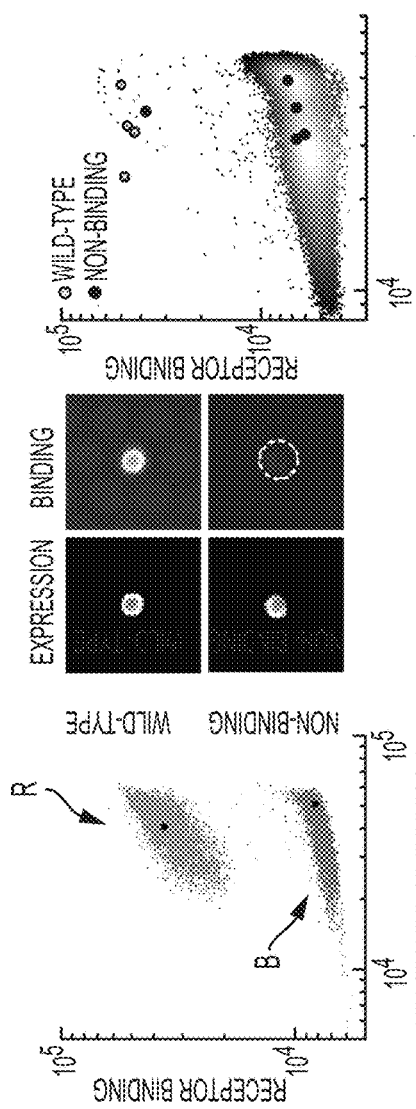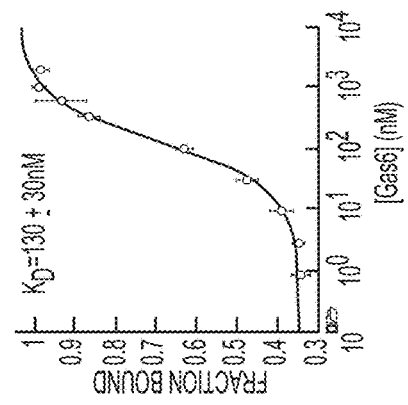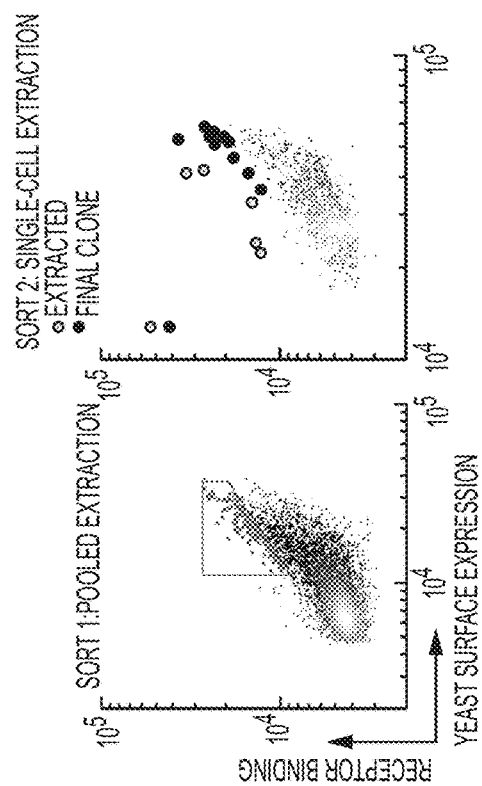

SEQ ID NO:1   1  ------VIKEFMRFKVRLEGSMNGHEFEIEGEGEGRPYEGTQTAKLKVTKGGPLPFAWD
SEQ ID NO:2   1  MVSKSEEVIKEFMRFKVRLEGSMNGHEFEIEGEGEGRPYEGTQTAKLKVTKGGPLPFAWD

ILSPQT[M]YGSKAYVKHPADVPDYMKLSFPEGFKWERVMHFEDGGLVTVTQDTSLQDGTLI
ILSPQIMYGSKAYVKHPADVPDYMKLSFPEGFKWERVMHFEDGGLVTVTQDTSLQDGTLI

YKVKMRGTNFPPDGPVMQRKTLGWDYSTERLYPENGVLKGELLGRLKLKDGGL[Y]LVEFKT
YKVKMRGTNFPPDGPVMQKKTLGWDYATERLYPEDGVLKGELLGRLKLKDGGLNLVEFKT

IYMAKKPVQLPGYYFVDTKLD[?]ITSHNEDYTIVEQYERSEGRHHLGMDELYK
IYMAKKPVQLPGYYFVDTKLGITSHNEDYTIVEQYERSEGRHHLGMDELYK

Figure 17

SEQ ID NO:1 = ddOFP
SEQ ID NO:2 = ddRFP

MICRO-SCREENING APPARATUS, PROCESS, AND PRODUCTS

RELATED APPLICATIONS

This application claims the benefit of U.S. Provisional Application Ser. No. 62/119,251, filed Feb. 22, 2015, U.S. Provisional Application Ser. No. 62/120,803, filed Feb. 25, 2015, U.S. Provisional Application Ser. No. 62/250,478, filed Nov. 11, 2015 and U.S. Provisional Application Ser. No. 62/281,545, filed Jan. 21, 2016, each of which is incorporated by reference herein in its entirety.

BACKGROUND

Field

The disclosure is directed to the determination of compounds of interest using microarrays.

Background

High-throughput measurements have begun to provide insight into the intrinsic complexities and dense interconnectivities of biological systems. As examples, whole-genome sequencing has yielded a wealth of information on crucial genes and mutations underlying disease pathophysiology, DNA microarrays have allowed transcription patterns of various cancers to be dissected, and large-scale proteomics methods have facilitated the study of signaling networks in cells responding to various growth factors. However, the ability to rapidly interrogate the sequence-structure-activity relationship of millions of protein variants, with functional read-outs that span a range of biophysical and biochemical measurements, remains a critical unmet need in high-throughput biology. Here, we describe a user-friendly, cost-effective technology we developed to address this need and showcase its capabilities and breadth through novel discovery applications on three distinct protein classes: antibody therapeutics, fluorescent protein biosensors, and enzymes.

Protein engineers rely heavily on directed evolution, a powerful combinatorial screening method which uses selective pressure to evolve proteins with improved properties. Using this approach, libraries are screened to identify proteins with desirable characteristics, such as high affinity binding to a target of interest, stability, expression, or enzymatic activity. Maintaining a genotype-to-phenotype linkage is a fundamental requirement for any directed evolution effort; a protein variant must remain associated with its corresponding DNA sequence to be identified following a screen. This requirement is most easily achieved in assays used to screen for protein binding partners. As examples, genetic fusion of protein variants to microbial cell surface or phage components or translation machinery has allowed rapid identification of target binders from large protein libraries ($10^7$-$10^{14}$ variants) using fluorescence-activated cell sorting (FACS) or panning methods.

Protein analysis methods that employ spatial segregation, such as testing individual enzyme variants in microtiter plates, have expanded protein engineering applications beyond binding interactions, but are generally limited in throughput to $10^3$-$10^5$ variants in a typical screen. These relatively small library sizes are restrictive due to the vast theoretical diversity of amino acid search space for a typical protein. Robotic handling systems for assaying protein function in microtiter plates have eased labor, but are still relatively low-throughput (e.g. 100,000 assays per day), and require cost-prohibitive quantities of materials and reagents. Recently, oil-water emulsion droplets created in bulk or combined with microfluidics chips have achieved success in high-throughput enzyme engineering applications, however, this technology can be challenging to implement and does not easily allow temporal measurements of kinetic parameters in real-time during an experiment.

SUMMARY

In one aspect, the disclosure is directed to a method for screening a library of cells having a plurality of genotypes for a cell having a phenotype of interest for producing a molecule of interest. The method includes loading a microcavity array with the library of cells; incubating the array under conditions that allow for production of the molecule of interest; imaging the array to identify a cavity comprising cells having the phenotype of interest; and extracting the contents of the cavity comprising cells having the phenotype of interest by directing electromagnetic radiation from a pulsed diode laser at a radiation absorbing material associated with the cavity.

In various embodiments of the methods of the disclosure, the directing of the electromagnetic radiation includes applying the electromagnetic radiation to the radiation absorbing material to avoid heating a sample liquid in the cavity that is not in contact with the material. The cells may be expanded in the array and may be selected from mammalian cells, yeast cells, and bacterial cells.

The method of the disclosure also may also include culturing the extracted contents of the cavities to produce a second-generation library of cells. The extracted contents may be expanded an loaded on the array. The method may include (1) extracting DNA from the cells comprising a gene for the phenotype of interest, (2) amplifying the DNA under conditions to introduce mutations in the gene; (3) creating a second generation library of cells comprising the amplified DNA, and (4) repeating method steps for loading, culturing and extracting cells from the array.

In various aspects of the method of the disclosure, phenotype of interest may be cell producing a binding agent, such as an antibody, an antibody fragment, a ligand, a small molecule, or a receptor. The molecule of interest may be a fluorescent protein that has at least one of an emission intensity of interest and an emission spectra of interest, and the scanning may include identifying cavities emitting the at least one of the emission intensity of interest and the emission spectra of interest. The phenotype of interest may be a cell producing a protein having an enzymatic activity, a protein having a lack of inhibition of enzyme activity, and/or a protein having activity in the presence of an inhibitor for the enzyme.

In another aspect, the disclosure is directed to a method for engineering a property of interest in a fluorescent protein. The property of interest may be one or more of an emission spectra, an emission intensity, a stokes shift, and an absorption spectra. The method includes creating a library of cells producing a mutant form of a fluorescent protein, and screening the library for cells producing the mutant form having the property of interest. The screening method includes loading a microcavity array with the library of cells; incubating the array under conditions that allow for production of the mutant form; imaging the array to identify a cavity comprising cells producing the mutant form; and extracting the contents of the cavity comprising cells producing the mutant form.

Still further, the disclosure is directed to a method for measuring enzyme kinetics for a member of a protein enzyme library produced by a library of cells having a plurality of genotypes for producing mutant forms of a protein enzyme. The method includes loading a microcavity array with the library of cells; incubating the array in the presence of a substrate for the protein enzyme under conditions that allow for production of the enzyme of interest; imaging the array at selected intervals; measuring difference in enzyme activity for one or more cavities of the array. In various embodiments, the library of cells may be a library of yeast cells or library of bacterial cells. The protein enzymes may be displayed on the surface of the cells or the protein enzymes may be secreted by the cells. The method may further include adding an inhibitor for the enzyme.

In additional embodiments of the methods of the disclosure, the method includes extracting the contents of a cavity comprising cells having the phenotype of interest. The method may include directing electromagnetic radiation at an electromagnetic radiation absorbing material associated with the cavity. The source for the electromagnetic radiation may be a pulsed diode laser.

BRIEF DESCRIPTION OF THE FIGURES

FIGS. 6A-6D show an overview of example embodiments and methods of the disclosure.

FIG. 8, panel a) shows histograms of the fluorescence intensity in microcavities in the presence or absence of magnetic beads. FIG. 8, panel b) shows the fluorescence and bright-field images of the two conditions.

FIGS. 10A-10D shows the results of high-throughput screening of binding proteins using example systems and methods of the disclosure.

FIG. 17 shows sequence alignment of the A copies of ddOFP [SEQ ID NO: 1] and its parent, ddRFP [SEQ ID NO:2]. The original M66T mutation is encircled. Mutations acquired with three rounds of directed evolution are highlighted in grey.

DESCRIPTION

Figure 1:
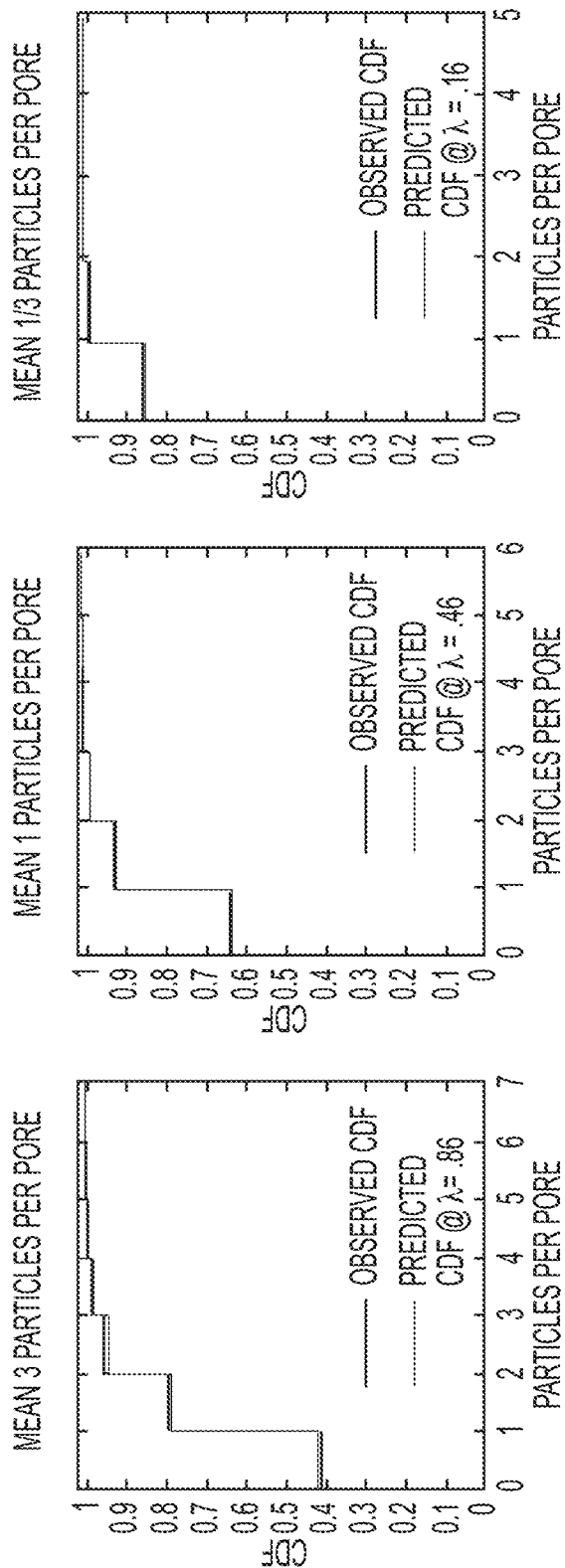
FIG. 1 shows the results of example embodiments of loading of microcavities of the disclosure following Poisson statistics.

In various embodiments, the disclosure is directed to the screening of large populations of biological elements for the presence or absence of subpopulation of biological elements or a single element. The embodiments of the disclosure can be used to discover, characterize and select specific interactions from a heterogeneous population of millions or billions of biological elements.

As an example, the disclosure is directed to a multipurpose technology platform, referred to herein as μSCALE (Microcavity Single Cell Analysis and Laser Extraction), that is capable of analyzing dense arrays of spatially segregated single clones or their products. Target cells are isolated post analysis using a precise but gentle laser-based extraction technique. This microcavity-based platform, which can image both static and dynamic fluorescence signals, enables functional analysis of millions of cell-produced protein variants within a time frame of minutes.

Methods of the disclosure include identifying and isolating of biological cells, including, but not limited to, cell lines that express or produce proteins, carbohydrates, enzymes, peptides, hormones, receptors; other cell lines that produce antibodies; genetically engineered cells; and activated cells. In addition, the disclosure includes methods for identifying biological cells hosting viruses displaying peptides of interest.

Moreover, the disclosure may be used to screen for a variety of biological activities including, but not limited to, the expression of surface receptor proteins, enzyme production, and peptide production. Furthermore, the disclosure may be used to screen a variety of test agents to determine the effect of the test agents on the desired biological activity. Other types of cells desired to be isolated and screened, other types of biological activity desired to be detected, and specific test agents to be screened will be readily appreciated by one of skill in the art. Embodiments of the disclosure are useful for high-throughput analysis of single cells and cell cultures. In some embodiments, the disclosure provides methods and apparatus to probe, for example, cell-to-cell interactions, single-cell growth and signaling dynamics, gene expression differences, and recombinant host cell expression levels.

Definitions

Unless otherwise defined, the technical and scientific terms used herein have the same meaning as commonly understood by one of ordinary skill in the art. Expansion and clarification of some terms are provided herein. All publications, patent applications, patents and other references mentioned herein, if not otherwise indicated, are explicitly incorporated by reference.

As used herein, the singular forms "a," "an", and "the" include plural referents unless the context clearly dictates otherwise.

The terms "binding partner", "ligand" or "receptor" as used herein, may be any of a large number of different molecules, or aggregates, and the terms are used interchangeably. In various embodiments, the binding partner may be associated with or bind an analyte being detected. Proteins, polypeptides, peptides, nucleic acids (nucleotides, oligonucleotides and polynucleotides), antibodies, saccharides, polysaccharides, lipids, receptors, test compounds (particularly those produced by combinatorial chemistry), may each be a binding partner.

The term "biological cell" or "cell" refers to any cell from an organism, including, but not limited to, insect, microbial, fungal (for example, yeast) or animal, (for example, mammalian) cells. A biological cell may also host and optionally, display, a virus of interest or a virus having a genotype of interest.

The term "biological element" as used herein, refers to any biological cell or bioreactive molecule. Non-limiting examples of the bioreactive molecules include proteins, nucleic acids, peptides, antibodies, antibody fragments, enzymes, hormones, and small molecules.

An "analyte" generally refers to an element of interest in a sample, for example a biological element of interest in a biological sample.

The term "bind" or "attach" as used herein, includes any physical attachment or close association, which may be permanent or temporary. Non-limiting examples of these associations are hydrogen bonding, hydrophobic forces, van der Waals forces, covalent bonding, and/or ionic bonding. These interactions can facilitate physical attachment between a molecule of interest and the analyte being measured. The "binding" interaction may be brief as in the situation where binding causes a chemical reaction to occur, such as for example when the binding component is an enzyme and the analyte is a substrate for the enzyme.

Specific binding reactions resulting from contact between the binding agent and the analyte are also within this definition. Such reactions are the result of interaction of, for example, an antibody and, for example a protein or peptide, such that the interaction is dependent upon the presence of a particular structure (e.g., an antigenic determinant or epitope) on a protein. Specific binding interactions can occur between other molecules as well, including, for example, protein-protein interactions, protein-small molecule interactions, antibody-small molecule interactions, and protein-carbohydrate interactions. Each of these interactions may occur at the surface of a cell.

The term "sample" as used herein is used in its broadest sense and includes environmental and biological samples. Environmental samples include material from the environment such as soil and water. Biological samples may be animal, including, human, fluid (e.g., blood, plasma, serum, urine, saliva), solid (e.g., stool), tissue, liquid foods (e.g., milk), and solid foods (e.g., vegetables). For example, a pulmonary sample may be collected by bronchoalveolar lavage (BAL), which comprises fluid and cells derived from lung tissues. Other examples of biological samples may comprise a cell, tissue extract, body fluid, chromosomes or extrachromosomal elements isolated from a cell, genomic DNA, RNA, cDNA and the like.

Turning now to the various aspects of the disclosure, the arrays of the disclosure include reaction cavities included in an extreme density porous array. As an example, microarrays contemplated herein can be manufactured by bundling millions or billions of cavities or pores, such as in the form of silica capillaries, and fusing them together through a thermal process. Such a fusing process may comprise the steps including but not limited to; i) heating a capillary single draw glass that is drawn under tension into a single clad fiber; ii) creating a capillary multi draw single capillary from the single draw glass by bundling, heating, and drawing; iii) creating a capillary multi-multi draw multi capillary from the multi draw single capillary by additional bundling, heating, and drawing; iv) creating a block assembly of drawn glass from the multi-multi draw multi capillary by stacking in a pressing block; v) creating a block pressing block from the block assembly by treating with heat and pressure; and vi) creating a block forming block by cutting the block pressing block at a precise length (e.g., 1 mm).

In one embodiment, the capillaries are cut to approximately 1 millimeter in height, thereby forming a plurality of micro-pores having an internal diameter between approximately 1.0 micrometers and 500 micrometers. In one embodiment, the micro-pores range between approximately 10 micrometers and 1 millimeter long. In one embodiment, the micro-pores range between approximately 10 micrometers and 1 centimeter long. In one embodiment, the micro-pores range between approximately 10 micrometers and 100 millimeters long. In one embodiment, the micro-pores range between approximately 0.5 millimeter and 1 centimeter long.

Very high-density micro-pore array that may be used in the various aspects of the disclosure. In example embodiments, each micro-pore can have a 5 µm diameter and approximately 66% open space (i.e., representing the lumen of each microcavity). In some arrays, the proportion of the array that is open ranges between about 50% and about 90%, for example about 60 to 75%, more particularly about 67%. In one example, a 10×10 cm array having 5 µm diameter microcavities and approximately 66% open space has about 330 million micro-pores. The internal diameter of microcavities may range between approximately 1.0 micrometers and 500 micrometers. In some arrays, each of the micro-pores can have an internal diameter in the range between approximately 1.0 micrometers and 300 micrometers; optionally between approximately 1.0 micrometers and 100 micrometers; further optionally between approximately 1.0 micrometers and 75 micrometers; still further optionally between approximately 1.0 micrometers and 50 micrometers, still further optionally, between approximately 5.0 micrometers and 50 micrometers.

In some arrays, the open area of the array comprises up to 90% of the open area (OA), so that, when the cavity size varies between 10 µm and 500 µm, the number of micro-pores per cm of the array varies between 458 and 1,146,500. In some arrays, the open area of the array comprises about 67% of the open area, so that, when the cavity size varies between 10 µm and 500 µm, the number of micro-pores per square cm of the array varies between 341 and 853,503. As an example, with a cavity size of 1 µm and up to 90% open area, each square cm of the array will accommodate up to approximately 11,466,000 micro-pores.

In one particular embodiment, a microcavity array can be manufactured by bonding billions of silica capillaries and then fusing them together through a thermal process. After that slices (0.5 mm or more) are cut out to form a very high aspect ratio glass micro perforated array plate. See, International Application PCT/EP2011/062015 (WO2012/007537), which is incorporated by reference herein in its entirety. A number of useful arrays are commercially available, such as from Hamamatsu Photonics K. K. (Japan), Incom, Inc. (Massachusetts), Photonis Technologies, S.A.S. (France) Inc. and others. In some embodiments, the microcavities of the array are closed at one end with a solid substrate attached to the array.

In certain embodiment, the sidewalls of the cavities of the arrays are not transmissive to electromagnetic radiation, or the cavities are coated with a material that prevents the transmission of electromagnetic radiation between cavities of the arrays. Suitable coating should not interfere with the binding reaction within the cavities or the application of forces to the cavities. Example coatings include sputtered nanometer layers of gold, silver and platinum. In another example, the capillary walls of the array are comprised of multiple layers, wherein one or more layers of the walls are made of a low refractive index material that prevents or substantially diminishes transmission of electromagnetic radiation between cavities of the array. An example embodiment of an array comprised of multiple layers is from Incom, Inc. (Charlton, Mass.).

In particular embodiments, the arrays are prepared under or subjected to either wet or dry hydrogen atmospheres in order to inhibit or block the transmission of electromagnetic radiation through the array. For instance, arrays of an alkaline-doped silicate glass can by reduced in a hydrogen atmosphere to make all of the surfaces of the array, including the walls of the cavities, opaque, darkened or blackened such that electromagnetic radiation is prohibited or prevented from transmitting between cavities of the array. This process can produce a lead silicate layer, not simply a coating, that may be several hundred angstroms thick. In one example, the array is constructed of Resistive Glass Product from Photonis USA Inc. (Sturbridge, Mass.).

Further example embodiments of the arrays include those shown in Table 2.

TABLE 2

| Material | Diameter (µm) | Array shape | Array size | Thickness (mm) | Capillaries |
| --- | --- | --- | --- | --- | --- |
| Clear glass | 10 | Square | 6.5 cm$^2$ | 1 | 4 × 10$^6$ |
| | 20 | Square | 4 cm$^2$ | 1 | 6.9 × 10$^5$ |
| | 40 | Square | 4 cm$^2$ | 1 | 1.7 × 10$^5$ |
| | 100 | Square | 4 cm$^2$ | 1 | 2.7 × 10$^4$ |
| Black glass | 25 | Round | 19.6 cm$^2$ | 1.5 | 1.9 × 10$^6$ |

In one aspect of the disclosure, the cavities of the array have a hydrophilic surface that facilitates the spontaneously uptake the solution into the cavity. In another aspect, a surface of the array may be treated to impart hydrophobicity. Combining these aspects, one surface of the array may be hydrophobic and the other surface may be hydrophilic. For example, a top surface and a bottom surface of the array are treated differently to impart hydrophilic characteristics on the top and hydrophobic characteristics on the bottom. The array may be treated sequentially, first with an agent to impart hydrophobicity, then on the opposite side with an agent to impart hydrophilicity.

Accordingly, the disclosure is directed to an array including a plurality of distinct cavities comprising open first ends and open second ends, wherein the open first ends of essentially all of the plurality of cavities collectively encompass a porous planar hydrophilic surface, and the open second ends of essentially all of the plurality of cavities encompass a porous planar hydrophobic surface. The surfaces include the open ends of the cavities and the interstitial spaces between the cavities.

The hydrophilic characteristics may be imparted using a corona treatment according to techniques known in the art. For example, a handheld Tesla coil (e.g. Electro-Technic Products BD-20AC) may be used such that several slow passes over the glass array surface (10-30 sec total exposure), a few millimeters above the array surface, is sufficient to impart suitable hydrophilic character.

In addition, the array may be treated with hydrophobic agents such as a polysiloxane, or composition comprising polysiloxane. As an example, the hydrophobic agent is a hydroxy-terminated polydimethylsiloxane. In a particular embodiment, the hydrophobic agent is RAIN-X® water repellant.

In order to provide an array having opposed hydrophilic and hydrophobic surfaces, one surface or the entire array can be treated to impart a hydrophilic characteristic. Thereafter the hydrophilic surfaces are protected, for example by application of a sealant, and the opposing surfaces are treated with a hydrophobic agent. In certain embodiments, the sealant is selected from commercially available tapes useful for this purpose, for example Scotch®—High-Performance Sure Start™ Packaging Tape, (Cat no. A8142-6). After application of the hydrophobic agent, the sealant tape is removed providing an array with opposing hydrophilic and hydrophobic surfaces. In a particular embodiment, the hydrophilic surface corresponds to the top of the array, which may be loaded with sample, and the hydrophobic surface corresponds to the bottom of the array.

In various aspects, the disclosure is directed to methods for screening a library of cells having a plurality of genotypes for a cell having a phenotype of interest, such a cell producing a protein or other molecule having a phenotype of interest. In general, the method is available for screening all cell types, e.g., mammalian, fungal, bacterial, and insect, that are able to survive and/or multiply in the array. Phenotypes of interest can include any biological process that renders a detectable result, including but not limited to production, secretion and/or display of polypeptides and nucleic acids. Libraries of cells having a plurality of genotypes associated with detectable phenotypes can be generated by methods involving error prone PCR, random activation of gene expression, phage display, overhang-based DNA block shuffling, random mutagenesis, in vitro DNA shuffling, site-specific recombination, and other methods generally known to those of skill in the art.

The array may be designed such that some or all cavities contain a single biological element to screen for the analyte. The concentration of the heterogeneous mixture of cells is therefore calculated according to the design of the array and desired analytes to identify. In embodiments where protein-producing cells are being screened, the method can eliminate clonal competition and screen a much larger diversity of cells.

The array may be loaded by contacting a solution containing a plurality of cells, such as a heterogeneous population of cells, with the array. In one embodiment, loading a mixture of antibody displaying or secreting cells, e.g., *E. coli* or yeast, evenly into all the microcavities involves placing a 500 µL droplet on the upper side of the array and spreading it over all the micro-pores. As an example, an initial concentration of approximately $10^9$ cells in the 500 µL, droplet results in approximately 3 cells (or subpopulation) per micro-cavity. In one embodiment, each micro-pore has an approximate volume of between 20-80 pL (depending on the thickness of the glass capillary plate of between 250 µm to 1 mm). Once the microcavities are loaded and incubated overnight, each microcavity should then contain approximately 2,000-3,000 cells per microcavity. In one embodiment, the cells may be cultivated for up to forty-eight hours or longer without loss of viability in order to maximize the proliferation yield. The plurality of cells may be animal cells, plant cells, and/or microbial cells, for example, bacterial or yeast cells. The cells may secrete or display at least one compound of interest, such as a recombinant compound of interest has an affinity for a binding partner.

In various examples, if there are approximately $10^9$ cells in an approximate 5000 µL solution then, on average, there should be approximately ten cells per micro-pore for an array having approximately $3$-$4 \times 10^6$ micro-pores, assuming a cavity volume of 50 picoliters. The exact number will depend on the volume of the cavity in the array and the concentration of cells in solution. As an example, each micro-pore may have a volume of ranging between approximately 20-80 picoliters.

A sample containing the population and/or library of cells may require preparation steps prior to distribution to the array. In some embodiments, these preparation steps include an incubation time. The incubation time will depend on the design of the screen and the cells being screened. Example times include 5 minutes, 1 hour, 3 hours, 6 hours, 12 hours, 1 day, 2 days and 3 days or more. The heterogeneous population of cells may be expanded in media prior to adding and/or loading onto the array. For certain applications, the cell containing media may be loaded into the array while in the exponential growth phase. Each cavity may have a volume of media that will allow the cells to replicate. For example, 20 picoliter can provide sufficient media to allow most single cells within a cavity to replicate multiple times. The array can optionally be incubated at any temperature, humidity, and time for the cells to expand and produce the target proteins or other biological elements of interest. Incubation conditions can be determined based on experimental design as is routine in the art.

In one embodiment, the method of the disclosure contemplates the concentration of the suspension of heterogeneous population of cells and the dimensions of the array are arranged such that 1-1000 biological elements, optionally, 1-500 biological elements, further optionally, 1-100 biological elements, still further optionally 1-10 biological elements, still further optionally, 1-5 biological elements, are distributed into at least one of the microcavities of the array.

The volume of the cell-containing volume loaded onto the array will depend on several variables, including for example the desired application, the concentration of the heterogeneous mixture, and/or the desired dilution of biological elements. In one specific embodiment, the desired volume on the array surface is about 1 microliter per square millimeter. The concentration conditions are determined such that the biological elements are distributed in any desired pattern or dilution. In a specific embodiment, the concentration conditions are set such that in most cavities of the array only single elements are present. This allows for the most precise screening of single elements.

These concentration conditions can be readily calculated. By way of example, in a cell screen, if the ratio of protein-producing cells to cavities is about 1 to 3, an array with $10^9$ cavities could be loaded with $3\times10^8$ different protein-producing cells in a 6 mL volume (6 mL=20 picoliter/pore$\times$3$\times$ $10^8$ cavities), and the vast majority of the cavities will contain at most a single clone. In certain other embodiments, single cells are not desired in each pore. For these embodiments, the concentration of the heterogeneous population is set so that more than one cell is found in each pore.

For example, when the array is properly loaded, cells should randomly distribute randomly into the array following Poisson distribution. According to this distribution, the probability, P, of loading a k number of cells in a microcapillary, where $\lambda$ is the bulk concentration (average number of cells in the microcapillary volume), is calculated by the following equation:

$$P(k, \lambda) = \frac{\lambda^k e^{-\lambda}}{k!} \qquad \text{(Equation 1)}$$

For single-cell per microcapillary (k=1), the equation becomes:

$$P(1,\lambda)=\lambda e^{-\lambda} \qquad \text{(Equation 2)}$$

Then to maximize the fraction of one cell per microcapillary, the local maximum of the equation 2 must be zero. Taking the derivative of equation 2:

$$p'^{(1,\lambda)}=e^{-\lambda}-\lambda e^{-\lambda}=e^{-\lambda}(1-\lambda)=0$$

In this example, when $\lambda=1$, the concentration of the loaded sample should be equal to 1 cell per microcapillary volume. Table 3 summarizes the concentration of the loaded sample for $\lambda=1$ for the different microcapillary arrays.

TABLE 3

| Material | Diameter (μm) | Thickness (mm) | Volume (pL) | Concentration for $\lambda = 1$ (cell/μL) |
|---|---|---|---|---|
| Clear glass | 10 | 1 | 80 | 12,730 |
|  | 20 | 1 | 310 | 3,180 |
|  | 40 | 1 | 1260 | 800 |
|  | 100 | 1 | 7850 | 130 |
| Black glass | 25 | 1.5 | 740 | 1,360 |

The concentration of the loading mixture is related to the average number of cells per microcapillary, $\lambda$, and microcapillary volume, ($V_{capillary}$) by the following equation:

$$\text{Loading volume} = \frac{\lambda}{V_{capillary}}$$

FIG. 1 shows fluorescent beads loaded into the array at three concentrations corresponding to means of 3, 1, and 1/3 particles per microcapillary ($\lambda$=3, 1, 1/3). The contents of 20,000 microcapillaries were counted, and the cumulative distribution functions (CDF) for each condition are plotted as red lines. While the cells randomly distribute into the array following a Poisson distribution, the observed and expected means differ by two- to three-fold, likely due to the high aspect ratio of the microcapillaries such that some particles may not travel into the imaging plane. Accordingly, higher than calculated sample concentrations can be used to overcome the difference between the observed and the expected means.

In other embodiments, the sample containing the heterogeneous population and/or library of cells may require preparation steps, e.g., incubation, after addition to the array. In other embodiments, each cell within each cavity is expanded (cells grown, phages multiplied, proteins expressed and released, etc.) during an incubation period. This incubation period can allow the cells to express or display the phenotype of interest, or allow virus to replicate.

After the cells have been loaded into the array, additional molecules or particles can be added or removed from the array without disturbing the cells. For example, any biological reactive molecule or particle useful in the detection of the cells can be added. These additional molecules or particles can be added to the array by introducing liquid reagents comprising the molecules or particles to the top of the array, such as for example by adding drop-wise as described herein in relation to the addition of the cells. To remove specific molecules from an array comprising biological elements, a solution can be prepared that is free from the selected molecule to be removed but contains all the rest of the molecules that are in the cavity array at the desired concentration. The droplet is added to the array as previously described. After the contents of the cavity array equilibrate with the droplet of this solution, the concentration of the selected molecule in the array will be reduced. The reduction amount depends on the volume of the added drop and the total volume contained in the array. To further reduce the concentration of the selected molecule, this step may be repeated after removing the first drop from the top of the array and then adding a second drop of liquid. Liquid can be removed from the top of the array by, for example, blotting the array with a paper towel or with a pipette.

As another example, a fluid retentive and pervious cover can be placed on the array to add, maintain, or exchange moisture, nutrients or other biological molecules to the array. The fluid retentive and pervious cover is described further herein.

In certain embodiments, particles may be included with one or more biological elements. The particles may be combined with one or more biological elements prior to introducing the combination into microcavities of the array or the particles may be provided in the microcavities before or after including one or more biological elements.

In certain embodiments the particles are provided with one or more biological elements at a concentration suitable to accumulate at the bottom of the microcavity cavity while leaving sufficient volume for the one or more biological elements. The concentration of the particles in solution depends on the specific particles. For example, after combining with one or more biological elements, a preparation of particles may provide a final concentration of between 1 mg/mL and 100 mg/mL. In certain embodiments, the particles in solution provide a final concentration of between 2.5 mg/mL and 50 mg/mL.

Once a cavity or cavities of interest are identified, the contents of the cavities can be extracted with the apparatus and methods described herein. The cavity contents can be further analyzed or expanded. Expanded cell populations from a cavity or cavities can be rescreened with the array according the methods herein. For instance, if the number of biological elements in a population exceeds the number of cavities in the array, the population can be screened with more than one element in each pore. The contents of the cavities that provide a positive signal can then be extracted to provide a subpopulation. The subpopulation can be screened immediately or, when the subpopulation is cells, it can be expanded. The screening process can be repeated until each cavity of the array contains only a single element. The screen can also be applied to detect and/or extract the cavity that indicates the desired analyte is therein. Following the selection of the cavity, other conventional techniques may be used to isolate the individual analyte of interest, such as techniques that provide for higher levels of protein production.

In certain embodiments, the top of the array is sealed with a membrane following the addition of sample to the cavities in order to reduce evaporation of the media from the cavities. One or more substantially gas and/or liquid impermeable membranes can be used to seal the surfaces of the array following the addition of a sample to the cavities. For example, typical food-service type plastic wraps such as polyvinylidene fluoride (PVDF) are suitable. In another embodiment, the membrane allows water vapor to equilibrate with the top liquid layer of the liquid in the pore, which can help prevent evaporation. For example, a film placed in contact with the top surface of the microcavity array, with water place on top of the film, would trap the contents of the cavities within each individual pore, but would allow water or media to flow into the cavities. Examples of useful members are nitrocellulose and NAFION® membranes. A similar arrangement could be obtained with a porous form of a polytetrafluoroethylene membrane (e.g., GORE-TEX® fabrics) having very small holes (e.g., 10-100 nm) that would trap any cells in the cavities but allow water, media and other reagents to pass into the cavities.

In certain embodiments the top of the array is covered with a semi-permeable composition that allows delivery of liquid and reagents to the cavities of the array while also preventing evaporation of the cavity contents. Similarly, the cover can allow for the exchange of liquid and reagents with the cavity contents. In one aspect, the semi-permeable composition is layered onto the top surface of the microcavity array after introduction of one or more samples into the array as described above.

In some embodiments the semi-permeable composition is a fluid retentive and pervious, and is able to store adequate volumes of liquid to allow the composition to impart and/or exchange fluid, nutrients and biologically reactive molecules with the contents of the array. Accordingly, the composition can retain and impart fluid, and in some aspects, the composition maintains equilibrium in concentration of biologically active molecules between the fluid in the cavities of the array and the fluid in the composition.

In one aspect, the composition is or includes a polymer gel that is contacted with the surface of the microcavity array. In certain embodiments, the polymer gel is selected from polyacrylamide, agar, or agarose. Those of skill in the art will recognize other suitable polymers useful in embodiments of the disclosure. In addition, polymer concentration in the polymer gel may vary according to the different embodiments and different applications. For example, the polymer concentration of agarose may include from 0.2%-10% weight by volume. In one aspect, the agarose may include 0.2, 0.5, 0.8, 1, 2, 3, 4, 5, 6, 7, 8, 9, or 10% weight by volume of agarose.

In various embodiments, the polymer gel layer is between 0.1-10 mm thick. In particular aspects, the polymer gel layer is 0.1, 0.25, 0.5, 0.75, 1, 2, 3, 4, 5, 6, 7, 8, 9, or 10 mm thick. In various aspects, the fluid retentive and pervious cover is sufficiently thick to avoid evaporation of the contents of the cavities of the array for a desired period of time.

The liquid phase of the fluid retentive and pervious cover may include solutions that are involved in a biological process. For example, the liquid phase may include a suitable aqueous buffering solution, e.g., a phosphate-buffered saline solution, a tris-buffered saline solution, or a non-buffered aqueous phase. In various embodiments the liquid phase may include cell culture media to provide nutrients or biologically reactive molecules to cells in the cavities over the course of hours or days. In one aspect, the liquid phase may include a lysis buffer.

In one aspect, the cover allows for free diffusion between the cover and cavities. Accordingly, in certain embodiments a semi-permeable gel is used to deliver desirable molecules uniformly into all the microcavities. In certain aspects, the gel is used to dilute out or "wash" non-desirable molecules already in the microcavities. In certain embodiments, a cell-culture media based gel is used to provide a contact bridge between microcavities, allowing growth factors to be transferred between cells but not the cells themselves. In certain aspects, a cell-culture based gel is used to study paracrine signaling between cells. In other embodiments, a gradient of a molecule of interest can be impregnated in the gel, which will allow different stimulus to be provided to microcavities at different locations of the array.

The use of the nutrient rich gel allows for the growth of cells within the cavities of the array, for example bacterial, yeast, and mammalian cells in the arrays. For each cell type, standard media for a particular species may be used with or without modification. In particular embodiments, HEPES (e.g., 25 mM) instead of phosphate buffer or Tris-HCl pH 7.5 (e.g., 25 mM) instead of phosphate buffer in a certain induction media may lead to higher protein expression. A HEPES or Tris-HCl substituted induction media leads to higher protein expression levels in yeast than an induction media containing a higher concentration of phosphate buffer or an induction media supplemented with 2 g/L dextrose or 20 g/L raffinose pentahydrate.

Accordingly, in one aspect, the disclosure is directed to an array including a plurality of distinct cavities comprising open first ends and open second ends, wherein the open first ends of essentially all of the plurality of cavities collectively comprise a first porous planar surface, and the open second ends of essentially all of the plurality of cavities comprise second porous planar surface, and a cover for the first surface that imparts at least one of moisture, a nutrient, or a biologically reactive molecule, to contents of the cavities.

Particular examples of a media infused fluid and pervious cover for the array are as follows:

1) 1% agarose gel with water and a 1% agarose gel with phosphate-buffered saline to maintain the contents/osmotic pressure in the microcavities for the cells. This gel may be used to ensure the cells remain in the bottom of the array.

2) 1% agarose gel with yeast growth media to growth yeast over 48 hours.

3) 1% agarose gel with enzyme reaction buffer to ensure that the enzyme reaction remains properly buffered.

4) 1% agarose gel with enzyme reaction buffer and reaction substrate to deliver reaction substrate to the cavities uniformly.

5) 1% agarose gel with mammalian cell media to deliver nutrients to mammalian cells.

6) 1% agarose gel with mammalian cell media which bridged cavities, allowing the contents of a cavity to influence cells in distant cavities.

In the various embodiments described herein, a 1.5 mm layer of 1% agarose and water can be placed on top the array. A clear gel such as agarose is suited for bright-field imaging, as it does not block the light source located above the array In addition, the fluid retentive and pervious cover can be exchanged during a period of cell incubation and or expansion in the array. In this embodiment, nutrients or other reagents are added or washed out by exchanging the cover on top with a new cover containing reagents or other compounds. For example, a substrate for an enzymatic reaction could be embedded in the cover and added to the reaction at a precise time (e.g., after cell growth) by switching out from a cover containing growth media to a gel containing substrate.

Following incubation, addition of components, and/or another preparation step, the array is scanned to identify cavities containing cells having a phenotype of interest, which may include cells hosting viruses that display a phenotype of interest. For example, following established guidelines for quantitative wide-field microscopy, the inter-capillary variability in fluorescence signals detected from the array may be measured. The passive nature of microcapillary filling process results in a uniform meniscus level across the entire array. This uniformity, coupled with gravitational sedimentation of the loaded cells, simplifies the establishment of the imaging focus plane without the need for autofocus. Rather, the focus may be set at three distantly spaced points on the array, for example the corners. From these three points, the plane of the microcapillary array may be calculated.

Figure 2:
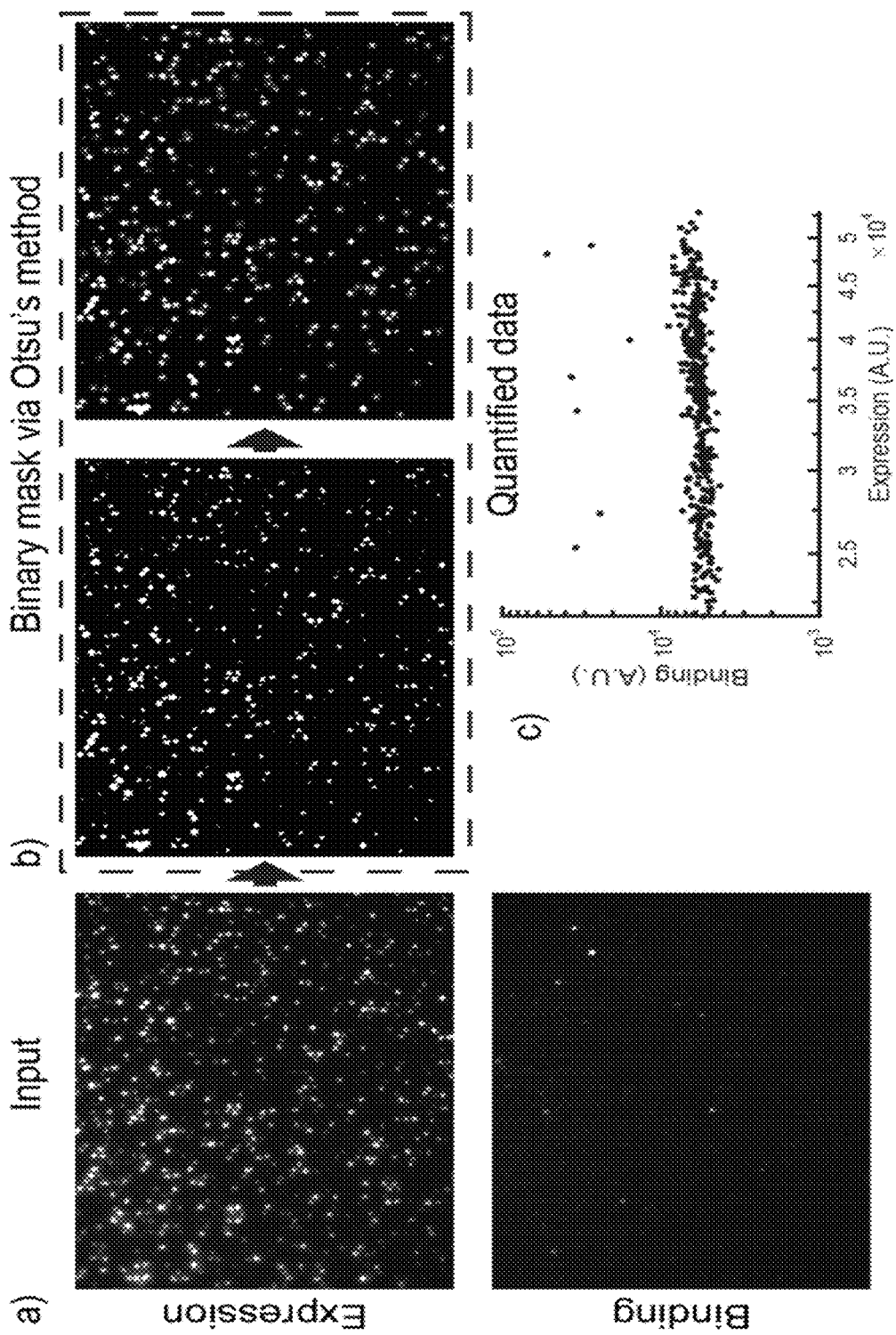
FIG. 2 shows an example of the conversion of a raw image for protein expression and binding converted into a binary mask using Otsu's method according to an example method of the disclosure.

As shown in FIG. 2, raw input grayscale images may be converted to binary images via thresholding (Otsu's method) with optional user input on minimum brightness and threshold levels. Raw input images for expression and binding are shown in panel a). Panel b) shows thresholding with Otsuka's method. The features may be filtered by size (minimal and maximal) and roundness (eccentricity). The features that pass the user defined parameters are highlighted. Panel c) shows the filtered binary mask may be applied to the raw image and the fluorescence values may be quantified and plotted. Background subtraction can be performed to improve quantification at the cost of additional computing speed. Feature filtering may eliminate a bulk of the fluorescent debris, and spatial segregation and direct imaging can provide enough time for interrogation of individual single cells. This ability enables researchers to distinguish between fluorescent debris and cells, decreasing false positive rates.

Optimization of quantitative wide-field microscopy may result optical vignetting, which is a reduction of brightness at the edges of the image that likely due to the increased camera sensor size. To compensate, the image may be cropped to eliminate the regions with vignetting. This may reduce imaging speed by requiring more images to cover a given area. In addition flat-field correction may be used in cases where absolute quantification is needed. Following the protocol established by Wolf et al. (*Methods Cell Biol.* (2013) 114:337-67), four images may be taken: a homogeneous fluorescent reference ($H_{flat}$), a dark image in a region of no fluorescence ($H_{dark}$), a dark image in a region of no fluorescence in the sample ($S_{dark}$), and the sample image ($S_{image}$). The flat-field corrected image can be found by the following equation:

$$Image_{corrected} = \frac{S_{image} - S_{dark}}{H_{flat} - H_{dark}}$$

Extraction of Microcavity Contents

Based on the optical information received from a detector associated with the array of cavities, target cavities with the desired properties are identified and their contents extracted for further characterizations and expansion. The disclosed methods maintain the integrity of the biological elements in the cavities. Therefore the methods disclosed herein provide for the display and independent recovery of a target population of biological elements from a population of up to billions of target biological elements. This is particularly advantageous for embodiments where cells are screened.

For example, the signals from each cavity are scanned to locate the binding events of interest. This identifies the cavities of interest. Individual cavities containing the desired clones can be extracted using a variety of methods. For all extraction techniques, the extracted cells or material can be expanded through culture or amplification reactions and identified for the recovery of the protein, nucleic acid or other biological element. As described above, multiple rounds of screening are also contemplated. Following each screening, one or more cavities of interest can be extracted as described herein. The contents of each cavity can then be screened again until the desired specificity is achieved. In certain embodiments, the desired specificity will be a single biological element per pore. In these embodiments, extraction may follow each round of the screening before the cavities include only a single element.

In one embodiment, the method includes isolating cells located in the microcavities by pressure ejection. For example, a separated microcavity array is covered with a plastic film. In one embodiment, the method further provides a laser capable of making a hole through the plastic film, thereby exposing the spatially addressed micro-pore. Subsequently, exposure to a pressure source (e.g., air pressure) expels the contents from the spatially addressed microcavity. See WO2012/007537.

Another embodiment is directed to a method of extracting a solution including a biological element from a single microcavity in a microcavity array. In this embodiment, the microcavity is associated with an electromagnetic radiation absorbent material so that the material is within the cavity or is coating or covering the microcavity. Extraction occurs by focusing electromagnetic radiation at the microcavity to generate an expansion of the sample or of the material or both or evaporation that expels at least part of the sample from the microcavity. The electromagnetic radiation source may be the same or different than the source that excites a fluorescent label. The source may be capable of emitting multiple wavelengths of electromagnetic radiation in order to accommodate different absorption spectra of the materials and the labels.

In some embodiments, subjecting a selected microcavity to focused electromagnetic radiation can cause an expansion of the electromagnetic radiation absorbent material, which expels sample contents onto a substrate for collecting the expelled contents.

In some embodiments the laser should have sufficient beam quality so that it can be focused to a spot size with a diameter roughly the same or smaller than the diameter of the pore. For instance, when the array material is capable of absorbing electromagnetic radiation, for instance when the array is manufactured or coated with an electromagnetic radiation absorbing material, the laser spot diameter may be smaller than the capillary diameter with the laser focused at the material-sample interface. In some embodiments, the material of the array itself, without any coating, such a darkened or blackened capillary array, can function as the electromagnetic radiation absorbent material. For example, as further described herein, array may be constructed of a lead glass that has been reduced in a hydrogen atmosphere. In various embodiments, the focus of the laser may be 90%, 80%, 70%, 60%, 50%, 40%, 30%, 20% 10%, 9%, 8%, 7%, 6%, 4%, 4%, 3%, 2% or 1% the diameter of the cavity.

In one aspect, the electromagnetic radiation is focused on the electromagnetic radiation absorbing material, resulting in linear absorption of the laser energy and cavitation of the liquid sample at the material/liquid interface. The electromagnetic radiation causes an intense localized heating of an electromagnetic radiation absorbing material of the array causing explosive vaporization and expansion of a thin layer of fluid in contact with the material without heating the remainder of the contents of the cavity. In most applications, directing of electromagnetic radiation to the material should avoid heating that liquid that is not in contact with the material at the focus of the radiation to avoid heating the liquid contents of the microcavity and impacting the biological material in the cells. Accordingly, while a very thin layer of liquid in proximity the focus of the electromagnetic radiation is heated to cause the explosive evaporation and expansion of the liquid, the amount of energy necessary to disrupt the meniscus is not sufficient to cause a significant increase in temperature of the entire liquid contents. In one aspect the laser is focused on the material of a cavity of the array adjacent the meniscus itself, causing a disruption of the meniscus without heating the liquid contents of the cavity other than the heating associated with the vaporization of a small amount of liquid at the portion of the meniscus adjacent the laser focus.

In certain embodiments, extraction from cavities of the array is accomplished by excitation of one or more particles in the microcavity, wherein excitation energy is focused on the particles. Accordingly, some embodiments employ energy absorbing particles in the cavities and an electromagnetic radiation source capable of discreetly delivering electromagnetic radiation to the particles in each cavity of the array. In certain embodiments energy is transferred to the particles with minimal or no increase in the temperature of the solution within the microcavity. In certain aspects, a sequence of pulses repeatedly agitates magnetic beads in a cavity to disrupt a meniscus, which expels sample contents onto a substrate for collecting the expelled contents.

The electromagnetic radiation emission spectra from the electromagnetic radiation source must be such that there is at least a partial overlap in the absorption spectra of the electromagnetic radiation absorbent material associated with the cavity. In certain embodiments, individual cavities from a microcavity array are extracted by a sequence of short laser pulses rather than a single large pulse. For example, a laser is pulsed at wavelengths of between about 300 and 650, more particularly about 349 nm, 405 nm, 450 nm, or 635 nm. The peak power of the laser may be between, for example, approximately 50 mW and 100 mW. Also, the pulse length of the laser may be from about 1 msec to about 100 msec. In certain embodiments, the total pulse energy of the laser is between about 10 µJ and about 10 mJ, for instance 10, 25, 50, 100, 500, 1000, 2500, 5000, 7500, or 10,000 µJ. In certain embodiments, the diameter of the focus spot of the laser beam waist is between about 1 µm and about 20 µm, for instance 1, 2, 3, 4, 5, 6, 7, 8, 9, 10, 11, 12, 13, 14, 15, 16, 17, 18, 19 or 20 µm. In a particular example embodiment, the laser is pulsed at 75 mW peak power, 1 msec pulse length, 10 msec pulse separation, 2 µm diameter beam, with a total of 10 pulses per extraction.

In some embodiments, cavities of interest are selected and then extracted by focusing a 349 nm solid state UV laser at 20-30% intensity power. In one example, the source is a frequency tripled, pulsed solid-state Nd:YAG or Nd:YVO4 laser source emitting about 1 microJoule to about 1 milliJoule pulses in about a 50 nanosecond pulse. In another example, the source is a diode-pumped Q-switched Nd:YLF Triton UV 349 nm laser (Spectra-Physics). For instance, the laser may have a with a total operation time of about 15-25 ms, delivering a train of 35-55 pulses at about 2-3 kHz, at a pulse width of about 8-18 nsec, with a beam diameter of about 4-6 µm, and total power output of 80-120 µJ. In one particular example, the laser may have a with a total operation time of about 15-20 ms, delivering a train of about 41-53 pulses at about 2.5 kHz, at a pulse width of about 10-15 nsec, with a beam diameter of about 5 µm, and total power output of 100 µJ. Both continuous wave lasers with a shutter and pulsed laser sources can be used in accordance with the disclosure.

In some embodiments, a diode laser may be used as an electromagnetic radiation source. In certain embodiments, the focus of diode laser has a beam waist diameter between about 1 µm and about 10 µm, for instance a 1, 2, 3, 4, 5, 6, 7, 8, 9 or 10 µm diameter. The diode laser may have a peak power of between about 20 mW and about 200 mW peak power, for instance about 20 mW, 40 mW, 60 mW, 80 mW, 100 mW, 110 mW, 120 mW, 130 mW, 140 mW, 150 mW, 160 mW, 170 mW, 180 mW, 190 mW or 200 mW peak power. The diode laser can be used at wavelengths of between about 300 and about 2000 nm, for instance about 405 nm, 450 nm, or 635 nm wavelength. In other embodiments, an infrared diode laser is used at about 800 nm, 980 nm, 1300 nm, 1550 nm, or 2000 nm wavelengths. Longer wavelengths are expected to have less photoxicity for any given sample.

In certain embodiments, a diode laser is pulsed at between about 2 to 20 pulses, for instance 2, 4, 6, 8, 10, 12, 14, 16, 18, and 20 pulses, with a pulse length of about 1 to 10 msec, for instance, 1, 2, 3, 4, 5, 6, 7, 8, 9, and 10 msec, and having a pulse separation of approximately 10 msec to 100 msec, for instance 10, 20, 30, 40, 50, 60, 70, 80, 90 and 100 msec. In an example embodiment, the diode laser is an Oclaro HL63133DG laser with a peak power of 170 mW operating at a wavelength of 635 nm. In another example embodiment, the diode laser is an Osram PL450B laser operating at 450 nm.

In other example embodiments, a diode laser or a Triton laser are focused to diameters of between 1 to 10 microns. The lasers emit a train of 10 to 50 pulses over a time period of 10 msec to 100 msec. Each individual pulse has a time duration of 1 msec (diode laser) or 10 nsec (Triton laser). The total pulse train energy is approximately 100 microJoules. The laser energy is absorbed within a volume in the microcapillary which is approximately a cylinder with a diameter roughly equal to the diameter of the laser beam waist and a height determined by the absorption length of the laser beam. If magnetic beads are in the capillary the laser pulse energy is absorbed by the beads, primarily heating the surface of the bead that is directly exposed to the laser. The liquid in immediate proximity to this surface is explosively vaporized which propels the beads within the capillary. The explosive motion of the beads along with vaporization of the nearby liquid disrupts the meniscus and empties the capillary. If the material of the array itself absorbs the light then the laser energy is deposited primarily in the portion of the capillary wall upon which the laser is incident. If sufficient laser energy is absorbed in this absorbing volume in a short enough time, then the heat will not have time to diffuse to the surrounding liquid. The liquid in the absorption volume will be explosively vaporized by the laser pulse, causing a rapid expansion of a portion of the sample, which disrupts the meniscus and empties the contents of the microcapillary, and heat diffusion to the surrounding liquid outside of the absorbing volume will be minimized.

In a particular example, an individual laser pulse has a duration of approximately 1 msec and the beam waste diameter is approximately 10 microns. In this example, the single laser pulse will heat the volume of liquid within the absorption region of the laser beam and during the pulse the heat will diffuse only a few microns outside of the absorbing region. The energy deposited during the laser pulse causes the temperature of the liquid in the absorbing region to rise abruptly to many times the vaporization temperature. The liquid is explosively vaporized in this absorption region while the surrounding region stays essentially at its original temperature. The explosive vaporization of liquid within the absorbing region disrupts the meniscus and the liquid is expelled from the microcapillary with negligible heat diffusion from the absorbent material to the surrounding medium and resulting in negligible or no heating of the total liquid contents of the microcapillary.

The equation describing the distance of propagation of heat within a substance over a short time scale is:

$$(d=\sqrt{(\alpha^* \tau)}).$$

Where d is the characteristic thermal diffusion distance, $\alpha$ is the thermal diffusion coefficient, and $\tau$ is the energy deposition time or laser pulse length. For water $\alpha$=0.143 mm$^2$/sec and with $\tau$=1 msec this equation results in a predicted diffusion length of about 10 microns. A total pulse energy of 100 microJoules deposited in the approximate absorption cylinder volume determine by a beam with a waist diameter of 10 microns and a height of 10 microns (~10e-12 cm$^3$) will raise the temperature of the liquid in this volume to many, many times the evaporation temperature of the liquid, resulting in explosive expansion of liquid in this volume.

The Veritas laser supplies a train of about 40, 5 nsec pulses, each pulse separated by about 500 microseconds. Each pulse causes explosive expansion of the liquid in the absorbing volume, propelling the beads (if present) and disrupting the meniscus. The diode laser similarly delivers a train of ten 1 msec pulses separated by several milliseconds, which interacts with liquid in the capillary in a similar fashion. In both cases using multiple pulses in a pulse train enhances the extraction efficiency compared to using a single high energy pulse.

When microspheres used, the equation for the thermal relaxation time ($t_r$) for uniform spheres of diameter d is $$t_r = \frac{d^2}{27\,k} = \frac{(1\ \mu m)^2}{27*.143\times 10^{-6}\frac{m^2}{s}} = 259\ ns$$

As long as the laser pulse is <~300 ns (this changes depending on the diameter of the beads), there will be thermal confinement and rapid localized heating of the absorbent material.

In further example embodiments, the following parameters may be used
1) Laser parameters
   a. Veritas laser
      i. Triton UV 349 nm laser (diode-pumped Q-switched Nd:YLF laser, Spectra-Physics)
      ii. Total operation time: 18±2 ms (n=5 measurements), delivering a train of 46.6±5.9 pulses at 2.5 kHz
      iii. Pulse width: 10-15 nsec
      iv. Beam diameter: 5 µm
      v. Total power: 100 µJ
2) Absorbing material
   a. Superparamagnetic iron oxide-doped microbeads
      i. Diameter ~1 um (can range from 100 nm-10 um)

$$\text{Thermal relaxation time: } t_r = \frac{d^2}{27\,k} = \frac{(1\ \mu m)^2}{27*.143\times 10^{-6}\frac{m^2}{s}} = 259\ ns$$

b. Black capillary walls (e.g., lead-silicate layer from reducing alkaline-doped silicate glass in a hydrogen atmosphere).

Materials within the cavity can be, for example, the particles used in the binding assays as described above. Accordingly, the particles may have a property that allows the particles to respond to a force in order to accumulate at a surface, and also include an electromagnetic radiation absorbent material, e.g., DYNABEAD® particles. In various embodiments, energy is applied to the particles while they are accumulated at the surface after the signal at the surface is detected (by continued or reapplication of a force), or the force is removed so that the particles return to the sample solution. Alternatively, the cavities include particles or other materials that do not participate in the binding reactions but are to provide extraction of the contents as described herein. These particles may be functionalized so that they bind to the walls of the micro-cavities independent of the binding reaction of the assay. Similar materials can be used to coat or cover the microcavities, and in particular, high expansion materials, such as EXPANCEL® coatings (AkzoNobel, Sweden). In another embodiment the EXPANCEL® material can be supplied in the form of an adhesive layer that is bonded to one side of the array so that each cavity is bonded to an expansion layer.

Focusing electromagnetic radiation at a microcavity can cause the electromagnetic radiation absorbing material to expand, which causes at least part of the liquid volume of the cavity to be expelled. When the material is heated to cause rapid expansion of the cavity content, a portion of the of the contents may be expanded up to, for example, 1600 times, which causes a portion of the remainder of the contents to be expelled from the cavity.

Without rapid expansion of the material or cavity contents, heating can cause evaporation of the contents, which can be collected by condensing the contents on a substrate. For example, the substrate can be a hydrophobic micropillar placed at or near the opening of the cavity. Expulsion of the contents may also occur as the sample evaporates and condenses on the walls of a capillary outside the meniscus, which causes the meniscus to break and release the contents of the capillary.

Microcavities can be open at both ends, with the contents being held in place by hydrostatic force. During the extraction process, one of the ends of the cavities can be covered to prevent expulsion of the contents from the wrong end of the cavity. The cavities can be covered in the same way as, for example, the plastic film or polymer gel coatings described above. Also, the expansion material may be bonded as a layer to one side of the array.

In some embodiments, the capture surface comprises a hygroscopic layer upon which the contents of the cavity are expelled. The hygroscopic layer attracts water and prevents the deformation of the optical surface allowing clear imaging of the cavity contents. In certain embodiments, the layer is a hygroscopic composition, such as witch hazel, a solution including glycerol, or a solution of phosphate buffered saline with bovine serum albumin and sorbitol in concentrations for example of 0.1% weight/volume BSA and 1 M sorbitol. The layer can be applied, for example, by spreading, wiping or spraying and should create a uniform dispersion on the surface. Typically, the layer is about 10-100 μm thick, as long as the layer does not distort the EM radiation passing through the layer and does not touch the array above.

In another embodiment, once the cellular contents of one or more cavities have been extracted onto a capture surface, the surface may be contacted with a culture matrix to allow transfer of the contents of the cavity to the matrix. Once the contents have been transferred to the matrix, cells may be allowed to propagate on the matrix. The matrix may be any solid, semi-solid, or gel-type media (e.g., agarose) that allows for the growth and replication of cells. The matrix may be incubated as required. The capture surface can be removed immediately after contact or within minutes, hours, days or weeks as appropriate to ensure viability of the cell culture(s) in the matrix. Alternatively, the cells may be extracted directly onto the growth matrix, assuming the matrix has sufficient transparency to allow for the extraction laser to penetrate the matrix without sufficient focus to transfer energy to the array as described herein.

Detection of analytes in accordance with the disclosure requires, in some embodiments, the use of an apparatus capable of applying electromagnetic radiation to the sample, and in particular, to an array of cavities, such as a microarray. The apparatus must also be capable of detecting electromagnetic radiation emitted from the sample, and in particular a sample cavity.

In one embodiment, the electromagnetic radiation source of the apparatus is broad spectrum light or a monochromatic light source having a wavelength that matches the wavelength of at least one label in a sample. In a further embodiment, the electromagnetic radiation source is a laser, such as a continuous wave laser. In yet a further embodiment, the electromagnetic source is a solid state UV laser. A non-limiting list of other suitable electromagnetic radiation sources include: argon lasers, krypton, helium-neon, helium-cadmium types, and diode lasers. In some embodiments, the electromagnetic source is one or more continuous wave lasers, arc lamps, or LEDs.

In some embodiments, the apparatus comprises multiple (one or more) electromagnetic sources. In other embodiments, the multiple electromagnetic (EM) radiation sources emit electromagnetic radiation at the same wavelengths. In other embodiments, the multiple electromagnetic sources emit different wavelengths in order to accommodate the different absorption spectra of the various labels that may be in the sample.

In some embodiments, the multiple electromagnetic radiation sources comprise a Triton UV laser (diode-pumped Q-switched Nd:YLF laser, Spectra-Physics) operating at a wavelength of 349 nm, a focused beam diameter of 5 μm, and a pulse duration of 20 ns. In still further embodiments, the multiple electromagnetic radiation sources comprise an X-cite 120 illumination system (EXFO Photonic Solutions Inc.) with a XF410 QMAX FITC and a XF406 QMAX red filter set (Omega Optical). In an example embodiment, a diode laser is a Oclaro HL63133DG laser with a peak power of 170 mW operating at a wavelength of 635 nm. In another example embodiments, the diode laser is an Osram PL450B laser operating at 450 nm.

The apparatus also includes a detector that receives electromagnetic (EM) radiation from the label(s) in the sample, array. The detectors can identify at least one cavity (e.g., a microcavity) emitting electromagnetic radiation from one or more labels.

In one embodiment, light (e.g., light in the ultra-violet, visible or infrared range) emitted by a fluorescent label after exposure to electromagnetic radiation is detected. The detector or detectors are capable of capturing the amplitude and duration of photon bursts from a fluorescent moiety, and further converting the amplitude and duration of the photon burst to electrical signals. In some embodiments the detector or detectors are inverted.

Once a particle or element is labeled to render it detectable, or if the particle possesses an intrinsic characteristic rendering it detectable, any suitable detection mechanism known in the art may be used without departing from the scope of the disclosure, for example a CCD camera, a video input module camera, a Streak camera, a bolometer, a photodiode, a photodiode array, avalanche photodiodes, and photomultipliers producing sequential signals, and combinations thereof. Different characteristics of the electromagnetic radiation may be detected including: emission wavelength, emission intensity, burst size, burst duration, fluorescence polarization, and any combination thereof. As one example, a detector compatible with the disclosure is an inverted fluorescence microscope with a 20× Plan Fluorite objective (numerical aperture: 0.45, CFI, WD: 7.4, Nikon) and an ORCA-ER cooled CCD camera (Hamamatsu).

The detection process can also be automated, wherein the apparatus comprises an automated detector, such as a laser scanning microscope.

In some embodiments, the apparatus as disclosed can comprise at least one detector; in other embodiments, the apparatus can comprise at least two detectors, and each detector can be chosen and configured to detect light energy at the specific wavelength range emitted by a label. For example, two separate detectors can be used to detect particles that have been tagged with different labels, which upon excitation with an electromagnetic source, will emit photons with energy in different spectra.

Evaporation from the cavities of a microcavity array complicates the measurement of the contents of the microcavity by changing the height of the meniscus in the cavity. In particular, mass transfer due to evaporation of the liquid in the cavity occurs between the cavity and any surface nearby if that surface is at a lower temperature. This evaporation changes the height of the meniscus in the cavity which raises the position of the cells in the cavity and can make laser extraction more difficult and also can raise the signal producing element (e.g., cell, beads) out of the focal plane of the microscope.

Figure 3A:
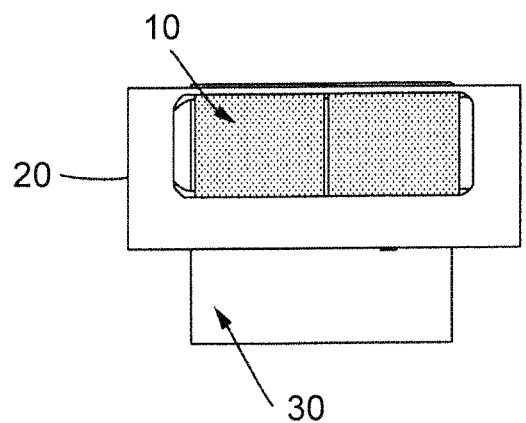
FIGS. 3A and 3B shows an example embodiment of a microcapillary array associated with a transparent glass transfer plate with a conductive coating.

To address the mass transfer of liquid out of the array, the microcavity array may be located adjacent or between one or two transparent glass plates with one surface of each glass plate coated with a transparent conductive coating. For example, FIG. 3A shows a top view of microcapillary array 10 in a holder 20 with a single glass plate 30 underneath the array. A second plate above the array is not shown for the purposes of clarity but may be present. A transparent coating (not shown) on the plate(s) can be used to uniformly heat the glass plate(s) in order to control their temperature. The coating may be, for example, indium titanium oxide (ITO), which is transparent in the visible region of the spectrum. The transparency of the coating allows excitation light delivered from above (e.g., brightfield) or below (e.g., epi fluorescence in an inverted microscope). The coated glass plates also allow a capture surface (not shown) as described herein to be inserted between the plates that provides for the collection of contents extracted from the capillaries of the array. The plate in the vicinity of the capture surface heats the capture surface to prevent condensation of the contents of the cavities on the surface.

Figure 3B:
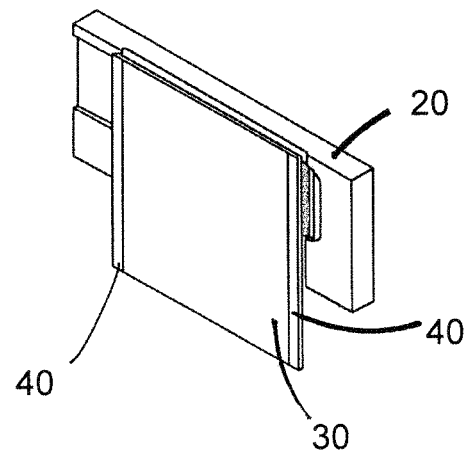

FIG. 3B shows a bottom view of the holder 20 and the plate 30. Conductive strips can be applied to the coating on two opposing edges 40 of the glass plate. These conductive strips can be, for example, a copper tape with a conducting adhesive, a line of conducting epoxy, or a deposited conducting layer (e.g., gold, silver, titanium, etc). A voltage applied to the strips results in current flow through the coating. Because the coating has a finite resistance, the current flow results in Ohmic heating of the surface of the glass plate. The heating across the plate should be uniform provided the current flow through the plate is uniform. The temperature of the surface of the glass plate can be measured with a thermocouple, thermistor or other temperature probe, and a feedback circuit can be used to stabilize the temperature. The proper amount of heating can be determined by observing the condensation on the bottom or top glass plates and the temperature increased to eliminate any condensation. Alternatively the height of the meniscus can be measured by focusing on the cells or magnetic beads in the cavities and the temperature increased or decreased to lower the meniscus to the bottom of the well.

In various aspects, the disclosure is directed to kits for the detection, identification, and/or characterization of analytes or cellular processes of interest. In some embodiments, the kits contain antibodies specific for an analyte, such as a protein of interest, in addition to detection reagents and buffers. In other embodiments, the kits contain reagents specific for the detection of mRNA or cDNA (e.g., oligonucleotide probes or primers). In various embodiments, the kits contain all of the components necessary to perform a detection assay, including all controls, instructions for performing assays, and any necessary software for analysis and presentation of M magnetic particles provided in kits may be functionalized with a binding partner for the analyte. Labels may be conjugated to a binding partner for the analyte or other sample component. The kits may also include second, third, or fourth, etc. set of particles that are functionalized to bind second, third, or fourth, etc. analytes in the sample, or to provide for the normalization of the sample components between microcavities of the array. Stabilizers (e.g., antioxidants) to prevent degradation of the reagents by light or other adverse conditions may also be part of the kits.

While the instructional materials typically include written or printed materials they are not limited to such. Any medium capable of storing such instructions and communicating them to an end user is contemplated by this disclosure. Such media include, but are not limited to electronic storage media (e.g., magnetic discs, tapes, cartridges, chips), optical media (e.g., CD ROM), and the like. Such media may include addresses to internet sites that provide such instructional materials.

In an embodiment, the disclosure is directed to a method comprising identifying new therapeutic drugs. For example, a drug binding partner known to be involved in a disease condition (i.e., for example, an antibody, a biological receptor and/or enzyme) can be screened against a plurality of cells secreting or surface-displaying various compounds suspected of having affinity for the binding partner. The microcavities containing the cells displaying or secreting compounds having the highest binding affinity can be identified with an appropriate reporter system. The contents of the identified microcavities can be extracted and used for future development. In another embodiment, cell viability or interaction may be screened in the presence of a compound, such as a therapeutic compound. Cells having viability in the presence or activity of interest in the presence of the compound may be further analyzed.

In an embodiment, the disclosure is directed to a method for determining antigen-antibody binding such that each cell produces antibodies and secretes the antibodies into the microcavity. The antibody may be a recombinant antibody and/or a monoclonal antibody. The cell or cells may produce more than one kind of antibody or multiple copies of the same antibody. In one embodiment, the disclosure contemplates a method comprising identifying diagnostic antibodies. For example, a plurality of cells secreting various antibodies suspected of having affinity for the binding partner can be screened for binding partners known to be involved in a disease condition (i.e., for example, an antigen and/or epitope). The microcavities containing the cells displaying or secreting compounds having the highest binding affinity can be identified with an appropriate reporter system.

In an embodiment, the disclosure is directed to a method comprising identifying protein-protein interactions. A plurality of cells secreting or surface-displaying various proteins and/or peptides suspected of having affinity for binding partners known to be involved in a disease condition (i.e., for example, a protein and/or peptide) can be screened against the binding partners. The microcavities containing the cells displaying or secreting compounds having the highest binding affinity can be identified with an appropriate reporter system.

As an example, the disclosure is directed to a method of identifying protein binders against a clinical target Growth Arrest Specific 6 (Gas6), which binds to Axl receptor tyrosine kinase and mediates immune function, blood coagulation, and tumor cell invasion and migration. In accordance with the method, a naïve library of yeast-displayed single-chain variable fragments (scFvs) can be screened to identify a variant that binds to Gas6 with high affinity.

In an embodiment, the disclosure is directed to a method comprising identifying protein-nucleic acid interactions. Nucleic acid that are binding partners known to be involved in a disease condition (e.g., a deoxyribonucleic acid and/or a ribonucleic acid and/or a SOMAmer and/or an aptamer) can be screened against a plurality of cells secreting or surface-displaying various proteins and/or peptides suspected of having affinity for the binding partner. The microcavities containing the cells displaying or secreting compounds having the highest binding affinity can be identified with an appropriate reporter system.

In an embodiment, the disclosure contemplates a method comprising identifying protein-carbohydrate interactions. Carbohydrates that are binding partner known to be involved in a disease condition (i.e., for example, an oligosaccharide, and liposaccharide, or a proteosaccharide) can be screen against a plurality of cells secreting or surface-displaying various lectins, proteins and/or peptides suspected of having affinity for the binding partner. The microcavities containing the cells displaying or secreting compounds having the highest binding affinity can be identified with an appropriate reporter system.

In an embodiment, the disclosed method is used to detect a protein analyte or a protein having a desired characteristic (e.g., fluorescence). The detection of a particular analyte protein can be performed directly in the cavities of the array. The biochemical sensing can be done using standard detection techniques including a sandwich immunoassay or similar binding or hybridizing reactions. For example, the disclosure is directed to a method for engineering a property of interest in a fluorescent protein. The property of interest may be at least one of an emission spectra or emission intensity, a Stokes shift, and an absorption spectra or absorption intensity. In one particular example, the method of the disclosure can be used to screen a library of cells expressing proteins having a particular fluorescent absorbance spectra, emission spectra and/or extinction coefficient. In one particular embodiment, the protein is a dimerization dependent orange fluorescent protein (ddOFP) having at least one of the mutations identified in FIG. 17

In certain embodiments, the disclosure provides methods and apparatus useful for conducting high throughput analysis of enzyme activity. In one aspect, the embodiments provide methods to determine the kinetics of enzymes added to the microcavity arrays. For example, genes encoding a plurality of enzyme variants are introduced into and expressed in cells added to the microcavity array. A substrate for an enzyme is also provided, wherein the activity of the enzymes in the microcavity can be monitored over time by detecting (either directly, or indirectly via coupled assays) either the formation of product or the depletion of substrate from each pore. In some embodiments, enzyme variants with particular kinetic properties are selected, extracted from the microcavity array, and isolated for subsequent analysis, expansion, and, optionally, further selection steps. Modulators of enzyme activity may be added, either before or during incubations in the microcavity, to apply selective pressure for a particular enzyme activity. Accordingly, embodiments of the disclosure are useful to identify enzyme variants that exhibit resistance to, or stimulation by, the modulators.

In one example, the disclosure is directed to a method for measuring enzyme kinetics for a member of a protein enzyme library produced by a library of cells having a plurality of genotypes for producing mutant forms of a protein enzyme. The method comprising loading a microcavity array with the library of cells and incubating the array in the presence of a substrate for the protein enzyme under conditions that allow for production of the enzyme of interest. The array may be imaged at selected intervals to provide a time resolved analysis of enzyme activity. The time periods may be selected in light of the enzyme and substrate system being analyzed. For example, time periods may be seconds, minutes or hours, and signal from one or more cavities of the array may be measured at any number of intervals; for example, 2, 3, 4, 5, 6, 7, 8, 9, 10, 15, 20, 40, 60, 80 or 100 intervals.

In a particular example, the enzyme is alkaline phosphatase (AP) and a modulator is inorganic phosphate, which inhibits the activity of AP. According to the method of the disclosure, a library of cells expressing AP variants can be screened by loading the cells into the array and screening microcavities for AP activity in the presence of inorganic phosphate.

An AP variant identified according the method of the disclosure has at least one of the following mutations: D101G, 116V, N145I, D294G, N197S, T148P, and S175R. In particular, the variant may be D101G, or may be one of I16V-N145I-D294G and N197S-T148P-S175R. In addition, the remainder of the AP variant may be at least 90, 91, 92, 93, 94, 95, 96, 97, 98, or 99 percent identical to wild-type AP. The D101 position is known to be important for positioning the R166 residue that coordinates the phosphate ion within the AP active site. As such, the D101G mutation uncovered in the method of the disclosure likely alters the positioning of R166 that lowers the affinity of the enzyme for inorganic phosphate.

In one embodiment, the analyte is a nucleic acid. For example, DNA or mRNA expression may be measured by any suitable method. For example, RNA expression is detected by enzymatic cleavage of specific structures (INVADER® assay, Third Wave Technologies; See, e.g., U.S. Pat. Nos. 5,846,717, 6,090,543; 6,001,567; 5,985,557; and 5,994,069; each of which is herein incorporated by reference). The INVADER® assay detects specific nucleic acid (e.g., RNA) sequences by using structure-specific enzymes to cleave a complex formed by the hybridization of overlapping oligonucleotide probes. In another embodiment, RNA (or corresponding cDNA) is detected by hybridization to an oligonucleotide probe. A variety of hybridization assays using a variety of technologies for hybridization and detection are available. (e.g., TAQMAN® assay, PE Biosystems, Foster City, Calif.; see, e.g., U.S. Pat. Nos. 5,962, 233 and 5,538,848, each of which is herein incorporated by reference). In addition, reverse-transcriptase PCR (RT-PCR) may be used to detect the expression of RNA. For example, quantitative reverse transcriptase PCR with standardized mixtures of competitive templates method are described in U.S. Pat. Nos. 5,639,606, 5,643,765, and 5,876,978 (each of which is herein incorporated by reference).

The detection disclosed herein may be used to isolate any types of biological cells, including, but not limited to, cell lines that express or produce proteins, carbohydrates, enzymes, peptides, hormones, receptors; other cell lines that produce antibodies; genetically engineered cells; and/or activated cells. Moreover, the disclosure may be used to screen for a variety of biological activities including, but not limited to, the expression of surface receptor proteins, enzyme production, and peptide production. Furthermore, the disclosure may be used to screen a variety of test agents to determine the effect of the test agents on the desired biological activity. Other types of cells desired to be isolated and screened, other types of biological activity desired to be detected, and specific test agents to be screened will be readily appreciated by one of skill in the art. The biological cell is a transformed biological cell. Transformation of cells can occur by any well-known methods, using any well-known vectors, such as for example a plasmid or virus. The biological cell may be a microbial, fungal, mammalian, insect or animal cell. The microbial cell may be bacterial cell such as an *E. coli* cell. In one embodiment, the animal cell includes a rare biochemical compound. In one embodiment, the rare biochemical compound is selected from the group comprising a protein, a peptide, a hormone, a nucleic acid, a carbohydrate. In another embodiment, the biological cell produces and/or expresses a fluorescent protein. In yet another embodiment, the biological cell produces a protein fused to a fluorescent protein (e.g. GFP).

Accordingly, the embodiments of the disclosure are directed to a method for screening a library of cells having a plurality of genotypes for a cell having a phenotype of interest for producing a molecule of interest. The method includes loading a microcavity array with the library of cells and incubating the array under conditions that allow for production of the molecule of interest. The array can be imaged it identify one or more cavities containing cells having the phenotype of interest. The contents of the cavities may be extracted by directing electromagnetic radiation from a pulsed diode laser at a radiation absorbing material associated with the cavity.

Figure 4:
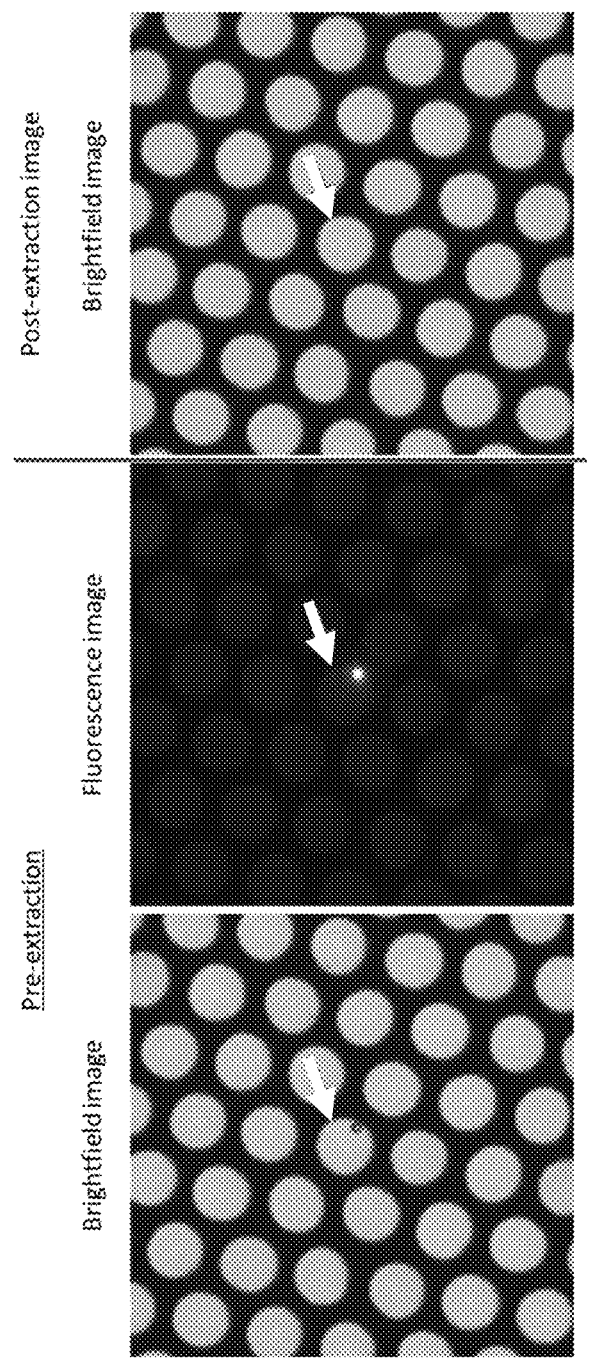
FIG. 4 and FIG. 5 show an example process of extraction of the contents from cavities of microcavity arrays using a laser focused on, and delivering electromagnetic radiation to, the interface between the sample and the wall of the microcavity.
Figure 5:
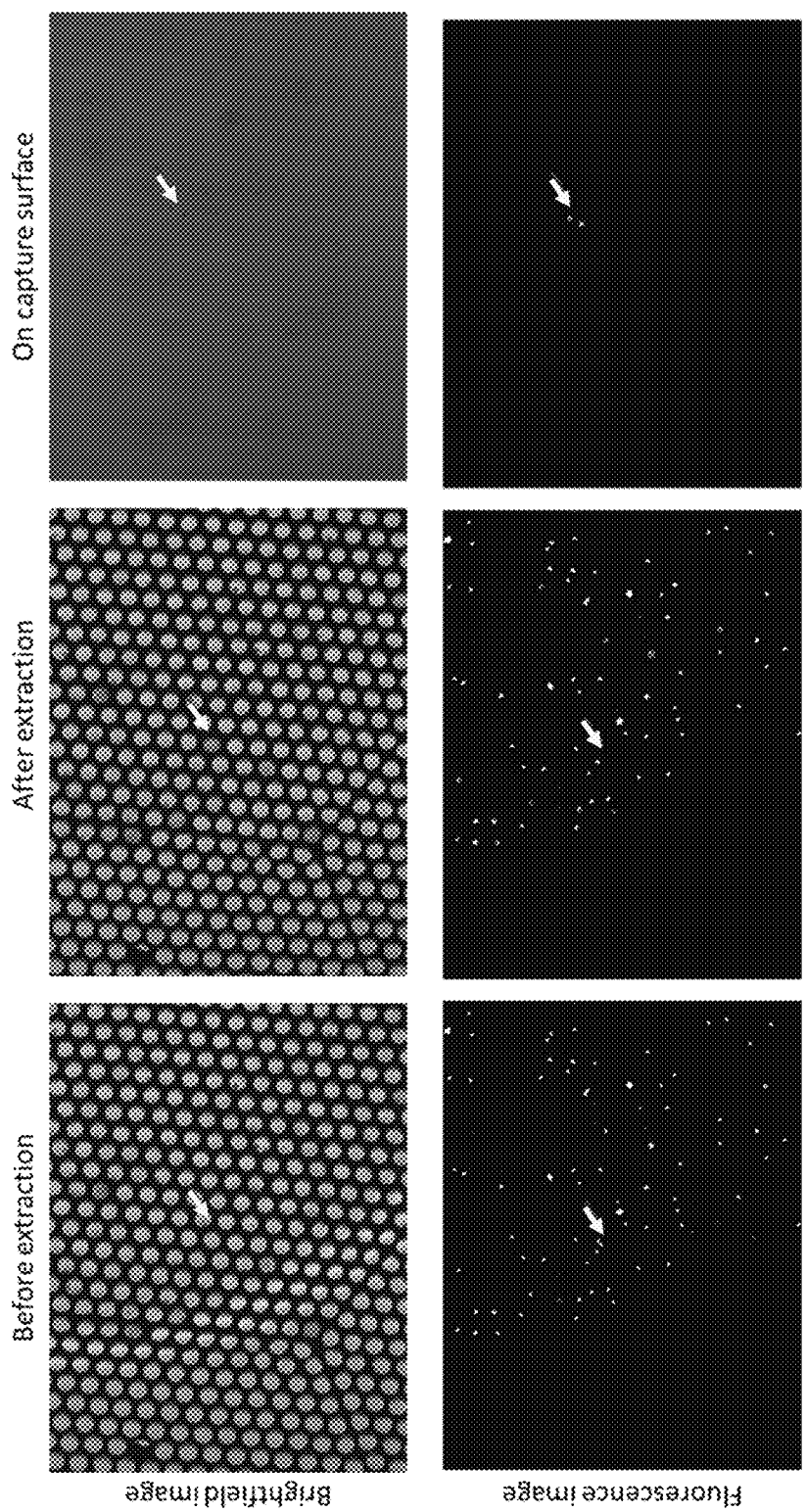

In some embodiments, the number of cells in the sample liquid results in a diverse population of cells in each cavity. Following extraction and expansion of the contents of a particular cavity, the resulting population can be screened in subsequent steps to identify particular cells of interest. FIGS. 4 and 5 show before and after fluorescence and Brightfield images of an example array before and after extraction of a cavity of the array. White arrows indicate the same cavities pre- and post-extraction.

As shown in FIG. 5, extraction of the cavity resulted in two cells of interest from a single cavity. In other embodiments, the number of cells in a sample liquid is less than the number of cavities in the array, resulting in the loading only one cell or less in each of the cavities. Accordingly, from the content of the cavity extracted in an initial screening with more than one cell per cavity, subsequent screening of the contents of the cavity following expansion of the contents of the cavity and loading at a low concentration on an array can identify single cells having a phenotype of interest from a large diverse population of cells.

In addition, the library may be enriched by (1) extracting DNA from the cells comprising a gene for the phenotype of interest, (2) amplifying the DNA under conditions to introduce random mutations in the gene; (3) creating a second generation library of cells comprising the amplified DNA, and (4) repeating steps identified above with the second generation library. During an initial screen of the library or in the enrichment process, multiple cells may be added to any particular cavity. Cell contents may be extracted and further analyzed or enriched in accordance with the method of the disclosure. Ultimately, having one cell per cavity allows for identification of a particular genotype. The extracting may discreetly directing electromagnetic radiation to the cavities having cells producing proteins having a phenotype of interest, wherein the directing of electromagnetic radiation to the cavities does not heat the liquid prior to extraction.

In various aspects of the method, the phenotype of interest is a cell surface binding agent. In another aspect, the phenotype of interest is a fluorescent protein that has at least one of an absorption or emission intensity of interest, an absorption or emission spectra of interest, and a stokes shift of interest. Moreover, the phenotype of interest may be the production of a protein having enzymatic activity, a protein having a lack of inhibition of enzyme activity, and a protein having activity in the presence of an inhibitor for the enzyme.

Certain embodiments of the disclosure provide methods and apparatus for growth of one or more biological elements. In some embodiments, a cell is introduced into a microcavity of an array in a culture medium suitable for growth. The array is then incubated under conditions that support growth of the cells, for example at suitable temperature, humidity, and atmospheric gas composition. In some embodiments, the surfaces of the microcavity array are treated to support growth of cells added to the array.

Particles

In various embodiments, the cavities of the arrays are loaded with particles as solid surfaces supporting binding reactions and/or as energy absorbing material that facilitates extracting of cavity contents. Suitable particles are readily commercially available and a wide variety of particles can be used according to the methods disclosed herein. In various embodiments, the particles are partially or fully opaque. In certain embodiments, the particles absorb electromagnetic radiation, for example the particles have an efficiency of absorbance of at least about 10 percent, for example, 25, 30, 35, 40, 45, 50, 55, 60, 65, 70, 75, 80, 85, 90, 95 or 100 percent.

In various embodiments, the size of the particles ranges from nanoscale to about one-third the size of the cross section of a cavity. For example, when a microcavity is about 20 microns in diameter, the particle can be about 0.01 to 7 microns in diameter. In other embodiments, the particle diameter ranges from about 0.01 microns to about 50 microns, depending on the size of the cavity used. In various embodiments, the particles range in size from about 0.1 to 15 microns, about 0.5 to 10 microns, and about 1 to about 5 microns. In certain embodiments, the particles comprise a metal or carbon. Non-limiting examples of suitable metals include gold, silver, and copper. Other metallic materials are suitable for use in binding and detection assays as is well known to those of skill in the art.

In one embodiment, the particles are magnetic such that magnetic force can be used to accumulate the particles at a surface of each reaction cavity, e.g., the meniscus of a micro-cavity as describe in US patent publication No. 2014/011690, which is incorporated by reference herein in its entirety.

In some aspects of the disclosure, the surface chemistry of the particles may be functionalized to provide for binding to sample components as is well known to those of skill in the art. For example, the particles are coupled with streptavidin, biotin, oligo(dT), protein A & G, tagged proteins, and/or any other linker polypeptides. The very high binding affinity of the streptavidin-biotin interaction is utilized in a vast number of applications. Streptavidin coated particles will bind biotinylated nucleic acids, antibodies or other biotinylated ligands and targets. Biotinylated antigens are also a useful example of reagents that could be attached to the particles for screening for analytes. In a specific embodiment, the particles are DYANABEAD® particles (Invitrogen, Carlsbad, Calif.) coupled to several different ligands. For example, oligo(dT), protein A & G, tagged proteins (His, FLAG), secondary antibodies, and/or streptavidin. (Part No. 112-05D, Invitrogen, Carlsbad, Calif.).

In some embodiments, particles having different magnetic permittivities can be used to provide independent control of the magnetic forces acting on the particles. In other embodiments, other properties of the particles can be used to expand the multiplexing capability of the assays done in each cavity. When added to a sample, particles bind to the desired target (cells, pathogenic microorganisms, nucleic acids, peptide, protein or protein complex etc). This interaction relies on the specific affinity of the ligand on the surface of the particles. Alternatively, the particles conjugated to substrate for an enzyme can be added to the sample, where the enzyme/analyte in the sample either quenches the ability of the substrate to fluoresce or activates the substrate to be fluorescent (e.g., enzyme mediated cleavage of the substrate).

Another embodiment uses magnetic particles having different shapes, densities, sizes, charges, magnetic permittivity, or optical coatings. This allows different probes (i.e., binding partners) to be put on the different particles and the particles could be probed separately by adjusting how and when the magnetic field or other force is applied. Sedimentation rates can also be used to separate the particles by size, shape and density and expand the multiplexing capability of the assays done in each cavity. In an example embodiment, the particles comprise superparamagnetic iron oxide-doped microbeads with an average diameter of about 1 μm, for instance about 100 nm to about 10 μm.

In certain embodiments, the particles are used to mix the content of the cavities. For example, magnetic particles are subjected to and alternating or intermittent magnetic field(s) during an incubation step. The movement and settling of the particles results in the mixing of the contents of the reaction cavity.

Any suitable binding partner with the requisite specificity for the form of molecule, e.g., a marker, to be detected can be used. If the molecule, e.g., a marker, has several different forms, various specificities of binding partners are possible. Suitable binding partners are known in the art and include antibodies, aptamers, lectins, and receptors. A useful and versatile type of binding partner is an antibody.

The method for detecting an analyte in a sample disclosed herein allows for the simultaneous testing of two or more different antigens per pore. Therefore, in some embodiments, simultaneous positive and negative screening can occur in the same pore. This screening design improves the selectivity of the initial hits. In certain embodiments, the second antigen tested can be a control antigen. Use of a control antigen is useful for normalizing biological element concentration across the various cavities in the array. A non-limiting example would be using a first antigen specific for an analyte of interest, and a second antigen that is non-specific for all proteins, such as an N- or C-terminal epitope tag. Therefore the results of cavities of interest can be quantified by comparing the signal to total protein concentration.

In some embodiments, the second antigen is associated with second particles that are different from the first particles. The particles can vary by least one of the following properties: shape, size, density, magnetic permittivity, charge, and optical coating. The second label can therefore associate with the second particles as a result of the presence or absence of a second analyte in the sample, and processed using motive forces as described below.

In another embodiment, the particles non-specifically bind sample components. For example, particles can be functionalized to non-specifically bind all protein in a sample, which allows for normalization of protein content between samples in an array.

Antibodies

The term "antibody," as used herein, is a broad term and is used in its ordinary sense, including, without limitation, to refer to naturally occurring antibodies as well as non-naturally occurring antibodies, including, for example, single chain antibodies, chimeric, bifunctional and humanized antibodies, as well as antigen-binding fragments thereof. It will be appreciated that the choice of epitope or region of the molecule to which the antibody is raised will determine its specificity, e.g., for various forms of the molecule, if present, or for total (e.g., all, or substantially all, of the molecule).

Methods for producing antibodies are well-established. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments that mimic antibodies can be prepared from genetic information by various procedures (Antibody Engineering: A Practical Approach (Borrebaeck, C., ed.), 1995, Oxford University Press, Oxford; J. Immunol. 149, 3914-3920 (1992)). Monoclonal and polyclonal antibodies to molecules, e.g., proteins, and markers also commercially available (R and D Systems, Minneapolis, Minn.; HyTest Ltd., Turk, Finland; Abcam Inc., Cambridge, Mass., USA, Life Diagnostics, Inc., West Chester, Pa., USA; Fitzgerald Industries International, Inc., Concord, Mass., USA; BiosPacific, Emeryville, Calif.).

In some embodiments, the antibody is a polyclonal antibody. In other embodiments, the antibody is a monoclonal antibody.

Capture binding partners and detection binding partner pairs, e.g., capture and detection antibody pairs, can be used in embodiments of the disclosure. Thus, in some embodiments, a heterogeneous assay protocol is used in which, typically, two binding partners, e.g., two antibodies, are used. One binding partner is a capture partner, usually immobilized on a particle, and the other binding partner is a detection binding partner, typically with a detectable label attached. Such antibody pairs are available from several commercial sources, such as BiosPacific, Emeryville, Calif. Antibody pairs can also be designed and prepared by methods well-known in the art. In a particular embodiment, the antibody is biotinylated or biotin labelled In one embodiment, there is a second imaging component that binds all members of the analyte of interest non-specifically. Therefore this signal can be read to normalize the quantity of fluorescence from cavity to pore. One example is an antibody that will bind all proteins at an N- or C-terminal epitope tag.

Labels

Several strategies that can be used for labeling binding partners to enable their detection or discrimination in a mixture of particles are well known in the art. The labels may be attached by any known means, including methods that utilize non-specific or specific interactions. In addition, labeling can be accomplished directly or through binding partners.

Emission, e.g., fluorescence, from the moiety should be sufficient to allow detection using the detectors as described herein. Generally, the compositions and methods of the disclosure utilize highly fluorescent moieties, e.g., a moiety capable of emitting electromagnetic radiation when stimulated by an electromagnetic radiation source at the excitation wavelength of the moiety. Several moieties are suitable for the compositions and methods of the disclosure.

Labels activatable by energy other than electromagnetic radiation are also useful in the disclosure. Such labels can be activated by, for example, electricity, heat or chemical reaction (e.g., chemiluminescent labels). Also, a number of enzymatically activated labels are well known to those in the art.

Typically, the fluorescence of the moiety involves a combination of quantum efficiency and lack of photobleaching sufficient that the moiety is detectable above background levels in the disclosed detectors, with the consistency necessary for the desired limit of detection, accuracy, and precision of the assay.

Furthermore, the moiety has properties that are consistent with its use in the assay of choice. In some embodiments, the assay is an immunoassay, where the fluorescent moiety is attached to an antibody; the moiety must have properties such that it does not aggregate with other antibodies or proteins, or experiences no more aggregation than is consistent with the required accuracy and precision of the assay. In some embodiments, fluorescent moieties dye molecules that have a combination of 1) high absorption coefficient; 2) high quantum yield; 3) high photostability (low photobleaching); and 4) compatibility with labeling the molecule of interest (e.g., protein) so that it may be analyzed using the analyzers and systems of the disclosure (e.g., does not cause precipitation of the protein of interest, or precipitation of a protein to which the moiety has been attached).

A fluorescent moiety may comprise a single entity (a Quantum Dot or fluorescent molecule) or a plurality of entities (e.g., a plurality of fluorescent molecules). It will be appreciated that when "moiety," as that term is used herein, refers to a group of fluorescent entities, e.g., a plurality of fluorescent dye molecules, each individual entity may be attached to the binding partner separately or the entities may be attached together, as long as the entities as a group provide sufficient fluorescence to be detected.

In some embodiments, the fluorescent dye molecules comprise at least one substituted indolium ring system in which the substituent on the 3-carbon of the indolium ring contains a chemically reactive group or a conjugated substance. Examples include Alexa Fluor molecules.

In some embodiments, the labels comprise a first type and a second type of label, such as two different ALEXA FLUOR® dyes (Invitrogen), where the first type and second type of dye molecules have different emission spectra.

A non-inclusive list of useful fluorescent entities for use in the fluorescent moieties includes: ALEXA FLUOR® 488, ALEXA FLUOR® 532, ALEXA FLUOR® 555, ALEXA FLUOR® 647, ALEXA FLUOR® 700, ALEXA FLUOR® 750, Fluorescein, B-phycoerythrin, allophycocyanin, PBXL-3, Atto 590 and Qdot 605.

Labels may be attached to the particles or binding partners by any method known in the art, including, absorption, covalent binding, biotin/streptavidin or other binding pairs. In addition, the label may be attached through a linker. In some embodiments, the label is cleaved by the analyte, thereby releasing the label from the particle. Alternatively, the analyte may prevent cleavage of the linker.

EXAMPLES

Example 1

Microarray Single Cell Analysis and Laser Extraction

The overall concept and workflow of a microarray of one aspect of the disclosure (referred to herein as "µSCALE") is described in FIG. 6A-6D. FIG. 6A shows platform workflow. 1) A library of protein variants, expressed in bacteria or yeast cells, is mixed with opaque magnetic beads. 2) The mixture is pipetted into the array at a concentration that results in a mean single-cell occupancy within the microcavities. A variety of biochemical assays are carried out, with or without cell growth, using fluorescence as a readout. 3) The array is imaged via fluorescent microscopy. 4) The fluorescent intensity of each microcavity is quantified, and desired clones are isolated from the array with a laser-based extraction method, as single cells or as a bulk pool. 5) The extracted cells are cultured in liquid or on solid media. 6) Cells are lysed and the plasmid is recovered for characterization and/or generation of a new library for additional rounds of evolution. FIG. 6B shows a representation of a laser-based extraction method. To extract a microcavity of interest, a laser is positioned and pulsed, disrupting the surface tension of the microcavity and emptying its contents onto a capture surface below the array. FIG. 6C shows the extraction of two neighboring microcavities loaded with fluorescent particles. In the left panel, the first and second microcavities to be extracted are outlined with a dark or light circle respectively. The second panel demonstrates successful extraction of the first microcavity without disturbing neighboring microcavities (indicated by a dark arrow). The third panel shows the isolated particle on the capture surface below the array. The final panel demonstrates the second successful microcavity extraction (indicated by a light arrow). FIG. 6D shows a representation of three diverse assays performed in the µSCALE platform. Left, Binding interactions of a yeast surface-displayed scFv library pre-stained with fluorescent antibodies. Middle, Fluorescent protein variants expressed in E. coli clones cultured within the microcavities. Right, Real-time kinetic measurements on a library of yeast surface-displayed enzyme variants that convert a substrate to a fluorescent product. A dense glass-substrate array of millions of spatially-segregated fabricated microcavities of high-aspect ratio (1 mm thick, 10 µm or 20 µm in diameter) is loaded with a cell suspension mixed with magnetic particles. The suspension is applied to the top of the array and fills the microcavities through capillary action. The microcavity array is unsealed on the bottom; the liquid sample is held in place by surface tension. The passive nature of the filling process results in a uniform meniscus level across the entire array. Among other advantages, this uniformity, coupled with gravitational sedimentation of the loaded cells simplifies the establishment of the imaging focus plane without the need for autofocus.

Each microcavity can be loaded with a single cell or particle following Poisson distribution theory as shown in FIG. 1. Fluorescent beads were loaded into the array at three concentrations corresponding to means of 3, 1, and 1/3 particles per cavity ($\lambda=3,1,1/3$). The contents of approximately 25,000 cavities were counted, and the cumulative distribution functions (CDF) for each condition are plotted as red lines. Maximum likelihood fits to the Poisson distribution with $\lambda=0.79$, 0.43, and 0.15 are overlaid above the data as black lines. While the distributions closely follow Poisson statistics, the observed and expected means differ by 2-3 fold. This difference likely arises due to the high aspect ratio of the microcavities; some particles may not travel all the way into the imaging plane.

Figure 7:
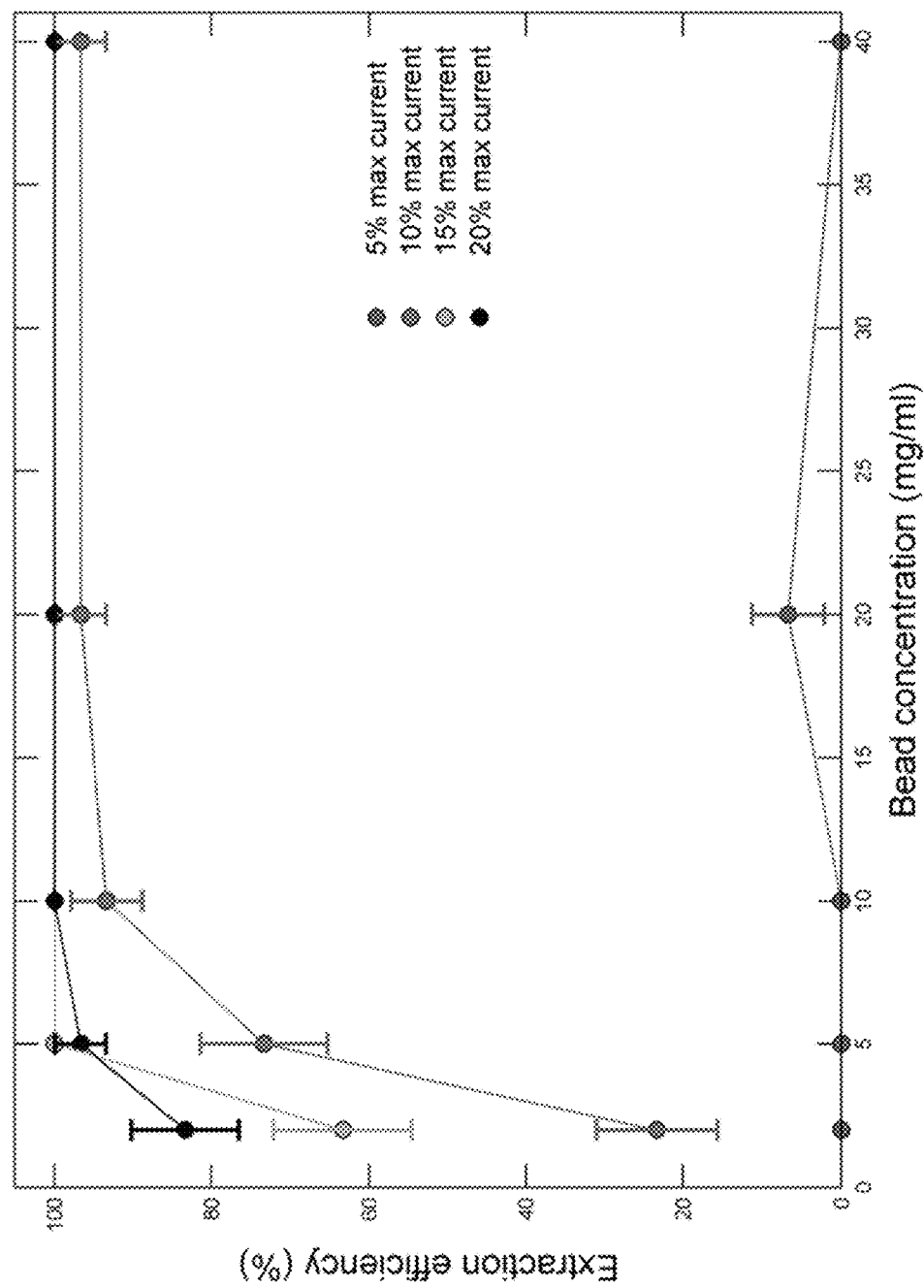
FIG. 7 shows the results of an experiment to show the extraction efficiency at different laser powers and bead concentrations using an example system of disclosure.

A pulsed UV laser interacts with the magnetic particles to disrupt the surface tension within a single microcavity without affecting its nearest neighbors (FIGS. 6B and 6C). Laser extraction empties the contents of a microcavity onto a capture surface below the array, which can be imaged to confirm extraction and to perform additional morphological studies. To refine the extraction technique, laser intensity is varied and magnetic bead concentrations are titrated to establish a range of conditions that achieved complete extraction efficiency as shown in FIG. 7. For each extraction, the Triton cutting laser of the laser capture microdissection (LCM) microscope was pulsed for 10 msec at a range of different laser powers, ranging from 5%-20% of the maximum current as set by the laser manufacturer. 30 extractions were performed for each condition. Error bars represent the binomial sampling error for each condition.

Viability of cells extracted in the following experiments is shown in Table 4.

TABLE 4

| Experiment | | Extracted pores | Observed growth | Viability |
|---|---|---|---|---|
| | Mock library-S. cerevisiae | | | |
| Yeast | 1:1 | 20 | 14 | 70% |
| | 1:10 | 20 | 12 | 60% |

TABLE 4-continued

|  | Experiment | Extracted pores | Observed growth | Viability |
|---|---|---|---|---|
|  | 1:100 | 20 | 10 | 50% |
|  | 1:1000 | 20 | 11 | 55% |
|  | 1:10000 | 20 | 9 | 45% |
|  | 1:100000 | 5 | 2 | 40% |
|  | scFv library-*S. cerevisiae* | | | |
|  | Sort 2 | 15 | 12 | 80% |
|  | AP library-*S. cerevisiae* | | | |
|  | Sort 1 | 15 | 12 | 80% |
|  |  |  | Mean | 61% ± 14% |
|  | FP library-*E. coli* | | | |
| E.Coli | Sort 1 & 2 | 24 | 24 | 100% |
|  | Sort 3 | 10 | 10 | 100% |
|  |  |  | Mean | 100% ± 0% |
|  | Extraction survival test-*b. subtillis* | | | |
| B. Subtilis | Survival | 20 | 20 | 100% |
|  |  |  | Mean | 100% ± 0% |

Methods may be developed to perform a variety of biochemical assays within the cavities of the array. For example, cells expressing a protein of interest are loaded into a microcavity array, which may be kept in a humid environment to permit time-resolved experimental measurements or expansion of cells over a period of days.

Following established guidelines for quantitative widefield microscopy, the inter-capillary variability in fluorescence signals detected from the array was measured and found it to be comparable to other high-throughput methods. Fluorescent beads (Sphero, FP-4052-2, Spherotech) were analyzed on both μSCALE and a Guava easyCyte flow cytometer (Millipore) (n=10,000). For μSCALE measurements, the fluorescent beads were loaded into a 20 μm microcavity array without magnetic particles. Both populations were normalized by the mean of their respective distributions. The coefficients of variation of the bead fluorescence analyzed by flow cytometry and by μSCALE were 0.15 and 0.14, respectively. To cover the entire microcavity array, the array is imaged at multiple positions and at multiple wavelengths at a rate of approximately 10,000 microcavities per second. The resulting images are analyzed using standard image processing functions. Because cells are imaged at high resolution, promising candidates can be distinguished from cell debris and other false fluorescence signals via quantified metrics (size, roundness, and fluorescence intensity) or by visual inspection.

The microcavities are imaged using a high numerical aperture microscope objective illuminated using a band-pass filtered high intensity arc lamp in an epi-illumination configuration. Fluorescent emission is detected through a high pass filter using a high-sensitivity, cooled CCD camera. An algorithm was developed to image and analyze fluorescence emissions at multiple wavelengths, at a rate of approximately 10,000 microcavities per second. Single cells of interest can then be recovered by laser extraction (termed single-cell extraction), as described herein, or bulk selection methods can be employed using user-chosen criteria to designate a cell population to be extracted (termed pooled extraction).

Figure 8:
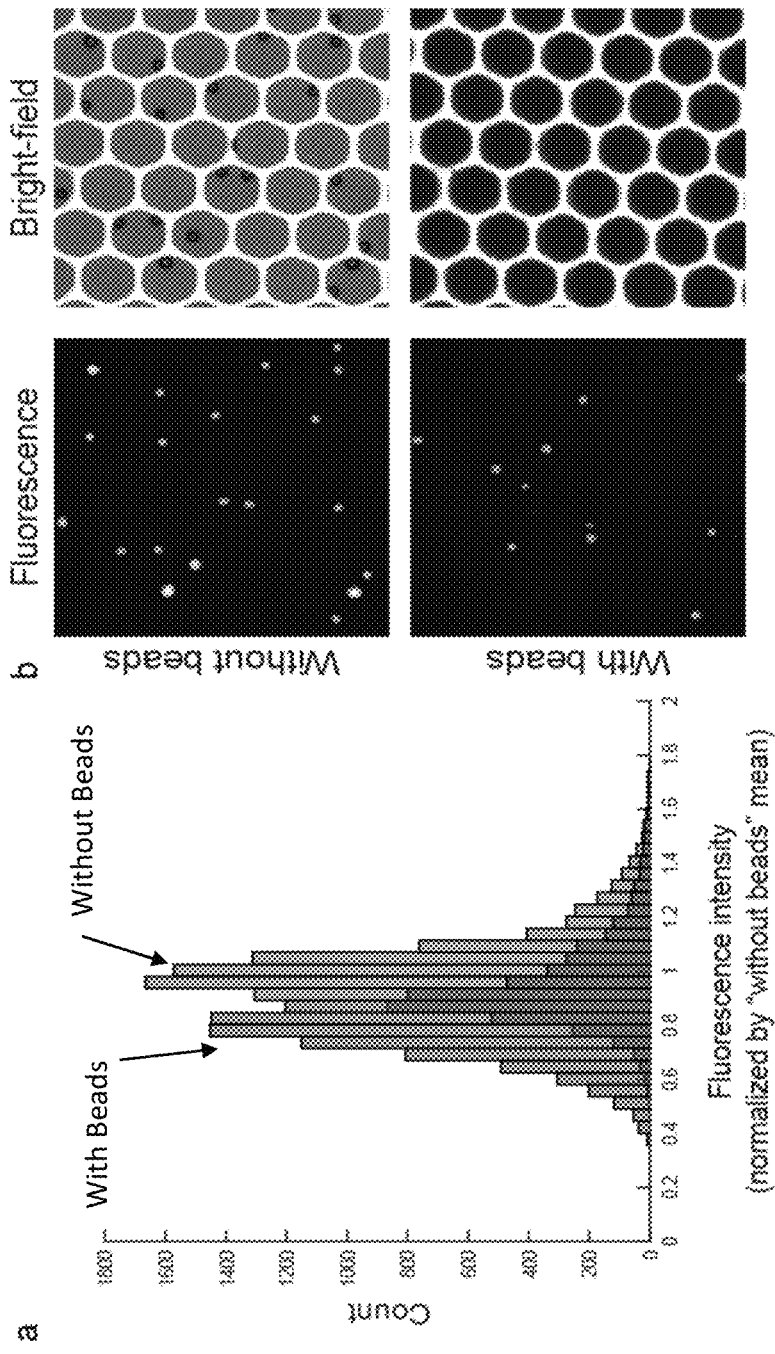
FIG. 8 shows the effect of magnetic beads on fluorescence measurements in an example system and method of the disclosure.

Impact of microparticles on fluorescence intensity. Magnetic microparticles may be opaque and impart a brownish color to the cell suspensions. To determine the impact of magnetic beads on fluorescence intensity and bright-field-imaging, fluorescent beads (Sphero, FP-4052-2, Spherotech) were analyzed on μSCALE with and without the presence of the magnetic particles used for extraction (n=10,000). As shown in FIG. 8, panel a, the mean of the normalized "with beads" population is 0.83, demonstrating that the magnetic beads partially occlude the fluorescence intensity of the microcavities. The coefficients of variation of the fluorescent bead distributions with and without magnetic particles are 0.2 and 0.14, respectively, demonstrating that the use of magnetic beads for extraction does not significantly increase the variability of fluorescence measurements on μSCALE. FIG. 8, panel b, shows that the presence of magnetic beads reduces the fluorescence intensity and obscures the bright-field images. The addition of these microparticles uniformly occludes the fluorescence signal to a limited degree and prevents bright-field imaging of the contents of the microcavity.

Figure 9:
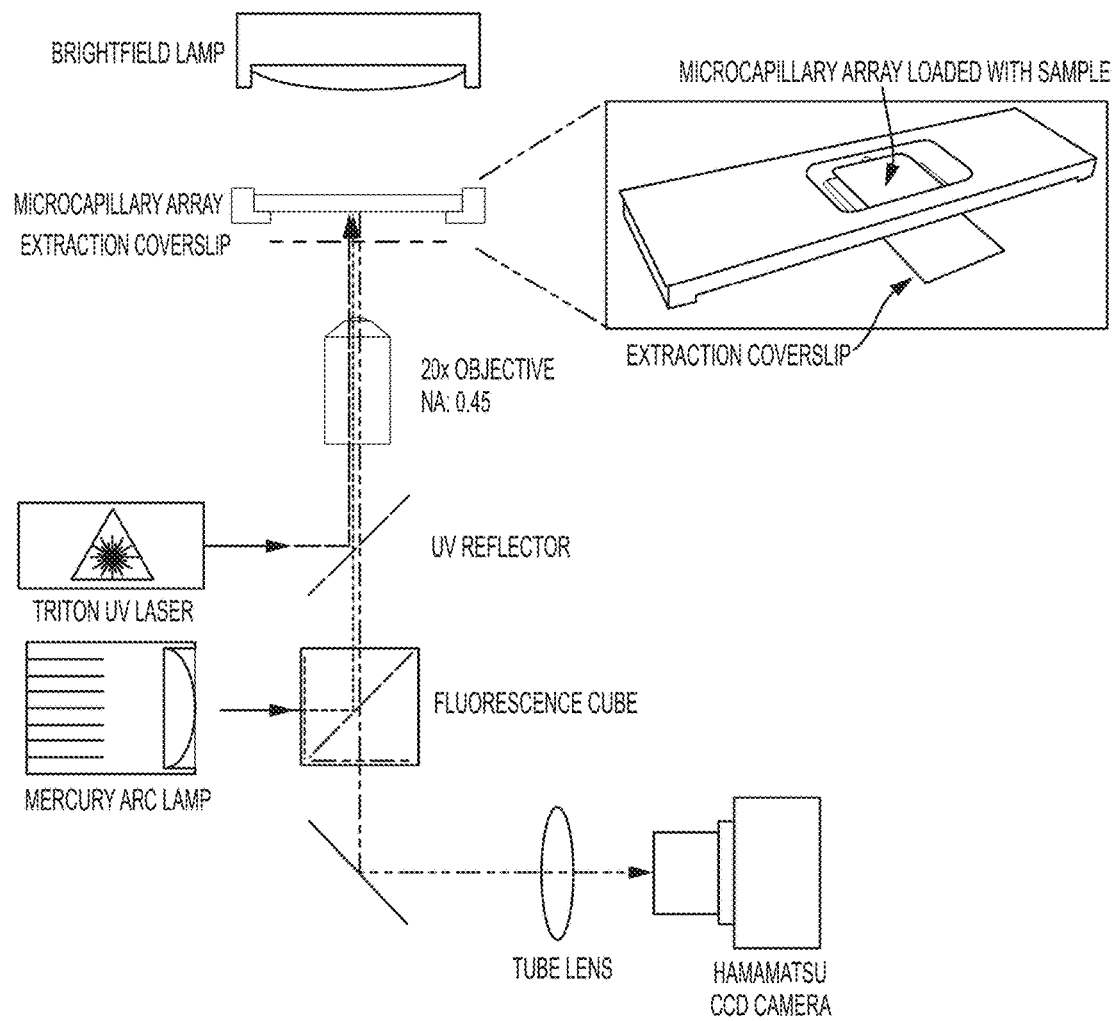
FIG. 9 shows an example of system of the disclosure.

FIG. 9 shows an example platform incorporated around an automated inverted fluorescence microscope and electromagnetic radiation source, such as a UV laser or diode laser. An example instrument has both bright-field and fluorescence imaging capabilities. A 3-axis stage allows for rapid alignment of the laser with the desired microcavity. A similar configuration could be recreated with a wide range of automated inverted microscopes with appropriate fluorescence illumination system and laser source. Sample (brown color imparted by beads indicated by black arrow) is loaded into the microcavity array and placed into a holder, which is then analyzed using the instrument. An extraction coverslip is placed below the holder for sample recovery.

Microarray experiments may be performed with a Veritas laser capture microdissection (LCM) microscope (Arcturus) adapted with hardware and software modifications to enable microcavity screening applications. In one embodiment, the system contains an inverted fluorescence microscope with motorized stage and the Triton UV laser (diode-pumped Q-switched Nd:YLF laser, Spectra-Physics). The laser system uses a wavelength of 349 nm, a focused beam diameter of 5 μm, and a pulse duration of 20 ns. For fluorescence imaging, an X-CITE® 120 illumination system (EXFO Photonic Solutions Inc.) was used, along with the XF410 QMAX FITC and the XF406 QMAX red filter set (Omega Optical). All images were acquired with a 20× Plan Fluorite objective (numerical aperture: 0.45, CFI, WD: 7.4, Nikon) by an ORCA-R2 cooled CCD camera (Hamamatsu).

Software to control the LCM microscope and laser, and for automatic image-quantification of microcavities was developed. The software suite automatically scans over the array, acquiring multi-color fluorescent and bright-field images of every microcavity. To quantify each microcavity, image segmentation was performed using Otsu's method to threshold the chosen color image, creating a binary mask. This binary mask was used to quantify the fluorescence intensity at each region of interest. Once desired microcavities are identified, the software allows the user to retrieve cells in two different modalities: single-cell sorting and pooled sorting. In single-cell sorting, the software returns to a selected microcavity, allowing the user to perform further examination and to extract the desired cell onto a sterile capture surface, resulting in a segregated clonal population. In pooled sorting, a sort gate is established, and the software automatically extracts the contents of arbitrarily specified microcavities onto a single capture surface, creating a population of enriched cells.

Microcavity array preparation, loading, and extraction. Microcavity arrays from INCOM, Inc. (10 and 20 μm cavity diameter, 1 mm thick) were sterilized in ethanol and dried. The loading-side of the arrays were corona treated was a Tesla coil (BD-20AC Electro-Technic Products) for 1 minute to generate a hydrophilic surface, which facilitates loading. On the loading side a piece of clear packaging tape was applied and flattened to the top of the openings of the cavities. The array was inverted and RAIN-X® water repellent was applied with a disposable towelette by applying a small amount of the water repellent to the towelette and allowing it to air dry for one minute. The towelette was then used to polish the opening of the cavities on the surface of the array. The adhesive tape was removed and the Tesla treatment was reapplied to the loading side of the array.

To achieve the maximum fraction of wells containing single cells, cell suspensions were diluted prior to loading according to Poisson statistics (~3,200 cells/µL in 20 µm arrays and ~12,800 cells/µL in 10 µm arrays). Specific loading conditions for each protein engineering application are described in subsequent Examples. Briefly, cell suspensions were mixed with magnetic beads (Life Technologies, 37002D) to a final bead concentration of 10 mg/ml and pipetted into the arrays. A ~2 mm slab of 1% weight/volume agarose was overlaid on the array to prevent evaporation. The Triton UV laser in the LCM system was used to extract the contents of desired cavities. As shown in FIG. 7 the laser power was adjusted so that the extraction efficiency of a single pulse is 100%. In the example embodiment described here, extraction parameters comprise the following: the laser operates for 18±2 ms (n=5 measurements), delivering a train of pulses at 2.5 kHz with a total energy of approximately 100 µJ. The cavity contents were extracted onto a glass coverslip, which was then placed in yeast or bacterial growth media (liquid medium or agar plates) to propagate the extracted cells. After each experiment, the arrays were cleaned by removing their contents with a strong stream of distilled water, followed by brief sonication in 1 M NaOH, and storage in 100% ethanol.

Example 2

High-throughput Screening of Protein Binding Interactions

Axl Ig1 mock library screening. DNA encoding human Axl Ig1 (amino acids $Ala_{19}$-$Pro_{131}$) and non-binding Axl variant (E59R, T77R) were cloned into the pCT yeast display plasmid between NheI and BamHI restriction sites (Kariolis, M. S. et al., *Nat. Chem. Biol.* 1-10 (2014)). Plasmid DNA was transformed into the *S. cerevisiae* strain EBY100 by electroporation for yeast surface display studies. Soluble Gas6 was recombinantly expressed in human embryonic kidney (HEK) cells using FreeStyle Max 293 Expression System (Invitrogen) and purified as previously described (Kariolis, M. S. et al., *Nat. Chem. Biol.* 1-10 (2014)). The yeast surface-displayed naïve scFv library (~7×10$^8$ variants) was previously described (Deventer, J. A. Van & Wittrup, K. D., *Yeast Surface Display for Antibody Isolation: Library Construction, Library Screening, and Affinity Maturation.* 1131, 151-181 (Humana Press, 2014). All yeast cells harboring the pCT display plasmid were grown in selective media and induced as previously described (Chao, G. et al., *Nat. Protoc.* 1, 755-68 (2006)).

For the Axl Ig1 mock libraries, induced yeast cells displaying wild-type and the non-binding Axl variant were mixed at defined cell ratios of 1 wild-type:10 non-binding, 1:100, 1:1,000, 1:10,000 and 1:100,000. Approximately (3-6×10$^6$) yeast cells (depending on the mock library) were incubated at room temperature for 6 hours with 1 nM purified growth arrest specific 6 (Gas6) in phosphate-buffered saline with 1 mg/ml BSA (PBSA). After incubation with Gas6, yeast were washed and resuspended in PBSA with a 1:250 dilution of chicken anti-c-Myc antibody (250; Life Technologies, A21281) for 45 min at 4° C. To detect Gas6 binding, yeast were washed and resuspended in PBSA with a 1:100 dilution of mouse anti-His IgG Hilyte Fluor 555 (Anaspec, 61250-H555) for 45 min at 4° C. To enhance the binding signal, yeast were washed and resuspended in PBSA, and a 1:100 dilution of goat anti-mouse IgG Hilyte Fluor 555 (Anaspec, AS-28175-05-H555) was subsequently added for 30 min at 4° C. Finally, to detect c-Myc expression, yeast were washed and resuspended in PBSA with a 1:100 dilution of goat anti-chicken IgG Alexa Fluor 488 (Life Technologies, A11039) for 30 min at 4° C. Labeled yeast were diluted to ~12,800 cells/µL, loaded on a 10 µm array, and analyzed for Gas6 binding with 475/40 nm excitation/510 nm long pass emission filters and for c-Myc cell surface expression with 525/45 nm excitation/565 nm long pass emission filters. Wild-type yeast or the non-binding variant were extracted via single-cell sorting and cultured on SD-CAA agar plates. To identify the extracted cells, plasmid DNA was recovered using a Zymoprep kit (Zymo Research Corporation), amplified by PCR, and sequenced by Sanger sequencing (Sequetech).

Table 5 shows enrichment ratios from mock libraries composed of wild-type (WT) and non-binding Axl clones. A series of mock library extractions were performed to quantify the efficiency of sorting. Enrichment ratio is defined as:

$$\eta = \frac{N_{+,1}}{N_{+,1} + N_{-,1}} \bigg/ \frac{N_{+,0}}{N_{+,0} + N_{-,0}}$$

where η is enrichment ratio, $N_{+,0}$ is the initial number of wild-type cells, $N_{+,1}$ is the number of wild-type cells after sorting, and $N_{-,0}$ and $N_{-,1}$ are the equivalent values for non-binding cells, respectively.

TABLE 5

Figure 11:
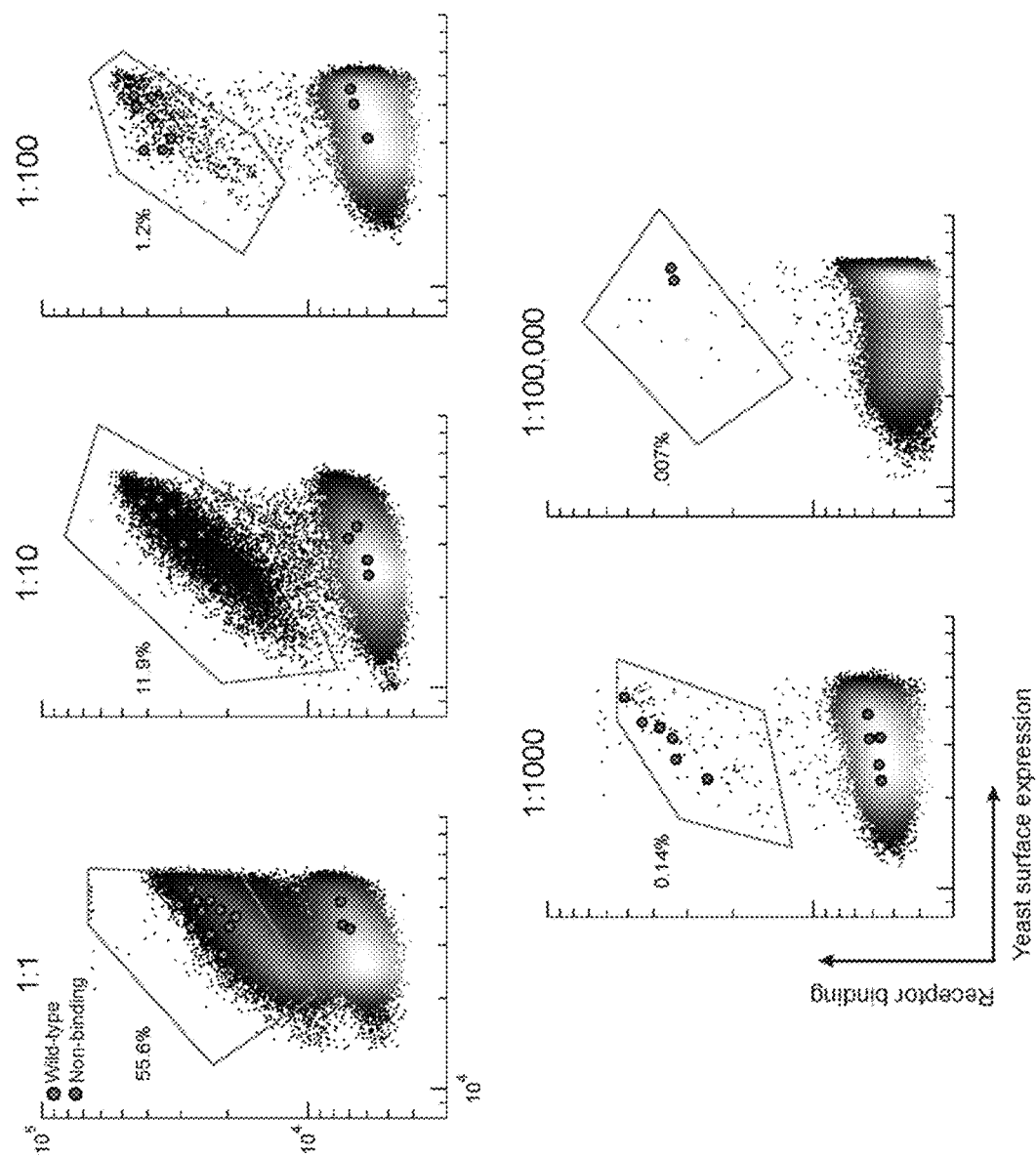
FIG. 11 shows scatter plots from mock library screens using example systems and methods of the disclosure.

| Initial Ratio | | Post-sort | | |
|---|---|---|---|---|
| WT | Non-binding | WT | Non-binding | Enrichment Ratio |
| 1 | 1 | 11 | 0 | 2 |
| 1 | 10 | 8 | 0 | 11 |
| 1 | 100 | 7 | 0 | 101 |
| 1 | 1,000 | 5 | 1 | 834 |
| 1 | 10,000 | 4 | 1 | 8,001 |
| 1 | 100,000 | 2 | 0 | 100,001 |

µSCALE distinguished yeast displaying either a wild-type or non-binding Axl receptor domain on their surface (Kariolis, M. S. et al., *Nat. Chem. Biol.* 10, 977-83 (2014)). FIG. 10A shows two-parameter scatter plots (left), where each dot represents a microcavity, and microscope images (right) of the wild-type Axl population (R) and the non-binding Axl variant population (B). Mock libraries of yeast-displayed Axl variants in ratios spanning 1:10 to 1:100,000 wild-type: non-binding clones were created and screened. Yeast were analyzed by two-color fluorescence analysis for Axl expression (as measured by antibodies against a C-terminal c-Myc epitope tag) and Gas6 binding (measured using an antibody against a hexahistidine tag on Gas6). For each mock library, several individual yeast cells exhibiting the predicted fluorescence intensity for cells expressing wild-type Axl or the non-binding Axl variant were extracted from the array, cultured, and verified by DNA recovery and sequencing. FIG. 10B shows a scatter plot from a representative mock library screen (ratio of wild-type:non-binding variant=1:10, 000). Extracted cavities identified as wild-type Axl (grey outlined dots) and non-binding Axl variants (black dots). FIG. 11 shows ratios of Axl wild-type:non-binding are presented for 1:1 (a), 1:10 (b), 1:100 (c), 1:1,000 (d), 1:10,000 (e), and 1:100,000 (f). The extracted cavities are indicated as red dots (identified as wild-type) and blue dots (identified as non-binding mutant). All receptor-binding (wild-type) extracts fall within the gated regions of the plots, and all but one non-binding mutant falls outside of the gated region (the single gated non-binder is indicated by an arrow in the lower left panel (1:1000 wild-type:non-binding ratio))

Across the six mock libraries, 37 out of 39 extractions were correctly identified as wild-type Axl, achieving an enrichment ratio of 100,001 in the most stringent condition (Table 4), a value that compares favorably against emulsion-based screening methods (See e.g. Zinchenko, A. et al., *Anal. Chem.* 86, 2526-33 (2014); Fischlechner, M. et al., *Nat. Chem.* 6, 791-796 (2014)).

Additionally, all 19 extractions selected as non-binders were identified as non-binding Axl variants. Thus, these mock library screens validate the ability of µSCALE to differentiate cells expressing ligand-binding protein variants, in particular for rare functional clones within a large population of non-functional clones.

scFv naïve library screening. The µSCALE platform was applied to screen a naïve library of yeast-displayed single-chain variable fragments (scFvs) to identify a variant that binds to Gas6 with high affinity. The yeast displayed scFv library was grown and induced for expression as previously described (Deventer, J. A. Van & Wittrup, K. D., *Yeast Surface Display for Antibody Isolation: Library Construction, Library Screening, and Affinity Maturation.* 1131, 151-181 (Humana Press, 2014). The library was subjected to two rounds of magnetic-activated cell sorting (MACS) to reduce theoretical diversity prior to µSCALE screening: a negative selection for cells that did not bind His-tag Isolation beads (Dynabeads®, 10103D, Life Technologies) and a positive selection for cells that bind Gas6-coated magnetic beads. Both sorts were performed according to manufacturer's instructions (Dynabeads® His-Tag Isolation & Pulldown protocol) and modeled after sorts previously described (Chao, G. et al., *Nat. Protoc.* 1, 755-68 (2006)). Gas6-coated magnetic beads (4 mg) were prepared by incubating Dynabeads® with a saturating amount of His-tagged Gas6 on a rotator for 2 hours at 4° C. These beads were washed using a magnetic holder (MPC-S, Dynal) with Binding/Wash Buffer (50 mM sodium phosphate (pH 8.0), 300 mM NaCl, and 0.01% Tween-20 in water) to remove unconjugated Gas6. For sort 1, $8 \times 10^9$ yeast cells were washed with Pull-down Buffer (3.25 mM sodium phosphate (pH 7.4), 70 mM NaCl, and 0.01% Tween-20 in water) and incubated with non-coated His-tag Dynabeads® in Pull-down Buffer for 2 hours at 4° C. After incubation, cells and beads were placed in a magnetic holder and unbound cells were collected; these non-binding yeast were transferred to fresh tubes and incubated with the prepared Gas6-coated beads for 2 hours incubation at 4° C. Using the magnetic holder, the yeast and beads were washed several times with Binding/Wash Buffer. Gas6-bound yeast cells were eluted from the magnetic beads with His-Elution Buffer (150 mM imidazole, 25 mM sodium phosphate (pH 8.0), 150 mM NaCl, and 0.005% Tween-20 in water) and grown in SD-CAA. Using this protocol, MACS reduced the library to $\sim 2 \times 10^6$ variants, which corresponds to 0.4% of the original library size.

µSCALE was used for two sequential screening rounds of the MACS-reduced scFv library. Yeast were incubated at room temperature for 2 hours in PBSA containing 33 nM Gas6 (sort 1) or 10 nM Gas6 (sort 2). Following incubation with Gas6, cells were stained in PBSA containing a 1:250 dilution of chicken anti-c-Myc antibody (Life Technologies, A21281) for 30 min at 4° C. Cells were stained in PBSA containing a 1:100 dilution of mouse anti-His Tag IgG Hilyte Fluor 488 (Anaspec, 61250-H488) for 30 min at 4° C. Finally, secondary labeling was performed in PBSA with 1:100 dilution of both goat anti-mouse IgG Alexa Fluor 488 (Life Technologies, A11001) and goat anti-chicken IgG Alexa Fluor 555 (Life Technologies, A21437) for 30 min at 4° C. Labeled yeast were diluted to ~12,800 cells/4 and loaded on a 10 µm array and analyzed for Gas6 binding using excitation/emission parameters described above. For µSCALE round 1, 143 cavities with the highest Gas6 binding/c-Myc expression ratio were auto-extracted within a single pool, creating a population enriched for binding affinity to Gas6. In µSCALE round 2, the top 15 cavities were extracted via single-cell sorting. After round 2, plasmid DNA was recovered using a Zymoprep kit (Zymo Research Corporation), PCR amplified, and sequenced (Sequetech).

The Gas6 binding affinity of the resulting scFv clone was measured by incubating $10^5$ induced yeast cells with varying concentrations of soluble Gas6 in $PBSA_{200}$ (0.1% BSA+200 mM NaCl in PBS) for 2 hours at room temperature. Cells were stained in $PBSA_{200}$ containing a 1:250 dilution of chicken anti-c-Myc antibody (Life Technologies, A21281) for 15 min at 4° C. Secondary antibody labeling was carried out in $PBSA_{200}$ containing a 1:100 dilution of mouse anti-His Tag IgG Hilyte Fluor 488 (Anaspec, 61250-H488) and goat anti-chicken IgY PE (Santa Cruz Biotechnology, sc-3730) for 30 min at 4° C. Binding and expression signals of the labeled cells were measured by flow cytometry (FACS Calibur, BD Biosciences). The error for the reported $K_D$ corresponds to a 1-σ (68%) confidence interval for the estimated binding affinity, and was calculated with the parametric bootstrap method using data from three independent experiments for each fit point.

Figure 12:
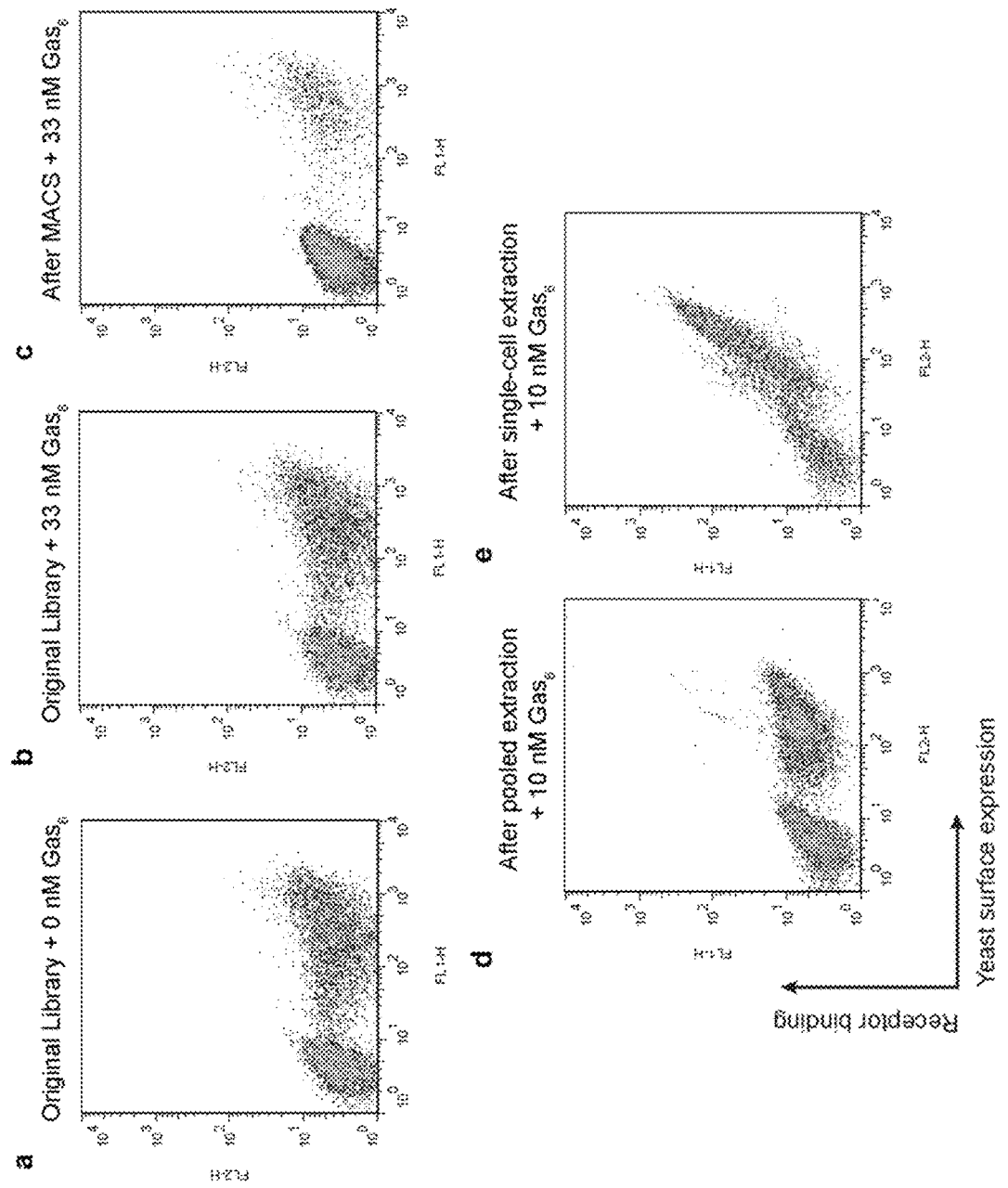
FIG. 12 shows flow cytometry scatter plots throughout the naïve library screen for a $Gas_6$-binding scFv.

With this procedure, flow cytometry was used to monitor the progress of each sorting step. The starting scFv library ($7 \times 10^8$ transformants) did not show any distinguishable binding to Gas6. FIG. 12 shows flow cytometry scatter plots throughout the naïve library screen for a $Gas_6$-binding scFv. Magnetic-activated cell sorting (MACS) was first used to clear the library of non-specific binding scFvs, followed by a round of MACS using Gas6-coated magnetic beads which reduced the theoretical library size to $2.8 \times 10^6$ clones. FIG. 12, panel a) shows an original scFv naïve library (library size: $7 \times 10^8$) stained with 0 nM Gas6. Panel b) shows an original scFv naïve library stained with 33 nM $Gas_6$. Panel c) shows the scFv library after MACS (library size: $2.8 \times 10^6$). The resulting pool of scFv variants was enriched for binders to Gas6 using two rounds of screening on the µSCALE platform.

FIG. 10C shows scatter plots for rounds of µSCALE screening of a yeast surface-displayed naïve scFv library for Gas6 binders. Sort 1: automated pooled extraction with a user-drawn gate (left), Sort 2: manual single-cell extraction (right). Grey dots, extracted clones; outlined grey dots, clones with highest binding to Gas6. In the first round, a relatively low concentration of Gas6 (33 nM) was added to the library and allowed to reach equilibrium. Approximately 150 microcavities containing yeast with the highest Gas6 binding levels, normalized to the amount of scFv expression, were selected via pooled extraction (FIG. 10C, left). This extracted yeast pool was cultured, re-induced for scFv expression, and analyzed by flow cytometry, where a population of yeast with specific binding to Gas6 but not to antibody-based detection reagents was evident. FIG. 12, panel d) shows the scFv library isolated after the first µSCALE sort via auto-extraction (library size: 143).

A second µSCALE screen was performed under more stringent selection pressure (10 nM Gas6). In this screen, 15 microcavities were isolated via single-cell extraction and sequenced (FIG. 10C, right) and FIG. 12, panel e), which shows A Gas$_6$-binding scFv clone isolated after second µSCALE sort via single-cell extractions.

Retrospective examination of the screen revealed that the 5 microcavities with the highest observed Gas6 binding levels (normalized to scFv expression) were the same clone (FIG. 10C, right). FIG. 10D shows the Gas6 binding curve of the yeast-displayed scFv identified by µSCALE, represented as the fraction of Gas6 bound versus the concentration added. the resulting scFv variant bound to Gas6 with a $K_D$ of 130±30 nM comparable to other binders mined from naïve scFv libraries. Error bars correspond to the standard deviation of three independent measurements.

Example 3

Affinity Maturation of Axl Receptor: Error-prone Library Sort

Gas6/Axl was used as a model system to isolate high-affinity Axl variants that functioned as effective inhibitors of tumor metastases. The protein engineering strategy included two iterative rounds of library generation and screening: an initial library of randomly generated Axl mutations and a second library of recombined Axl mutations derived from the variants recovered from the first library.

One round of MACS using Gas6-coated magnetic beads, which reduced the theoretical library size to 3.5×10$^6$ clones and the array was loaded at a concentration to result in an average of 4 cells per microcapillary.

Figure 34:
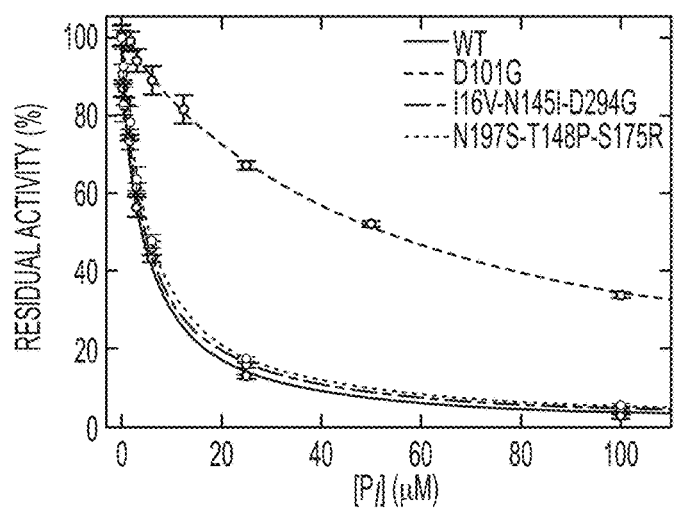
FIG. 34 shows phosphate inhibition curves for WT enzyme and the three improved variants isolated from screens according to the method of the disclosure.

The resulting pool of Axl variants was cultured, induced, and incubated with 100 pM Gas6 for 15 hours to allow for equilibrium binding. The library was diluted to 12,600 cells/µL, a concentration to yield an average of 4 cells per 20 µm diameter capillary, and imaged with epi-fluorescence in two colors. To enrich for Gas6 binders, we individually extracted 30 microcapillaries containing yeast with the highest levels of Gas6 binding relative to Axl expression levels, and propagated the contents of each microcapillary separately (FIG. 34). At least one cell grew in 22 of 30 extractions, yielding 30 total clones. When the plasmid DNA from these yeast clones was sequenced some mutational consensus was observed, notably, D87G and V92A mutations.

To combine beneficial mutations and remove neutral or deleterious mutations, DNA isolated from the library clones was used as a template to generate a second library via staggered extension process (StEP). We screened this second library using a kinetic off-rate assay to isolate Axl mutants that remain bound to Gas6 ligand after an extended time period, hence selecting for variants with a slower dissociation rate. The yeast-displayed Axl library was incubated with saturating levels of Gas6, washed to remove the unbound ligand, and allowed to dissociate in the presence of excess wild-type Axl Ig1 Fc for 24 hours before antibody staining. Even after 24 hours of disassociation, a subset of this library retained high levels of binding, which was clearly observed on µSCALE. We extracted 40 individual microcapillaries exhibiting the highest Gas6 binding relative to Axl expression levels and propagated the contents of each microcapillary separately. We recovered at least one cell from 30 extractions, yielding 42 total clones.

Figure 43:
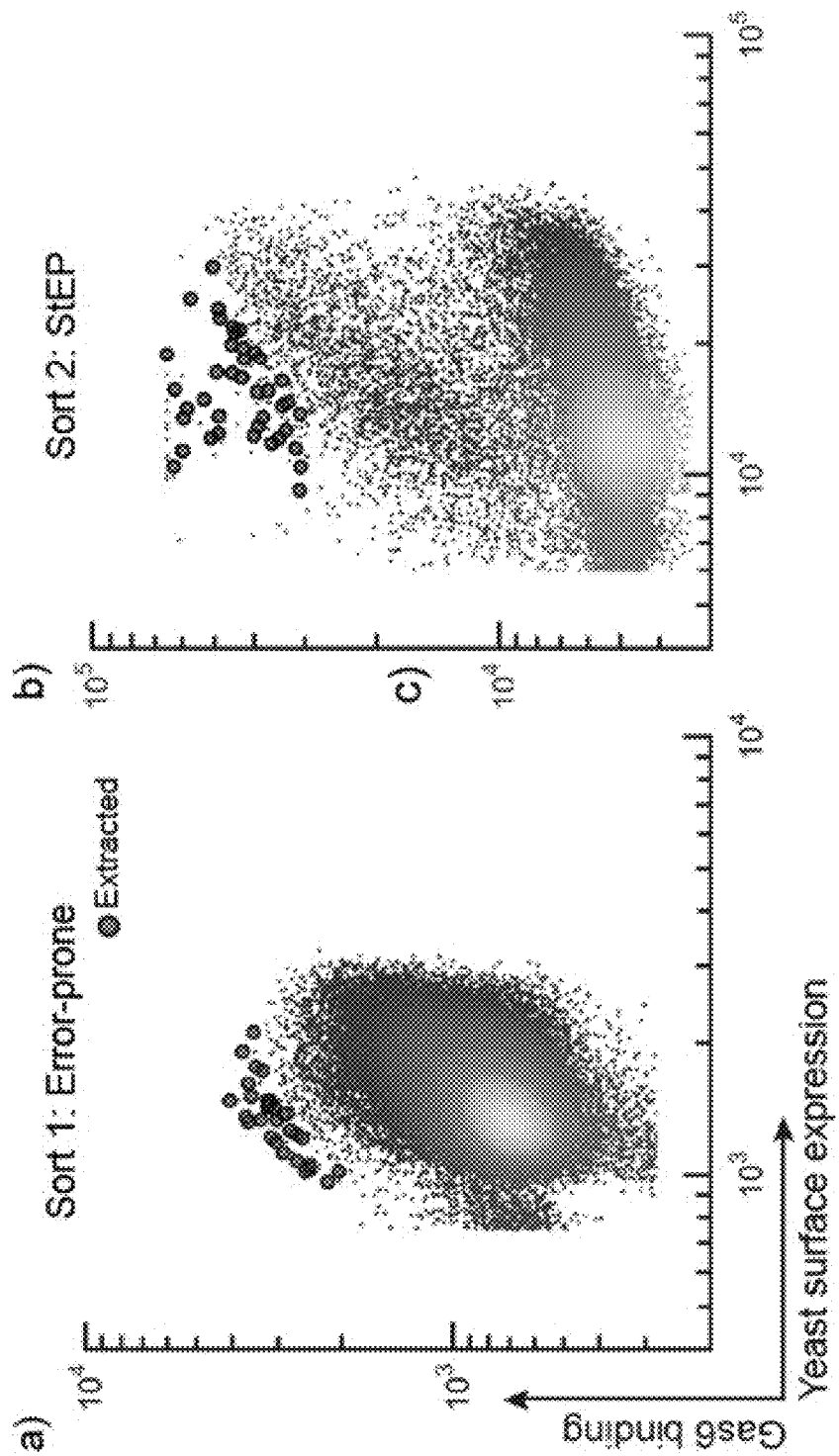
FIG. 43 shows screening of a yeast surface-displayed error-prone Axl Ig1 library for Gas6 binders according to a method of the disclosure.
Figure 44:
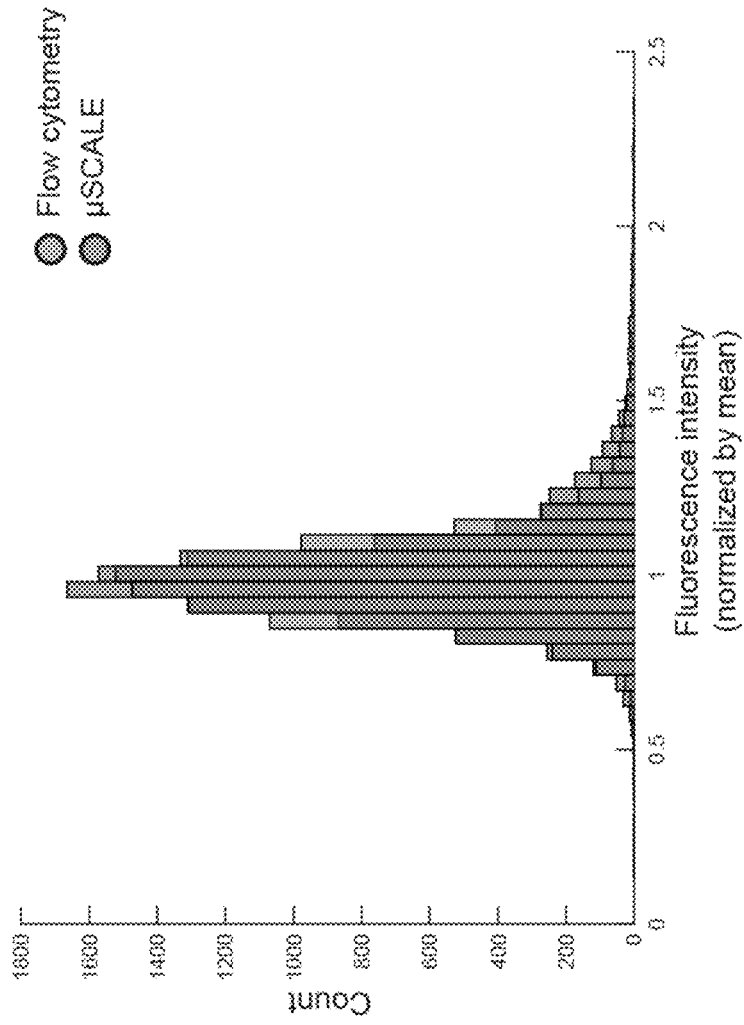
FIG. 44 shows an assessment of inter-capillary variability in fluorescence measurements in an example method according to the disclosure in comparison to that observed in a Fluorescence Activated Cell Sorting (FACS) flow cytometry analysis.

FIG. 43 shows screening of a yeast surface-displayed error-prone Axl Ig1 library for Gas6 binders. This library was incubated with 100 pM of Gas6 for 15 hours to allow for equilibrium binding. 30 microcapillaries were extracted separately. 22/30 extractions grew, resulting in 30 clones. (b) After StEP, we performed a kinetic off-rate sort for 24 hours before antibody staining. From this library, 30 microcapillaries were extracted separately. 23/30 extractions grew, resulting in 45 clones.

After sequencing of the plasmid DNA from the extracted yeast clones, we observed strong consensus mutations, in particular, A72V, D87G, V92A, and V126I mutations. The mutations of D87G and V92A are the key drivers of affinity in previously characterized Axl Ig1 variants. In addition to D87G and V92A, the point mutation A72V was also identified from the original error-prone PCR library when screened by FACS in our previous work and was found to be a strong contributor to Gas6 binding, both alone and in combination with D87G and V92A, in a subsequent study.

Figure 42B:
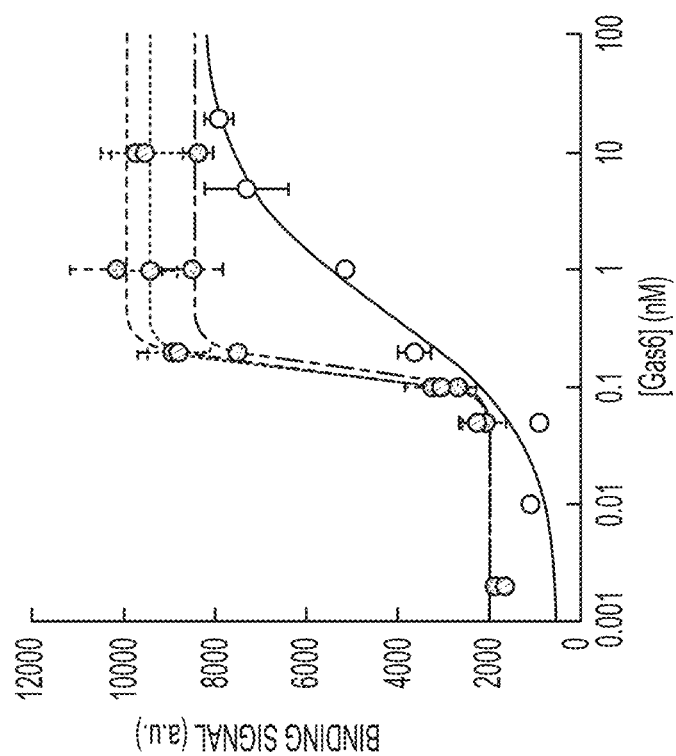
FIG. 42B shows kinetic dissociation of Gas6 from yeast-displayed Axl as a function of incubation time with excess competitor in accordance with an example method of the disclosure.
Figure 42A:
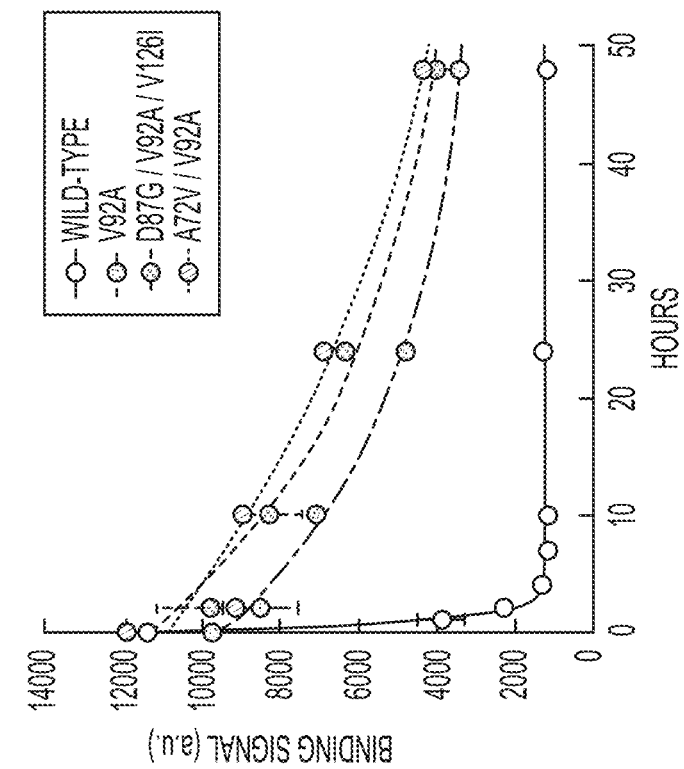
FIG. 42A shows equilibrium binding titrations of yeast-displayed Axl variants to Gas6 competitor in accordance with an example method of the disclosure.

To validate the final clones, we performed binding assays with yeast display variants that appeared most frequently from µSCALE screening. The yeast-surface displayed WT Axl Ig1 bound Gas6 with a $K_d$ of 500±300 pM and a binding off-rate ($k_{off}$) of 4670±190 s$^{-1}$ (n=3 technical replicates). All of the engineered Axl Ig1 variants demonstrated improved binding to Gas6 with affinities approximately 3-fold tighter than that of WT Axl and up to a 50-fold slower kinetic dissociation rate. See Table 6 and FIGS. 42A and B (error bars indicate s.d. of three technical replicates)

TABLE 6

|  | Residue No. | | | | Gas6 Affinity | |
| --- | --- | --- | --- | --- | --- | --- |
|  | 72 | 87 | 92 | 126 | $K_D$ (pM) | $K_{off}$(s$^{-1}$) |
| WT Axl | A | D | V | V | 500 ± 300 | 4670 ± 190 |
| V2-1 |  |  | A |  | 146 ± 5.4 | 175 ± 41 |
| V2-2 |  | G | A | I | 135 ± 7.9 | 153 ± 84 |
| V2-3 | V |  | A |  | 137 ± 5.6 | 91 ± 128 |

The similarity between the measured binding affinities could reflect a limitation in on-yeast binding assays rather than the true protein binding interaction. Binding affinity is described using the dissociation constant ($K_d$), an equilibrium constant that is equal to the concentration of ligand needed to occupy half of its binding partner. The dissociation constant is a ratio of association and disassociation rates:

$$K_d = \frac{k_{off}}{k_{on}}.$$

Researchers must be aware of two common issues when measuring cell-associated binding affinity: ligand depletion and equilibrium time.

A common assumption when performing binding assays is that the soluble concentration of the ligand remains constant. In other words, one assumes that only a small fraction of the free ligand binds its binding partner. It is good practice to ensure less than a tenth of the ligand is removed from solution. However, for high affinity proteins, there is a risk for a substantial fraction of the ligand to bind its binding partner, depleting the free ligand concentration. For example, $5 \times 10^5$ yeast cells, each expressing $5 \times 10^5$ copies of a high affinity ($K_d$=10 pM) binder, will bind approximately $1.25 \times 10^9$ ligands from a 10 pM ligand solution. To prevent ligand depletion in this scenario, one must use a reaction volume of at least 2.1 mL, increasing the amount of total protein needed. For reaction volumes over 2.5 ml, large (15 ml or 50 ml) tubes must be used. Spinning and decanting samples in these tubes is significantly more laborious and prone to error. Still, to ensure proper reaction conditions, we optimized the volume needed to prevent ligand depletion, using reaction volumes up to 50 mL.

The association and disassociation rates combined with the concentration of the ligand can be used to estimate the time needed for the protein interaction to approach equilibrium. If the soluble protein concentration is in molar excess of the yeast-displayed protein (to prevent ligand depletion), the time constant ($\tau$) for approaching equilibrium is $\tau=(k_{on}*[L]_0+k_{off})^{-1}$, where $[L]_0$ is the initial concentration of the ligand. To further characterize the binding interaction between our Axl variants and Gas6, we measured their on-yeast kinetic off-rates. We observed a dramatic difference between WT Axl and our engineered variants. Yeast-bound Gas6 levels rapidly dissociated to background levels within 6 hours for WT Axl, but our Axl variants retained more than 10% of initial Gas6 binding levels after 48 hours. Notably, the A72V/V92A variant ($k_{off}$=7.1×10$^{-6}$ s$^{-1}$) has a 2-fold slower off-rate than the other two variants ($k_{off}$=1.4×10$^{-5}$ s$^{-1}$). Previously characterized Axl Ig1 variants all had kinetic on-rate values around $2 \times 10^7$ M$^{-1}$ s$^{-1}$, suggesting that affinity enhancements were a result of slower off-rates. Interestingly, these on-rate values are 100-fold higher than those of typical antibody fragments[58]. With these fast on-rate values, we can see that for the lowest ligand concentration ($[L]_0$=10 pM), the reaction between the variants and Gas6 will reach 99% equilibrium binding (4.6$\tau$) in under 6 hours. Even for a theoretical $[L]_0$=1 pM condition, all reactions will reach 99% equilibrium binding under 48 hours, which was the equilibrium time used in the experiment.

Despite taking these measures to ensure accurate binding affinity measurements, the binding affinities of yeast-displayed Axl variants are likely underestimated due to inherent limitations of yeast-displayed binding. For example, previous work with the Kinetic Exclusion Assay (KinExA) showed that Gas6 bound to soluble wild-type Axl or the V92A mutant with an affinity of 33±0.6 pM and 12.0±0.2 pM, respectively 10.

Despite our careful considerations of assay conditions, the affinities of yeast-displayed Axl variants are likely underestimated due to inherent limitations of yeast-displayed experiments. For example, previous work with the Kinetic Exclusion Assay (KinExA) showed that Gas6 bound to soluble wild-type Axl or the V92A mutant with an affinity of 33±0.6 pM and 12.0±0.2 pM, respectively.

Axl Ig1 Equilibrium Sort

Yeast isolated from MACS were grown in SD-CAA minimal yeast media (20 g dextrose; 6.7 g Difco yeast nitrogen base; 5 g Bacto casamino acids; 5.4 g Na$_2$HPO$_4$; 8.56 g NaH$_2$PO$_4$.H$_2$O; dissolved in deionized H$_2$O to a volume of 1 liter) and induced to express Axl on their surface by culturing in SG-CAA media (prepared as SD-CAA except using 20 g galactose substituted for dextrose). Yeast displaying Axl variants were incubated at room temperature for 15 hr in PBSA (phosphate-buffered saline+1 mg/ml BSA) containing 100 pM Gas6. Following incubation with Gas6, cells were stained in PBSA containing a 1:200 dilution of chicken anti-c-Myc antibody (Thermo Fisher Scientific, A21281) for 45 min at 4° C. Cells were then incubated in PBSA containing a 1:100 dilution of mouse anti-His Tag IgG Hilyte Fluor 555 (Anaspec, 61250-H555) for 45 min at 4° C. Then, an additional secondary labeling for Gas6 was performed in PBSA with 1:100 dilution of rabbit anti-mouse IgG Hilyte Fluor 555 (Anaspec, 28164-H555) for 45 min at 4° C., followed by secondary labeling for c-Myc in PBSA with 1:100 dilution of goat anti-chicken IgY Alexa Fluor 488 (Thermo Fisher Scientific, A11039) for 45 min at 4° C. Labeled yeast were diluted to ~12,600 cells/µl and loaded into a 20 µm microcapillary array, and analyzed for Gas6 binding and c-Myc expression using excitation/emission parameters described above. Thirty microcapillaries with the highest Gas6 binding/c-Myc expression ratio were individually extracted. Extracted yeast were grown on SD-CAA agar plates and the plasmids they contain were analyzed by colony PCR and sequencing as described below.

Axl Ig1 Kinetic Off-rate Sort

Yeast cells transformed with the DNA shuffled library were grown in SD-CAA minimal yeast media and induced to express Axl on their surface by culturing in SG-CAA media. The yeast-displayed library was incubated at room temperature for 3 hr in PBSA containing 2 nM Gas6, washed with PBSA twice to remove unbound Gas6, and then incubated with an excess amount (100 nM) of wild-type Axl Fc competitor for 24 hr at room temperature. Fluorescent antibody labeling and microcapillary array loading was conducted in a similar manner to the µSCALE equilibrium sort as described above. For the µSCALE kinetic off-rate sort, 40 capillaries with the highest Gas6 binding/c-Myc expression ratio were individually extracted. Extracted yeast were grown on SD-CAA agar plates and the plasmids they contain were analyzed by colony PCR and sequencing.

Example 4

Cell Growth and High-throughput Screening of Fluorescent Proteins

Methods

Figure 41:
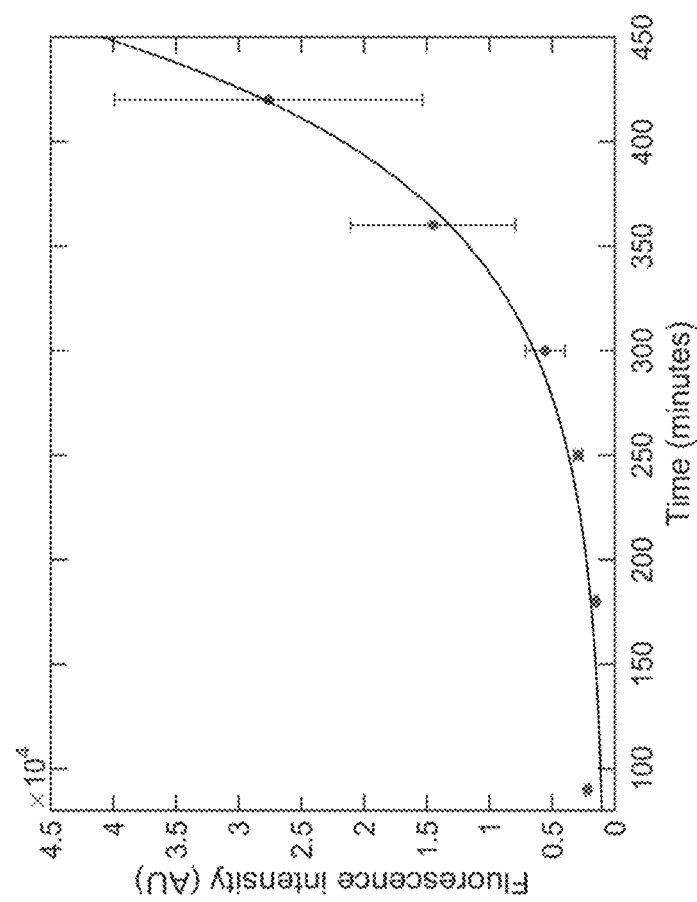
FIG. 41 shows growth of GFP-expressing *E. coli* in microcavities measured by fluorescence intensity according to an example system and method of the disclosure.

Growth of cells in microcavity arrays. A 20 µm diameter microcavity array was loaded at an *E. coli* concentration that results in a mean of 1 bacterium per microcavity, incubated at 37° C. in LB medium containing 0.2% arabinose, and serially imaged. Green fluorescence of 4000 microcavity cultures was quantified as a function of time, resulting in the observed growth curve shown in FIG. 41. Based on the fitted exponential curve, the observed doubling time was 52.8±0.5 minutes (uncertainty estimated by case resampling of the 4000 fit time courses), closely matching the doubling time in bulk culture of 56±5 minutes (n=5 biological replicates). The high degree of variability in fluorescence intensity between microcavities at later time points reflects cell-to-cell heterogeneity in growth dynamics.

Fluorescent protein library construction and screening. ddFP technology involves the reversible association of two dark FP monomers to form a fluorescent heterodimer. The convention for naming the constituent FP monomers is ddFP-A and ddFP-B. The ddFP-A monomer possesses the quenched chromophore, while the ddFP-B monomer lacks a chromophore. We designate the non-covalent complex as ddFP-AB (e.g., ddOFP-AB) and the genetically fused tandem dimer as tdFP-AB. tdRFP-AB was cloned into the pBAD expression plasmid between XhoI and EcoRI restriction sites (where ddRFP-B was the 5' partner in the tandem gene fusion) and used as a template for engineering ddOFP-AB. First, M66T was introduced into ddRFP-A by site-directed mutagenesis. An error-prone library was created by randomly mutagenizing the ddRFP-A(M66T) gene using the following error-prone PCR reaction conditions: 0.15 or 0.075 mM $MnCl_2$, 10 ng template, 200 µM dATP, 200 µM dGTP, 1 mM dTTP, 1 mM dCTP, 4 mM $MgCl_2$. Forty cycles of PCR amplification were carried out for each reaction using Taq polymerase with an extension temperature of 68° C. Mutant gene libraries were cloned 3' to ddRFP-B, making a library of tandem FP variants, and transformed into DH10B electrocompetent E. coli for growth and screening within the µSCALE platform.

To create a highly fluorescent ddOFP, µSCALE was used to screen 3 successive E. coli libraries, with error-prone PCR performed on the isolated DNA in between each round of screening. In each library cycle, an overnight outgrowth of cells in LB media at 37° C. with shaking was performed after transformation to allow E. coli to recover. Cultures were then diluted to ~3,200 cells/µL in expression media (LB supplemented with ampicillin (100 µg/ml) and arabinose (0.1%)), loaded on a 20 µm array, and incubated overnight at 37° C. in a sealed Petri dish with a moistened Kimwipe. After overnight growth, arrays were analyzed for fluorescence intensity with 525/45 nm excitation/565 nm long pass emission filters. For µSCALE round 1, 10 cavities were auto-extracted as a bulk population, which was used to create the next library via error-prone PCR as described above. For µSCALE round 2, 12 cavities were extracted via single-cell sorting. The 4 clones with the highest fluorescence signal were used to create the third generation error-prone library with the same conditions above. For the third and final µSCALE round, the top 10 cavities were extracted via single-cell sorting. To evaluate protein characteristics after each library screen, extracted cells were cultured overnight at 37° C. with shaking in expression media. Fluorescent proteins were extracted using B-Per (Pierce) and spectra were collected using a Biotek Synergy H4 plate reader.

ddOFP spectral properties. Prior to spectral analysis, all proteins were purified using metal chelating Ni-NTA chromatography and dialyzed into PBS. Emission spectra were recorded with a Biotek Synergy H4 plate reader. Absorbance measurements were made on a Varian Cary 50 UV/Vis Spectrophotometer using a 1 cm quartz microcell cuvette. The alkaline chromophore denaturation method was used to determine ε values. mCitrine (Φ=0.76) was used as the reference for quantum yield determination for ddOFP. pH titrations were performed by incubating purified proteins in buffers of desired pH and acquiring emission spectra with a 96-well Biotek Synergy H4 plate reader. A 1 µM solution of fluorescent protein was prepared in PBS and diluted 1:10 with a universal buffer of desired pH. This universal buffer solution was prepared by mixing equal volumes of 0.04 M $H_3BO_3$, 0.04 M $CH_3COOH$, and 0.04 M $H_3PO_4$. The pH was adjusted to the desired value by adding 1M NaOH to the prepared stock solution. The $pK_a$ was determined by fitting the experimental data to the equation:

$$F = A + B(1 + 10^{(pK_a - pH)n_H})^{-1},$$

where F is fluorescence, A and B are variables that define the baselines, and $n_H$ is the Hill coefficient. Mean integrated emission peak intensities were normalized and plotted as a function of pH.

µSCALE was used to engineer a new fluorescent protein variant, expanding the color palette of available biosensors and demonstrating the compatibility of the platform with E. coli libraries. Conventionally, fluorescent proteins are engineered by screening individual E. coli colonies grown on agar dishes to identify desired color hues and/or brightness (Ai, H.-W., et al., Nat. Protoc. 9, 910-28 (2014)). While straightforward, this low-throughput method relies on basic optics and laborious colony picking, which is time consuming, subjective, and hampers recovery of the most desirable variants. We first established the ability to culture spatially segregated cultures from individual E. coli cells in the microcavity array. Fluorescent protein-expressing E. coli suspensions were loaded in the array at a concentration to obtain a single cell per pore, incubated at 37° C., and imaged at various intervals. The resulting time course shows robust clonal expansion and fluorescent protein production. E. coli growth is confined within cavities, creating a dense array of segregated cultures.

Figure 13:
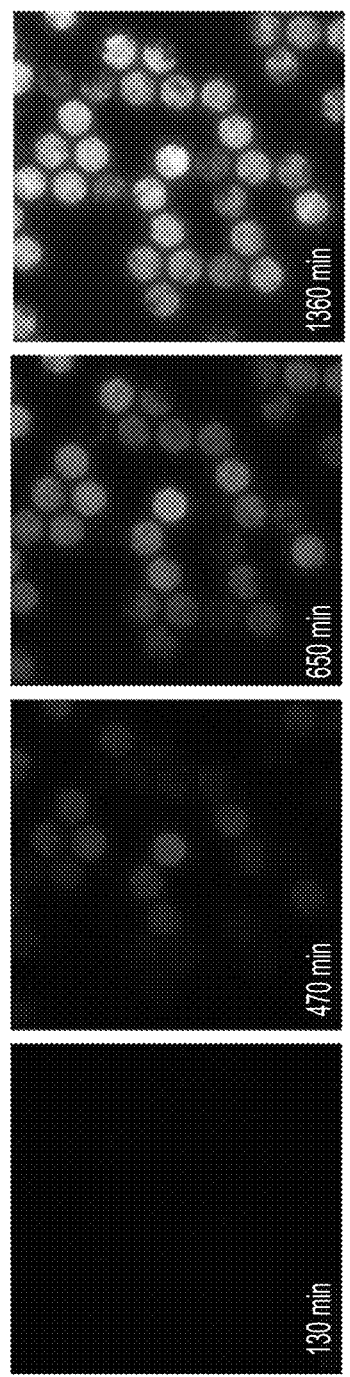
FIG. 13 shows an image of an array used for engineering an orange-hued fluorescent protein with an example system and example methods of the disclosure.
Figure 14:
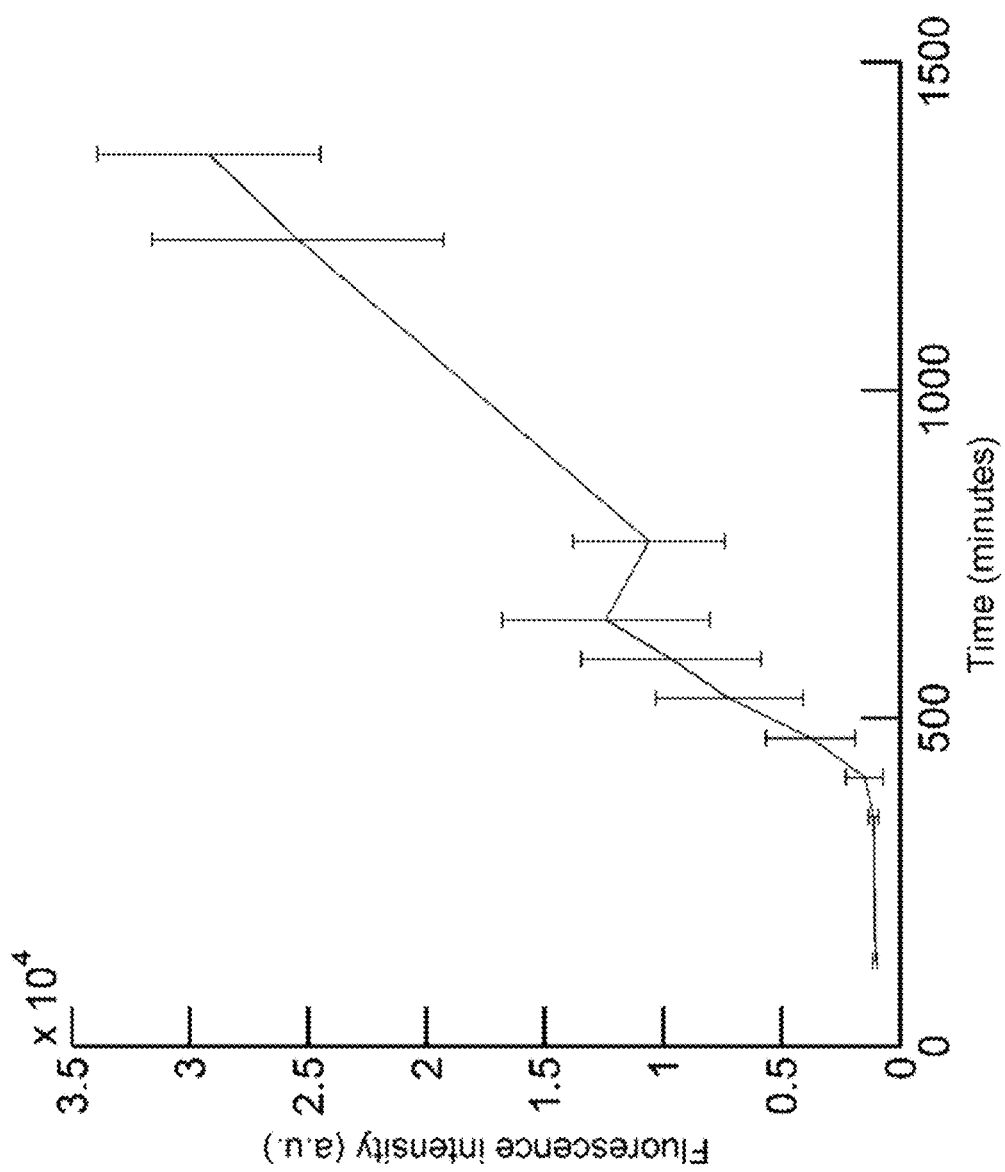
FIG. 14 shows the results of an experiment to show the growth of spatially segregated E. coli cultures expressing GFP in accordance with a method of the disclosure.
Figure 15B:
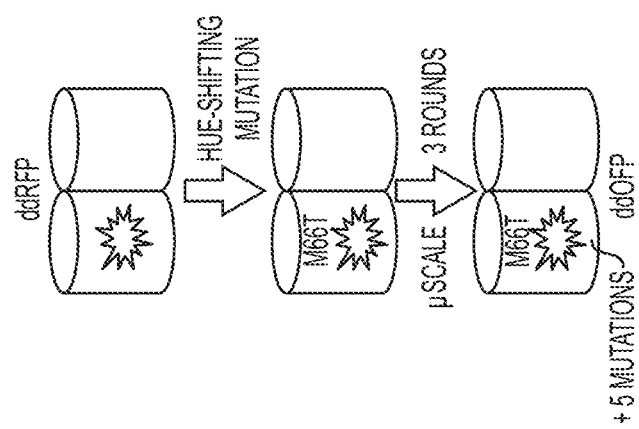
FIG. 15B depicts the engineering strategy used to generate ddOFP from the ddRFP template.
Figure 15A:
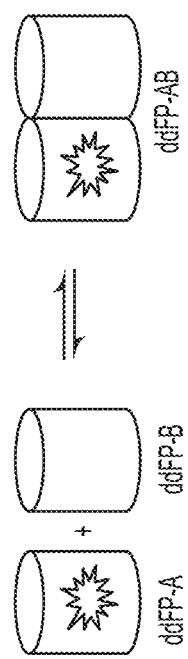
FIG. 15A illustrates ddFP technology. Weak or non-fluorescent protein monomers, designated ddFP-A and ddFP-B, reversibly bind to form a bright fluorescent heterodimer of characteristic hue. The chromophore is indicated by a starburst.

FIG. 13 shows the growth of the spatially segregated E. coli cultures expressing GFP. Images depict a small portion of a 20 µm array, which was loaded with a single bacteria cell per microcavity, cultured at 37° C. for the indicated times and serially imaged. FIG. 14 reflects that growth was monitored by integrating the total GFP emission per pore. Error bars indicate +/−standard deviation of measured cavities (n=177).

µSCALE was used to generate a bright hue-shifted, new color variant of a dimerization-dependent fluorescent protein (ddFP) (FIG. 15A). Using a red dimerization-dependent protein (termed ddRFP) as a template, a blue-shifting mutation (M66T) was introduced, which initially eliminated fluorescence (Shaner, N. C. et al., Nat. Biotechnol. 22, 1567-72 (2004); Alford, S. C., et al., ACS Synth. Biol. 1, 569-75 (2012)). FIG. 15B shows the engineering strategy used to generate ddOFP from the ddRFP template. A M66T mutation was introduced into the A copy of ddRFP (starburst), generating a largely non-fluorescent hue-shifted variant. Three rounds of mutagenesis and µSCALE screening of protein libraries expressed in E. coli resulted in ddOFP, which has 5 mutations in addition to M66T.

Figure 16B:
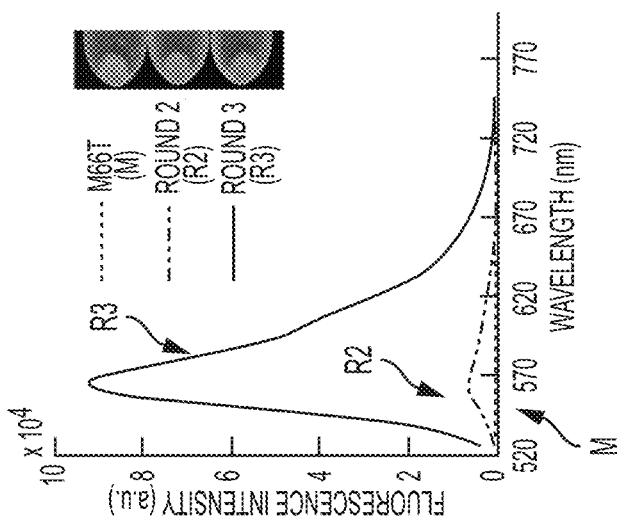
FIG. 16B shows an example of an iterative directed evolution according to a method of the disclosure.
Figure 16A:
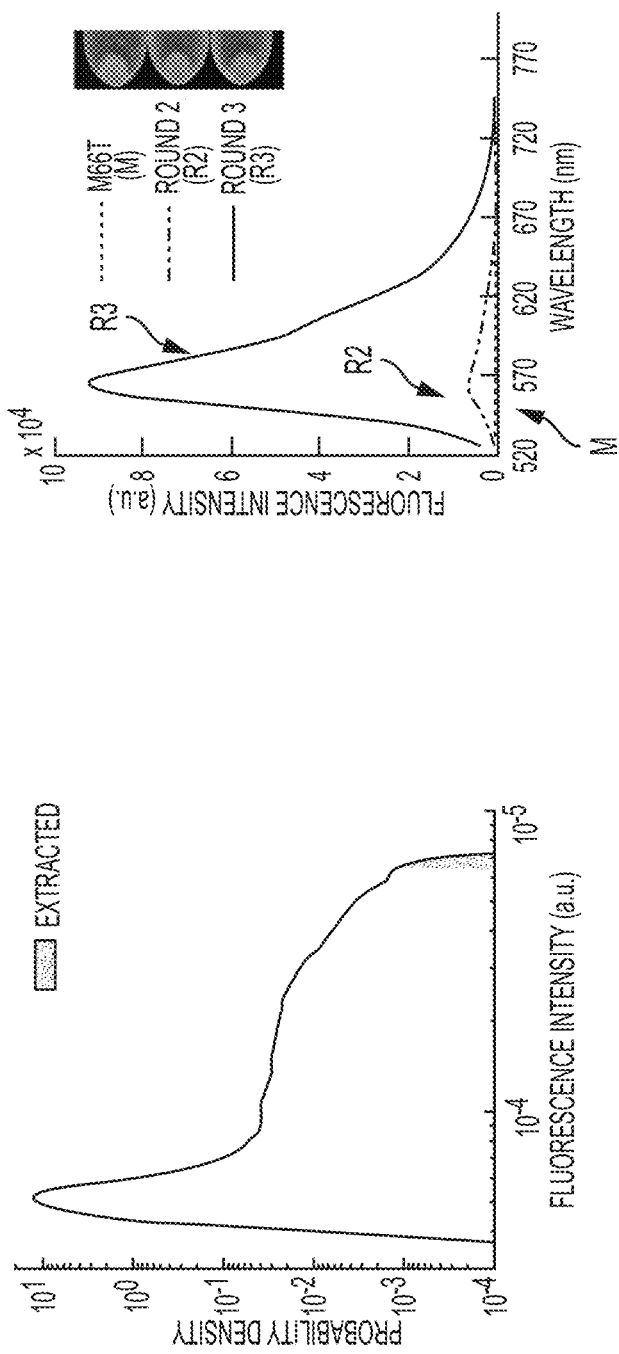
FIG. 16A shows the quantification of a screen of an E. coli library in accordance with the method of the disclosure.

To rescue and enhance fluorescence, we performed three separate rounds of directed evolution, through µSCALE screening of libraries created by error-prone PCR mutagenesis and expressed in E. coli. For directed evolution rounds 1 and 2, approximately a dozen clones demonstrating weak fluorescence were isolated and used to generate a gene template mix for a subsequent round of mutagenesis. By round 3, a fraction of the library exhibited fluorescence levels substantially higher than the library mean. FIG. 16A reflects the 10 cavities with the brightest fluorescence, which were extracted, cultured, and characterized. The brightest fluorescent protein variant was chosen for further analysis. The distribution of observed fluorescence intensities of the library variants is shown in the line trace. The 10 brightest cells at the upper tail of this distribution (shaded).

This round 3 variant, designated dimerization-dependent orange fluorescent protein (ddOFP), acquired 5 mutations in addition to the original M66T mutation that conferred a dramatic increase in fluorescence intensity relative to the best mutant from round 2 and the 'parent' M66T clone. As shown in FIG. 16B, iterative directed evolution shows increases in fluorescence intensity. The plot depicts fluorescence emission spectra of E. coli crude lysates expressing M66T, a round two variant, and ddOFP (from round 3). Inset depicts the increase in color hue of the cell pellets of E. coli expressing FP variants described above.

FIG. 17 shows a sequence alignment of the A copies of ddOFP [SEQ ID NO: 1] and its parent, ddRFP [SEQ ID NO: 2]. The original M66T mutation is encircled. Mutations acquired with the three rounds of directed evolution are highlighted in grey and underlined.

Figure 18:
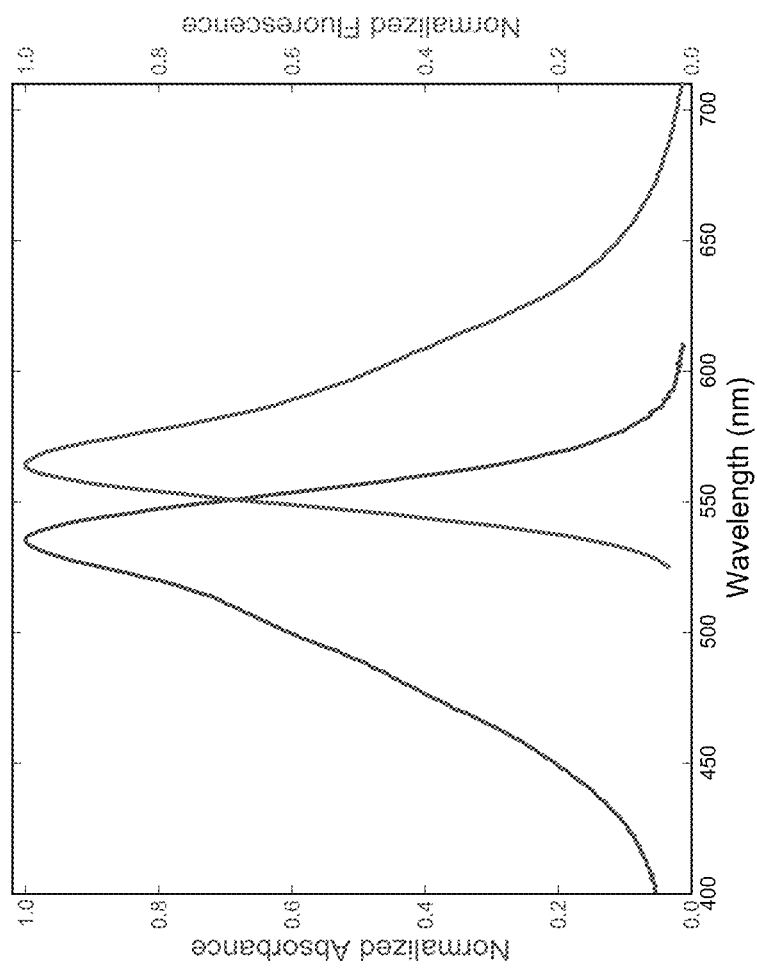
FIG. 18 shows the normalized absorbance (left) and emission (right) spectra for ddOFP.
Figure 19:
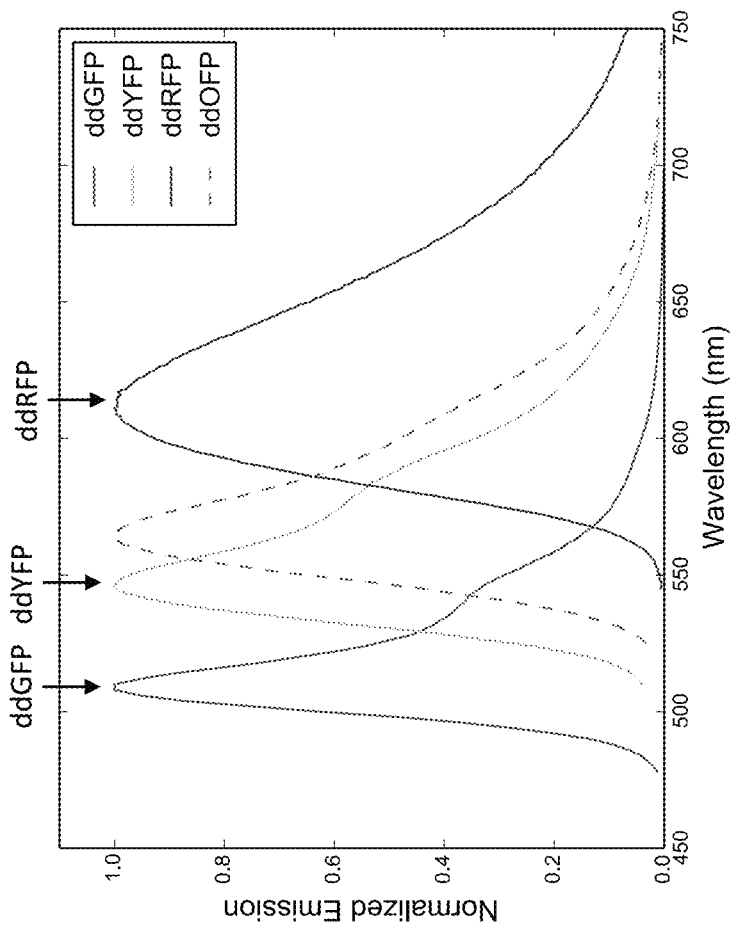
FIG. 19 shows that ddOFP fills the spectral gap between ddYFP and ddRFP.

FIG. 18 shows that ddOFP has absorption and emission maxima at 535 nm and 565 nm, respectively, filling the spectra gap between ddRFP and ddYFP variants. FIG. 19 shows the normalized emission spectra for ddGFP, ddYFP, ddOFP (dashed line), and ddRFP. Reference spectra for ddGFP, ddYFP, and ddRFP taken from Alford, S. C., et al., *ACS Synth. Biol.* 1, 569-75 (2012) and Alford, S. C., et al., *Chem. Biol.* 19, 353-60 (2012).). In addition, ddOFP exhibits comparable brightness and contrast to other ddFPs (Table 7), making it a suitable module for ddFP-based biosensing applications.

TABLE 7

Summary of spectral properties of ddOFP and ddOFP-A.

|  | EC | QY | Brightness | pKa |
| --- | --- | --- | --- | --- |
| ddOFP-A | 32200 | 0.08 | 2576 | 7.9 |
| ddOFP | 64500 | 0.31 | 19995 | 6.9 |

EC, extinction coefficient; QY, quantum yield.
QY determined relative to mCitrine QY = 0.78.

Figure 20:
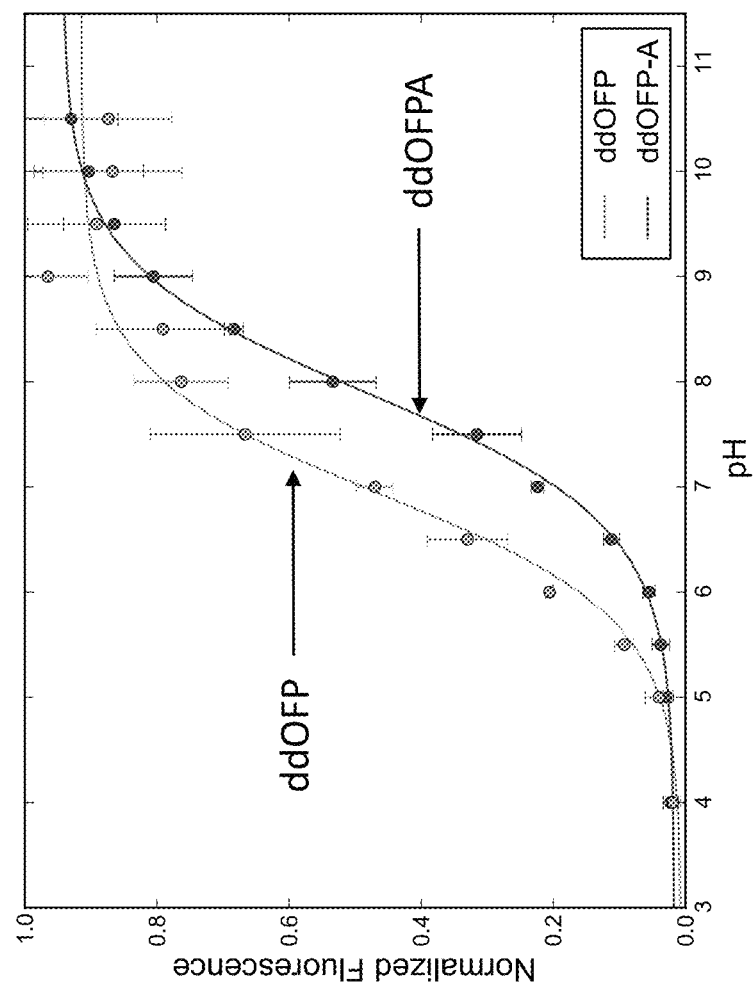
FIG. 20 shows pH-dependent emission profiles for ddOFP and ddOFP-A.

FIG. 20 shows pH-dependent emission profiles for ddOFP and ddOFP-A. Mean integrated emission peak intensities were normalized and plotted as a function of pH. $pK_a$ values for ddOFP-A and tdOFP were determined to be 7.9 and 6.9, respectively. Error bars indicate ±standard deviation for three independent experiments.

Example 5

High-throughput Kinetic Measurements and Screening for Improved Enzyme Catalysts Preparation of alkaline phosphatase protein constructs. The *E. coli* wild-type alkaline phosphatase (WT AP) gene and R166S variant used for kinetic comparisons were cloned into the pCT yeast display plasmid between NheI and BamHI restriction sites. Plasmid DNA was subsequently transformed into *S. cerevisiae* EBY100 by electroporation for yeast surface display studies. Soluble versions of WT AP and the R166S mutant were also expressed and purified from *E. coli* SM547λDE3 cells as described previously (Andrews, L. D., et al., *Biochemistry* 53, 6811-9 (2014)). Yeast cells transformed with pCT display plasmid were grown in selective media and induced as described above. The yeast induction media was supplemented with 500 μM $ZnCl_2$ and 500 μM $MgCl_2$ to provide the required metal ions for catalysis. To quantify the level of yeast surface-displayed enzyme, antibody labeling of a C-terminal c-Myc tag fused to each enzyme was performed. Approximately $8 \times 10^4$ induced yeast cells were washed and resuspended in PBSA containing a 1:250 dilution of chicken anti-c-Myc antibody (Life Technologies, A21281) for 45 min at room temperature on a rotator. After incubation, yeast were washed and resuspended in PBSA containing a 1:100 dilution of goat anti-chicken IgG Alexa Fluor 488 (Life Technologies, A11039) for 30 min at room temperature on a rotator. c-Myc expression levels were then detected on a Guava easyCyte flow cytometer (Millipore).

Figure 21:
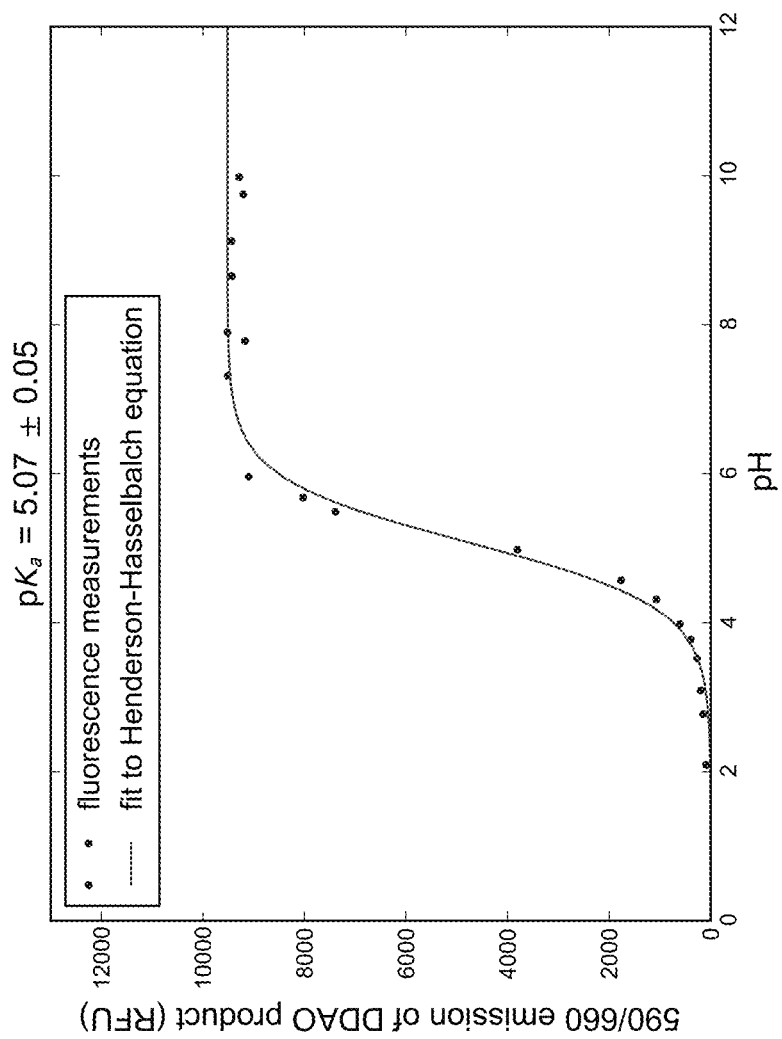
FIG. 21 shows determination of the pKa of the fluorescent DDAO product used in high-throughput screens of alkaline phosphatase (AP) mutants.

Measurement of DDAO product pKa. pH titrations were performed on 7-hydroxy-9H-(1,3-dichloro-9,9-dimethyl-acridin-2-one (DDAO) in order to determine the pH-dependence of product fluorescence. A 1 μM stock solution of DDAO was prepared in Milli-Q water and titrated with 1M HCl and 1M NaOH to adjust the solution pH. Using a Biotek Synergy H4 plate reader, fluorescence measurements at an excitation/emission of 590/660 nm were performed on aliquots from each titration step. A fit of the data to the Henderson-Hasselbalch equation yielded a pKa of 5 for the DDAO product. Thus, subsequent enzymatic assays were conducted at pH 8 (3 units above the product pKa) to eliminate fluorescence quenching arising from protonation of the DDAO nitrogen. FIG. 21 shows the results of the titrations. Error bar corresponds to a 1-σ (68%) confidence interval for the fit pKa value, and was determined by bootstrapping using case resampling of the data.

Figure 22A:
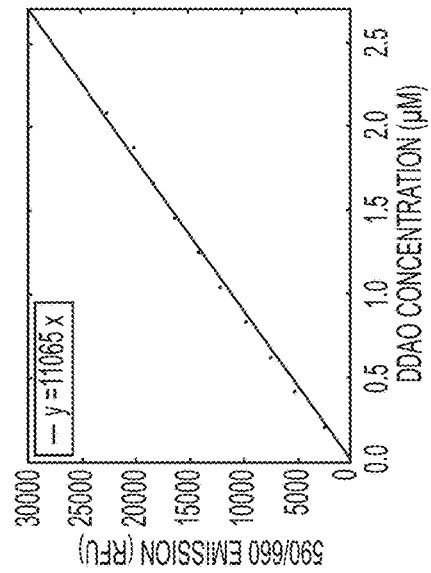
FIGS. 22A and 22B show product calibration curves for quantifying enzyme kinetics according to a method of the disclosure.
Figure 22B:
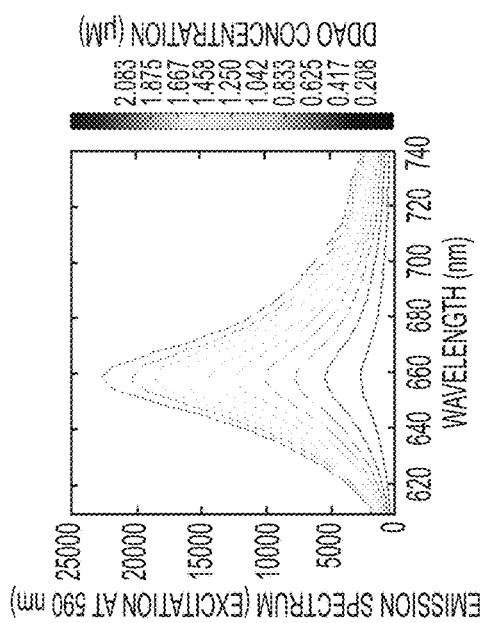

Analysis of alkaline phosphate activity. Induced yeast cells were diluted to a final concentration of ~3200 cells/μL, washed twice in AP Reaction Buffer (100 mM MOPS pH 8.0, 0.5 M NaCl, 1 mM $MgCl_2$, 100 μM $ZnSO_4$, 0.2% BSA, 1 mM mannose) (see Alford, S. C., et al., *ACS Synth. Biol.* 1, 569-75 (2012); Alford, S. C., et al., *Chem. Biol.* 19, 353-60 (2012) and resuspended in AP Reaction Buffer containing variable concentrations of DDAOP and inorganic phosphate immediately prior to analysis. Reaction mixtures were then loaded onto either 96-well microtiter plates or μSCALE arrays for bulk and single-cell experiments, respectively. Bulk kinetic assays were conducted by measuring fluorescence time courses at an excitation/emission of 590/660 nm on a Biotek SYNERGY™ H4 plate reader spectrophotometer, which allowed linear correlation of the fluorescent signal with DDAO concentration over a range from 0-3 μM. FIGS. 22A and 22B shows the emission spectra for the DDAO product measured as a function of product concentration on a Biotek plate reader spectrophotometer, and the peak emissions quantified to yield the calibration line on the right. Fluorescence acquisition parameters were as follows: Sensitivity=100, Bandwith=9.0 nm.

Figure 23:
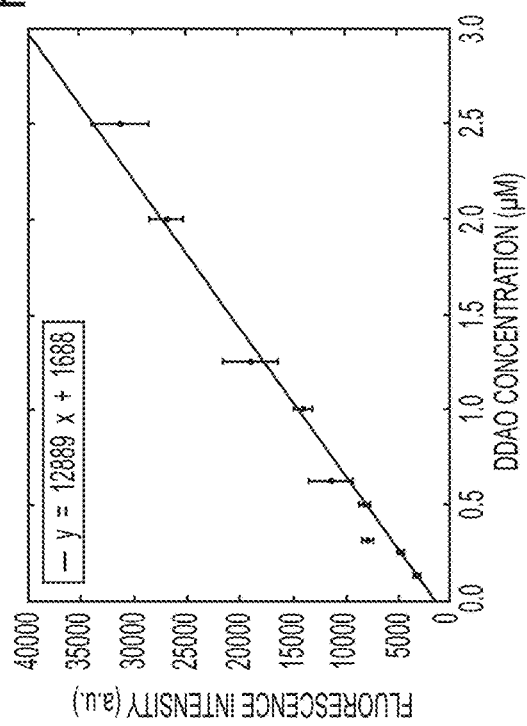
FIG. 23 shows a calibration curve was generated on a platform according to the disclosure by loading product standards of variable concentration onto isolated spots on a single microcavity array and then measuring the fluorescence intensity of each cavity on the array.

For kinetic measurements on the μSCALE platform, a series of images were acquired at set intervals with 600/60 nm excitation/655 nm long pass emission filters to generate single-cell reaction time courses for each cavity in the array. The μSCALE filter set and camera detected a linear correlation of product formation with fluorescence over a comparable dynamic range to the plate reader. FIG. 23 shows a calibration curve similar to FIGS. 22A and 22B generated on the μSCALE platform by loading product standards of variable concentration onto isolated spots on a single microcavity array and then measuring the fluorescence intensity of each cavity on the array. Error bars reflect the standard deviation across all cavities in each spot and were used to fit a calibration line using weighted least squares. In both cases, the linear regime of each kinetic time series was used to estimate reaction rates. An effective enzyme concentration of 50 pM (assuming ~$10^4$ enzyme copies displayed per cell[15,45]) was used for back-calculating rate constants from kinetic data.

Figure 24:
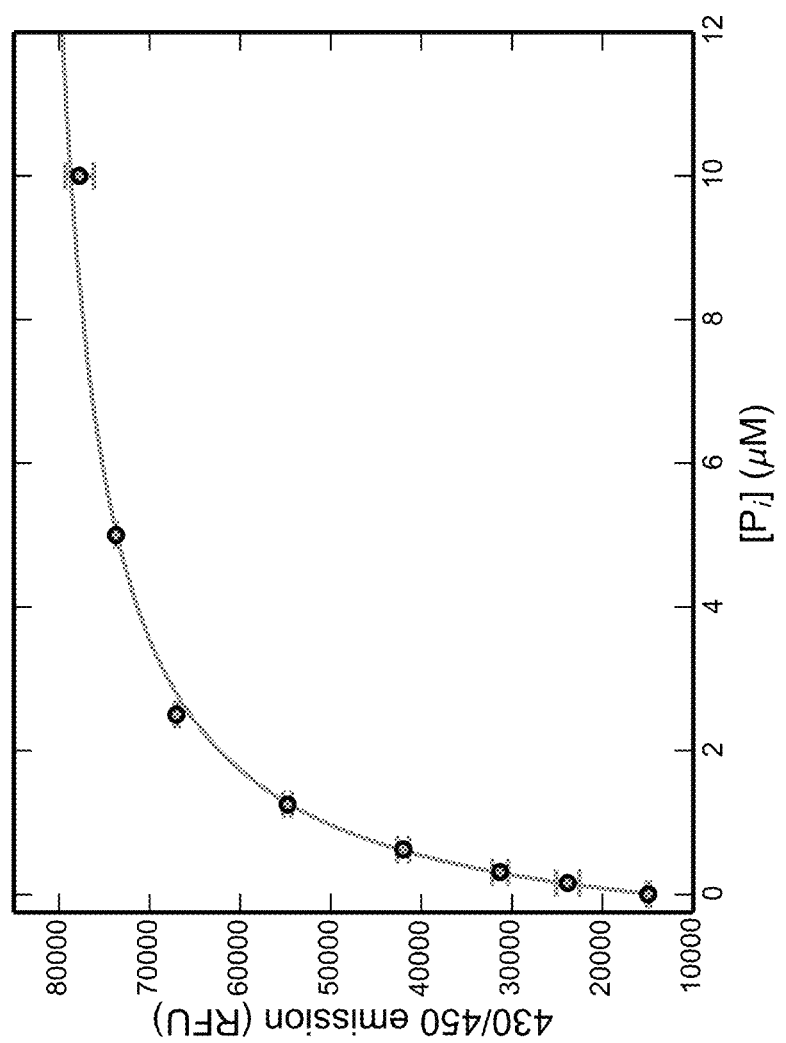
FIG. 24 shows a calibration curve for quantifying levels of inorganic phosphate contamination in AP reactions using fluorescently labeled phosphate-binding protein from E. coli.

Measurement of inorganic phosphate contamination in AP reactions. Inorganic phosphate content in all reagents used in AP kinetic assays was quantified using fluorescently labeled phosphate-binding protein (PBP) from *E. coli* (Life Technologies, PV4406) as described previously (Brune, M., et al., *Biochemistry* 33, 8262-71 (1994)). Briefly, 100 μL of each sample was mixed with 100 μL of 1 μM PBP in Phosphate Sensor Detection Buffer (20 mM TrisHCl pH 7.6, 0.05% Triton X-100), and fluorescence of the mixture was immediately read out at an excitation/emission of 430/450 nm on a Biotek SYNERGY™ H4 plate reader spectrophotometer. When measuring phosphate content in the AP Reaction Buffer, the buffer was diluted 1:20 in water prior to incubation with the sensor in order to minimize interference from the concentrated MOPS and salt solutions on the PBP binding thermodynamics. PBP stocks were stored as 10 μM aliquots in Phosphate Sensor Storage Buffer (10 mM TrisHCl pH 7.6, 50 mM NaCl) at −80° C. and individually thawed prior to use. As shown in FIG. 24, fluorescence measurements were converted to phosphate concentrations using a standard curve which was fit to a two-state binding isotherm of the form $F=F_{min}+(F_{max}-F_{min})*(1+K_d/[P_i])^{-1}$. Error bars reflect the standard deviation over three measurements. A fit to a two-state binding isotherm is overlaid above the data as a solid line. The binding parameters were determined to be: $F_{min}$=14200+/−500 RFU, $F_{max}$=85000+/−1000 RFU, and $K_d$=0.94+/−0.05 μM.

Alkaline phosphatase library construction and screening. Error-prone PCR was used to randomly mutate the WT AP gene [GENBANK Accession Number M13345] using the following reaction conditions: 0.1 mM $MnCl_2$, 10 ng WT template, 200 μM dATP, 200 μM dGTP, 1 mM dTTP, 1 mM dCTP, 4 mM $MgCl_2$. PCR amplification was performed as described above. The mutated AP insert DNA and NheI/BamHI-digested pCT plasmid were electroporated in a 5:1 weight ratio into EBY100 yeast and assembled in vivo via homologous recombination (Chao, G. et al., Nat. Protoc. 1, 755-68 (2006)). Library size was estimated to be ~$10^7$ by dilution plating.

μSCALE was used to screen the error-prone AP library for mutants with improved activity under the assay conditions. Induced yeast cells were washed twice in AP Reaction Buffer, resuspended at ~3,200 cells/μL in AP Reaction Buffer containing 1 μM DDAOP and 15 μM inorganic phosphate, and loaded into the array. After 30 minutes of reaction time, the fluorescent intensity of each cavity was analyzed as described in the AP kinetic studies. The 15 cavities with the highest fluorescent intensity were individually extracted and grown on SD-CAA agar plates. Kinetic parameters of yeast-displayed AP variants from the extracted cells were measured as described above. To genotype the three improved mutants, plasmid DNA was recovered using a Zymoprep kit (Zymo Research Corp.), transformed into DH10B electrocompetent E. coli, isolated using a plasmid miniprep kit (Thermo Scientific), and sequenced.

Figure 25:
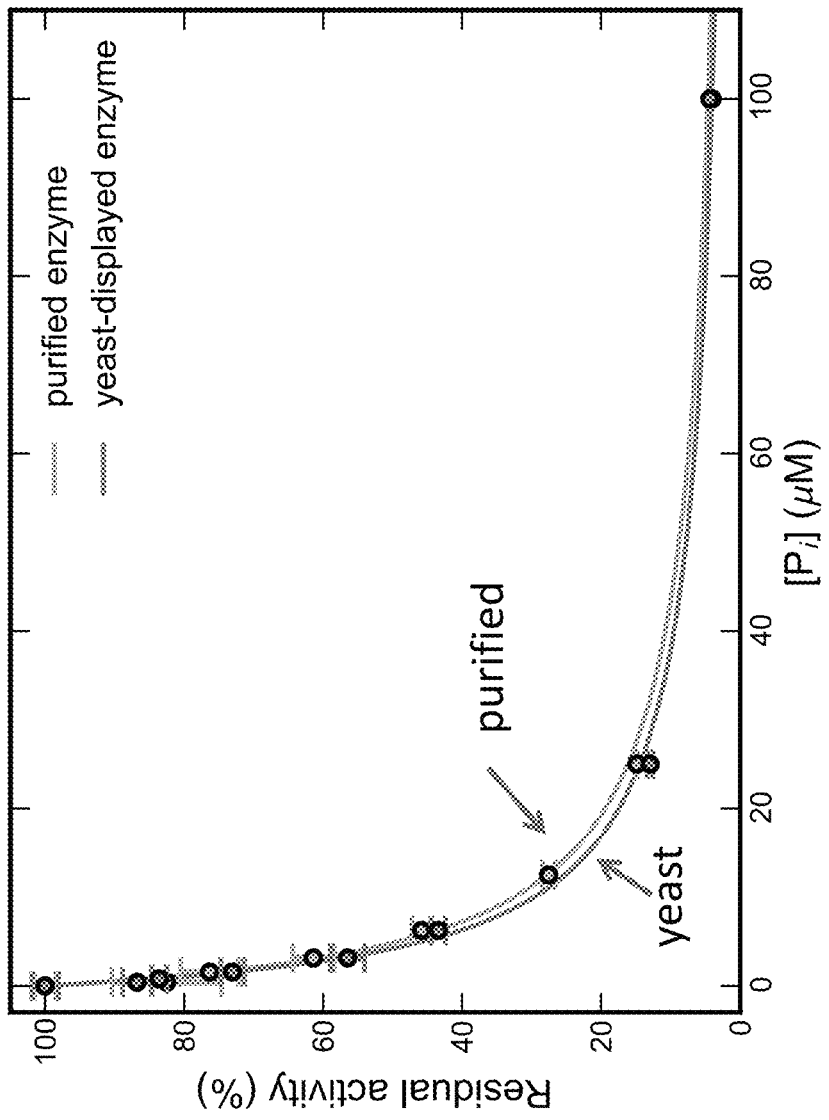
FIG. 25 shows a comparison of the phosphate inhibition profile of yeast-displayed WT AP with that of purified enzyme harvested from E. coli.
Figure 26:
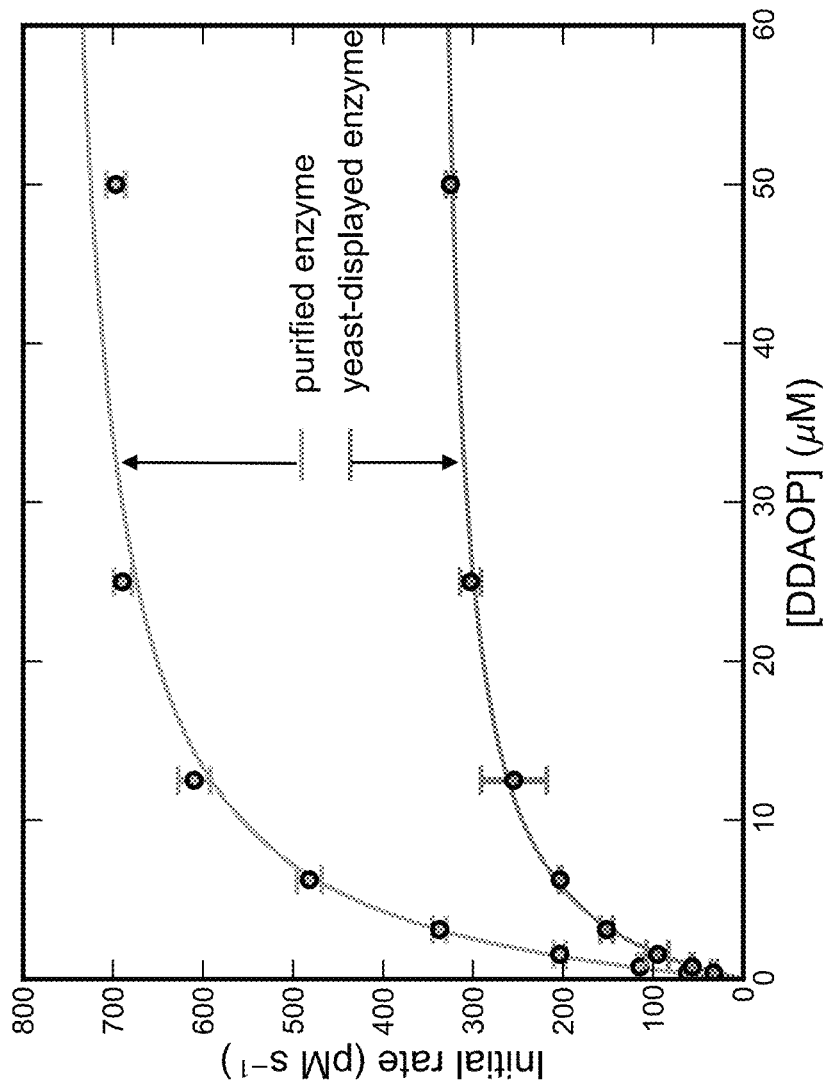
FIG. 26 shows kinetics of WT AP displayed on the surface of yeast compared to purified enzyme harvested from E. coli.

Alkaline phosphatase was used as a model system. Catalytic activity was measured using the substrate 9H-(1,3-dichloro-9,9-dimethylacridin-2-one-7-yl) phosphate (DDAOP). The Michaelis-Menten kinetics and phosphate inhibition of yeast-displayed wild-type (WT) alkaline phosphatase were within two-fold of values measured from purified enzyme harvested from E. coli. Moreover, kinetic differences between WT alkaline phosphatase and a previously characterized R166S mutant, which exhibits a significant reduction in the apparent second-order rate constant ($k_{cat}/K_M$) for the DDAOP substrate, were preserved in the yeast-displayed constructs (O'Brien, P. J. & Herschlag, D., Biochemistry 40:5691-5699 (2001). FIG. 25 shows the kinetics of WT AP displayed on the surface of yeast compared to purified enzyme harvested from E. coli. Reactions were run at a 200 μL scale in 96-well microtiter plates with either 50 pM of purified enzyme or $6.4×10^5$ cells from an induced SGCAA culture. Error bars correspond to the standard deviation of three independent measurements. Fits to the standard Michaelis-Menten model are overlaid above the data as solid lines. New sequence variants are described relative to the WT E. coli protein sequence corresponding to the nucleotide sequence of GENBANK Accession Number M13345. FIG. 26 shows the results of reactions run at a DDAOP concentration of 400 nM (10-fold below the apparent $K_m$ for WT AP). Error bars correspond to the standard deviation of three independent measurements. Fits to a competitive inhibition model are overlaid above the data as solid lines.

Table 8 shows a comparison of kinetic parameters obtained for yeast-displayed and purified AP constructs. For substrate titrations performed with yeast-displayed enzymes, initial rates were converted to enzyme turnovers by assuming an average of 104 displayed protein copies per yeast cell. Errors correspond to 1-σ (68%) confidence intervals for the fit parameters, and were estimated with the parametric bootstrap method using data from three independent measurements for each fit point.

TABLE 8

Figure 27:
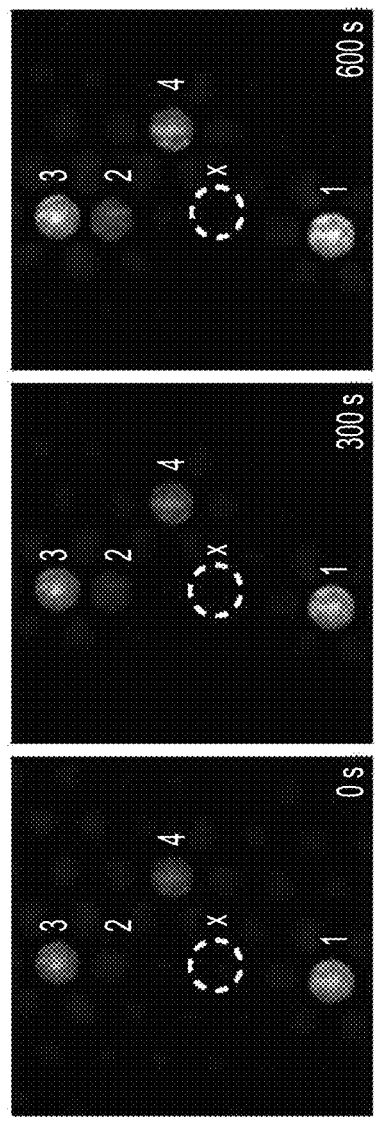
FIG. 27 shows representative snapshots from a time-resolved enzymatic assay according to methods of the disclosure.
Figure 28:
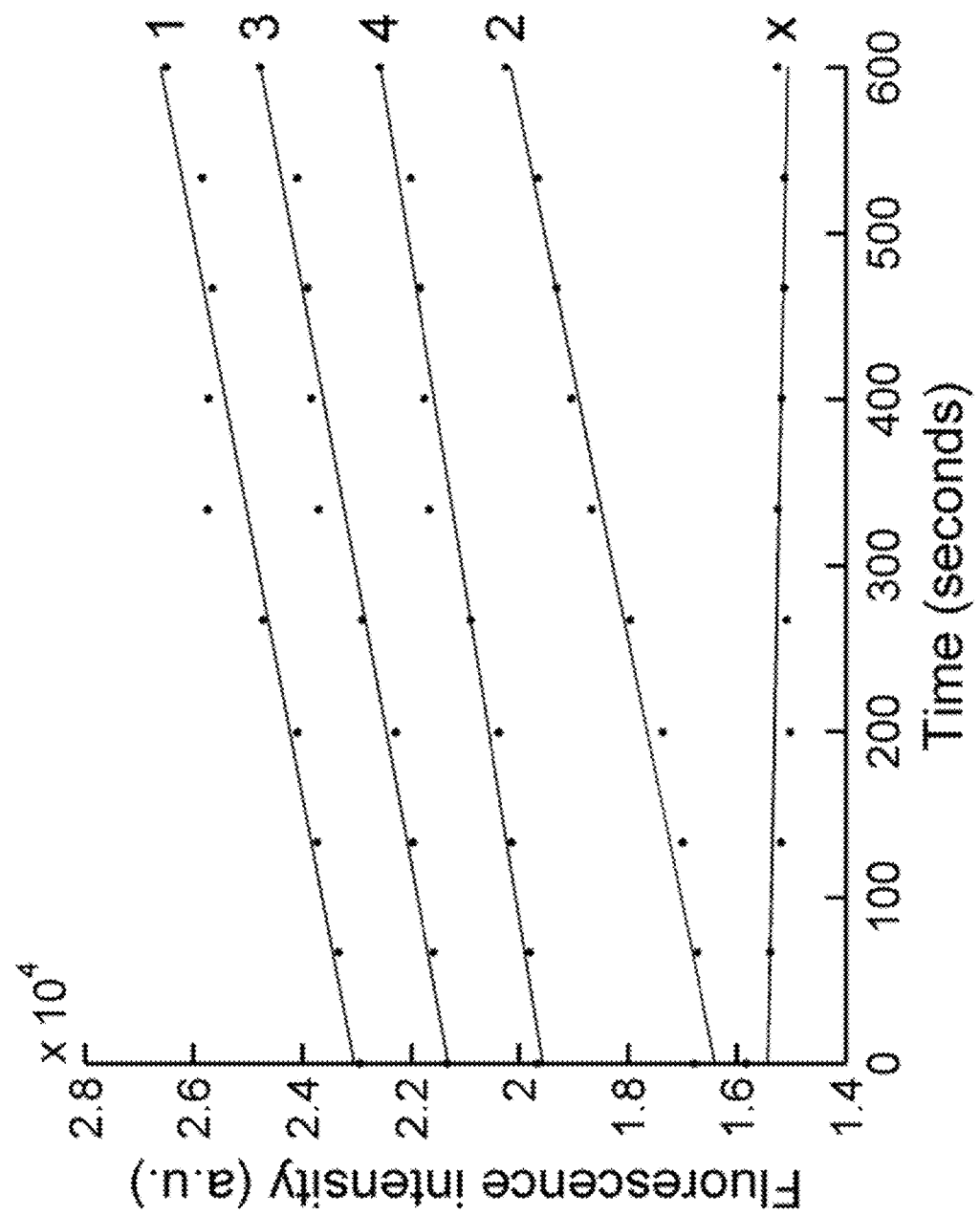
FIG. 28 shows quantification of the microcavities corresponding to the snapshots in FIG. 27.

| Mutant | Construct | $k_{cat}$ (s$^{-1}$) | $K_m$ (μM) | $K_{cat}/K_m$ (M$^{-1}$ s$^{-1}$) | $K_I$ (μM) |
|---|---|---|---|---|---|
| WT | yeast display | 7.0 +/− 0.2 | 4.3 +/− 0.4 | (1.6 +/− 0.1) × $10^6$ | 4.2 +/− 0.3 |
| WT | purified protein | 15.7 +/− 0.2 | 4.1 +/− 0.1 | (3.8 +/− 0.1) × $10^6$ | 4.8 +/− 0.3 |
| R166S | yeast display | 0.4 +/− 0.1 | 55 +/− 7 | (7 +/− 2) × $10^3$ | 1500 +/− 100 |
| R166S | purified protein | 0.7 +/− 0.2 | 51 +/− 4 | (1.4 +/− 0.4) × $10^4$ | 1580 +/− 20 |

μSCALE was used to measure single-cell reaction time courses for yeast-displayed WT alkaline phosphatase and the R166S mutant, demonstrating that the platform can provide time-resolved, kinetic information on the activity of enzyme variants. Robust spatial segregation of yeast-displayed enzymes and accumulating product 7-hydroxy-9H-(1,3-dichloro-9,9-dimethylacridin-2-one (DDAO) was maintained throughout the length of each reaction time course in the arrays, enabling facile and quantitative kinetic discrimination of cavities containing highly active yeast-displayed enzymes from inactive/less active neighbors or empty cavities FIG. 27 shows representative snapshots from a time-resolved enzymatic assay. Four microcavities harboring yeast cells displaying active enzyme are denoted in white numbering, and a nearby empty cavity is marked with an "x" for comparison. Image contrast has been artificially enhanced for clarity. FIG. 28 shows the quantification of the microcavities corresponding to the snapshots in FIG. 27. The labeling corresponds with FIG. 27, indicating four microcavities harboring yeast cells displaying active enzyme and a nearby empty cavity for comparison. A constant accumulation of product in each microcavity is observed, which enables the calculation of reaction rates by linear regression.

Figure 29:
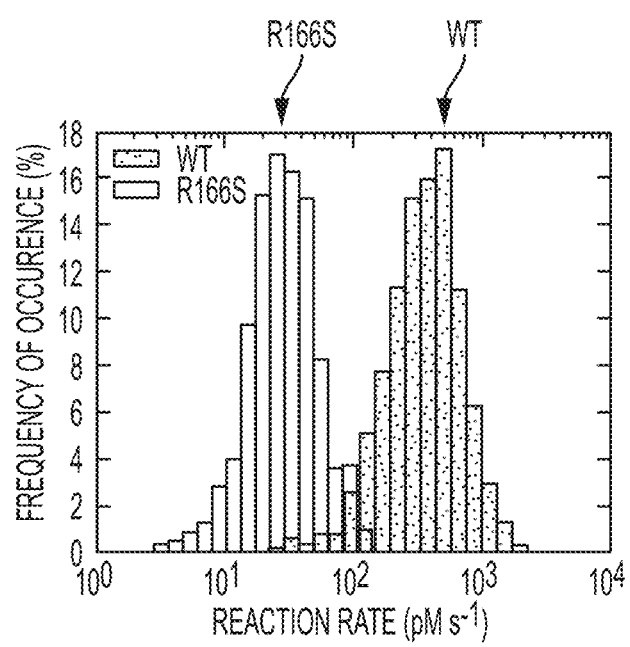
FIG. 29 shows single-cell kinetic profiles of yeast-displayed WT alkaline phosphatase and an R166S point mutant with reduced catalytic efficiency measured according to a method of the disclosure.

Approximately 5,000 single-cell traces for WT alkaline phosphatase and the R166S variant were quantified over the course of 20-min or 3-hr reactions (for WT and R166S, respectively) in the arrays. Histograms of the time course slopes, which define the activity distribution of each mutant in the microcavity array, are shown in FIG. 29. In particular, single-cell kinetic profiles are shown of yeast-displayed WT alkaline phosphatase and an R166S point mutant with reduced catalytic efficiency. Reactions were carried out in 20 µm arrays, with a single yeast cell loaded per microcavity, using 10 µM DDAOP substrate. single cell kinetic Strikingly, despite cell-to-cell variability in enzymatic activity within each clonal population (likely due to heterogeneity in protein expression levels), the µSCALE platform clearly delineates the R166S mutant from the WT enzyme on the basis of reaction kinetics.

Figure 30:
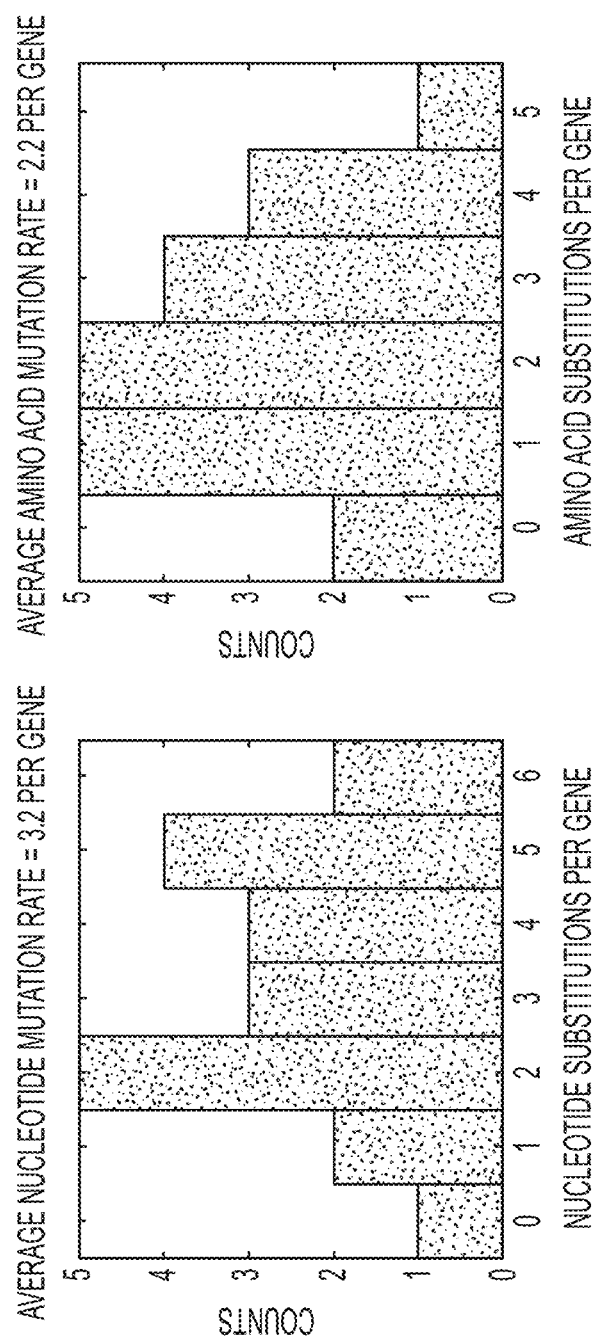
FIG. 30 shows estimated mutation frequency in the alkaline phosphatase error-prone PCR library.
Figure 32:
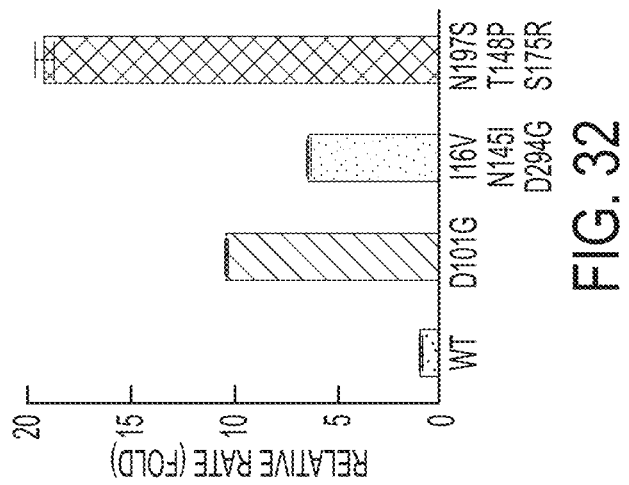
FIG. 32 shows the relative rates of WT enzyme and the three most active variants isolated from the library screens shown in FIG. 31.
Figure 31:
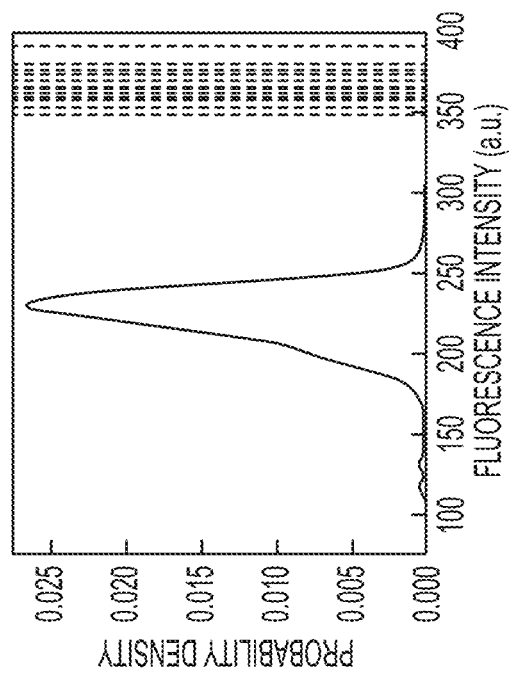
FIG. 31 shows the quantification of a screen of randomly mutated AP library according to methods of the disclosure.
Figure 33:
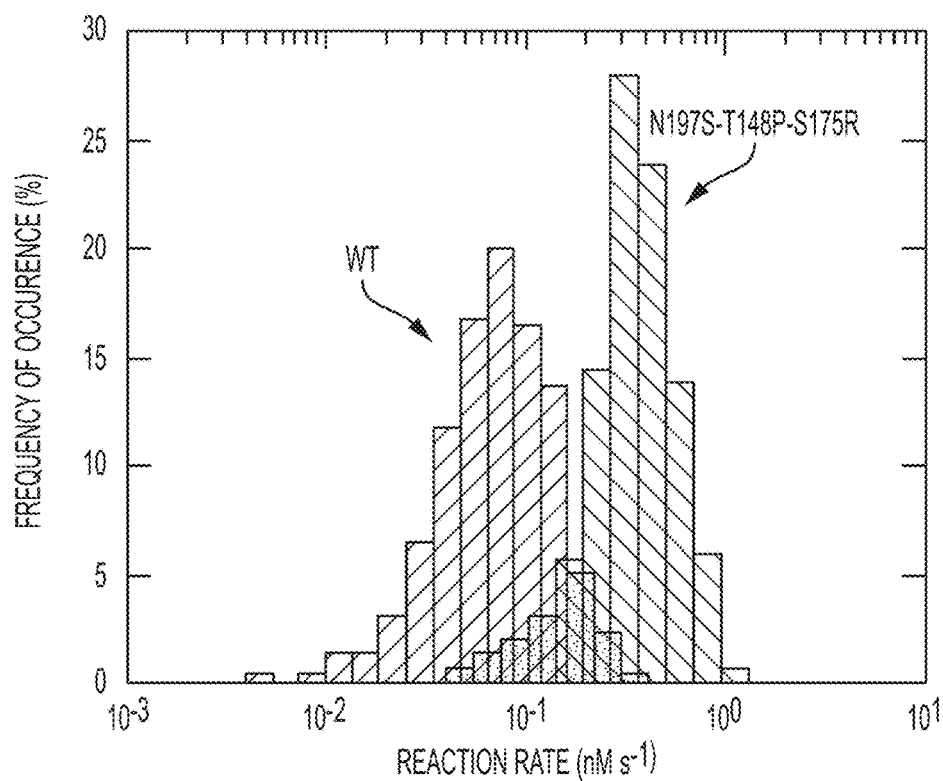
FIG. 33 shows single-cell kinetic profiles of yeast-displayed WT AP and an artificially evolved N197S-T148P-S175R triple mutant.

Next, to demonstrate the ability of µSCALE to identify improved enzyme variants, a randomly mutated alkaline phosphatase library was screened (~$10^7$ transformants, against 1 µM DDAOP (4-fold lower than the apparent $K_M$ for WT alkaline phosphatase) and in the presence of 15 µM inorganic phosphate added to each reaction (4-fold higher than the measured $K_I$ for WT alkaline phosphatase). These conditions put selective pressure on the library to enrich for sequences that increase the enzyme's tolerance to inhibitor, a common objective in many diverse subfields of enzyme engineering (see e.g. Alberstein, M., et al., *Plant J.* 69, 57-69 (2012); Yang, J.-S., et al., *PLoS Comput. Biol.* 8, e1002612 (2012); Hu, X., et al., *Appl. Microbiol. Biotechnol.* 87, 1773-82 (2010)). After transformation and three passages from OD600 of 0.2 to 6, an aliquot of the yeast ePCR library was Zymoprepped and transformed into DH10B *E. coli* cells. Twenty clones were picked and genotyped by Sanger sequencing, yielding the distribution of mutation rates shown in the FIG. 30. Fifteen putative hits with enhanced activity relative to a WT alkaline phosphatase reference under the screening conditions tested were isolated via single-cell extraction, cultured, and rescreened in bulk under the same conditions described above. FIG. 31 shows the quantification of the µSCALE screen of randomly mutated AP library. The peak shows the distribution of observed single-cell enzymatic activity during the screen. The fifteen most active cells at the upper tail of this distribution (shown as dashed vertical lines) were extracted from the array, amplified, and rescreened to further enrich for improved enzyme variants. Three variants were selected for sequencing and more detailed characterization based on their highly significant rate accelerations relative to WT alkaline phosphatase both in bulk biochemical assays. FIG. 32 shows the relative rates of WT enzyme and the three most active variants isolated from µSCALE library screens. Rates were measured with yeast-displayed constructs in bulk biochemical assays under identical conditions to those used in the screen. FIG. 33 shows single-cell kinetic profiles of yeast-displayed WT AP and an artificially evolved N197S-T148P-S175R triple mutant. Reactions were carried out with 5 µM DDAOP in the absence of inorganic phosphate and analyzed on the µSCALE platform using the same procedure employed for the ePCR library screen.

Figure 35:
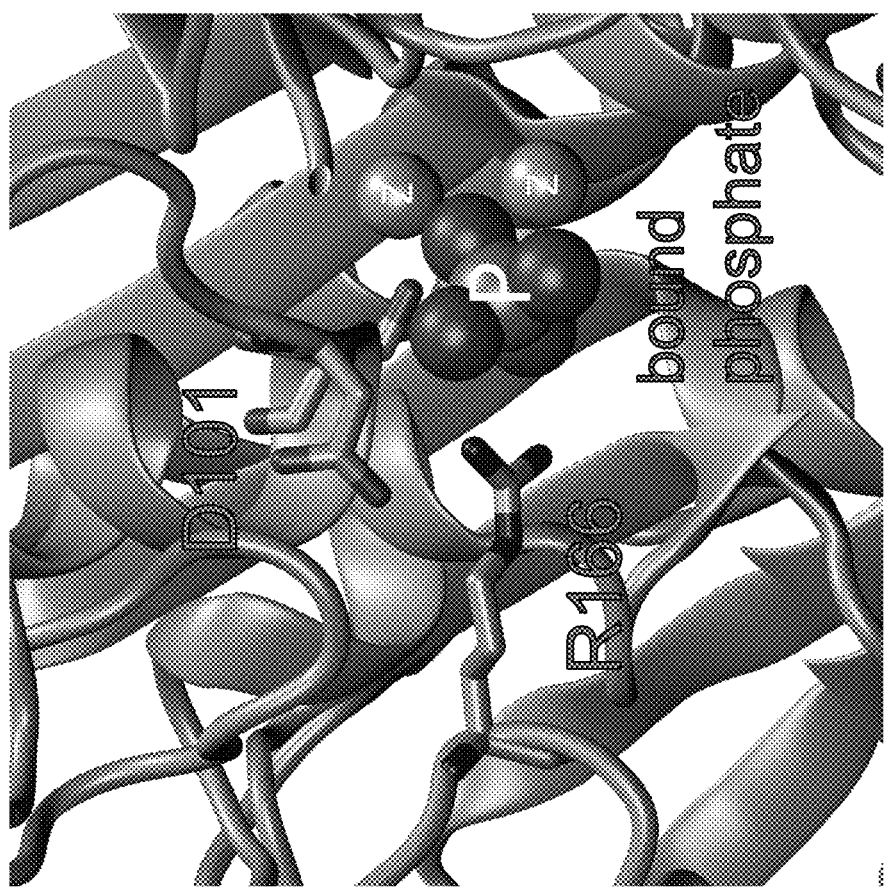
FIG. 35 shows the structural basis for reduced phosphate inhibition in artificially evolved D101G mutant.

The D101 position is known to be important for positioning the R166 residue that coordinates the phosphate ion within the AP active site. As such, the D101G mutation uncovered in our screens likely alters the positioning of R166 that lowers the affinity of the enzyme for inorganic phosphate. FIG. 34 shows phosphate inhibition curves for WT enzyme and the three improved variants isolated from µSCALE screens. One of the three variants exhibited significantly reduced sensitivity to inorganic phosphate, with an apparent $K_I$ that is 10-fold higher than that of the WT enzyme. Reactions were run with substrate concentrations at least 10-fold lower than the apparent $K_m$ of each mutant. Fits to a competitive inhibition model are overlaid above the data as solid lines. In all experiments, error bars correspond to the standard deviation of three independent measurements. FIG. 35 shows the structural basis for reduced phosphate inhibition in artificially evolved D101G mutant. The active site of WT AP (PDB 1ALK) has inorganic phosphate (P) bound. Active site zinc ions are shown (z), D101 and R166 residues are rendered as sticks, and all other protein residues are depicted in ribbon representation.

Figure 36:
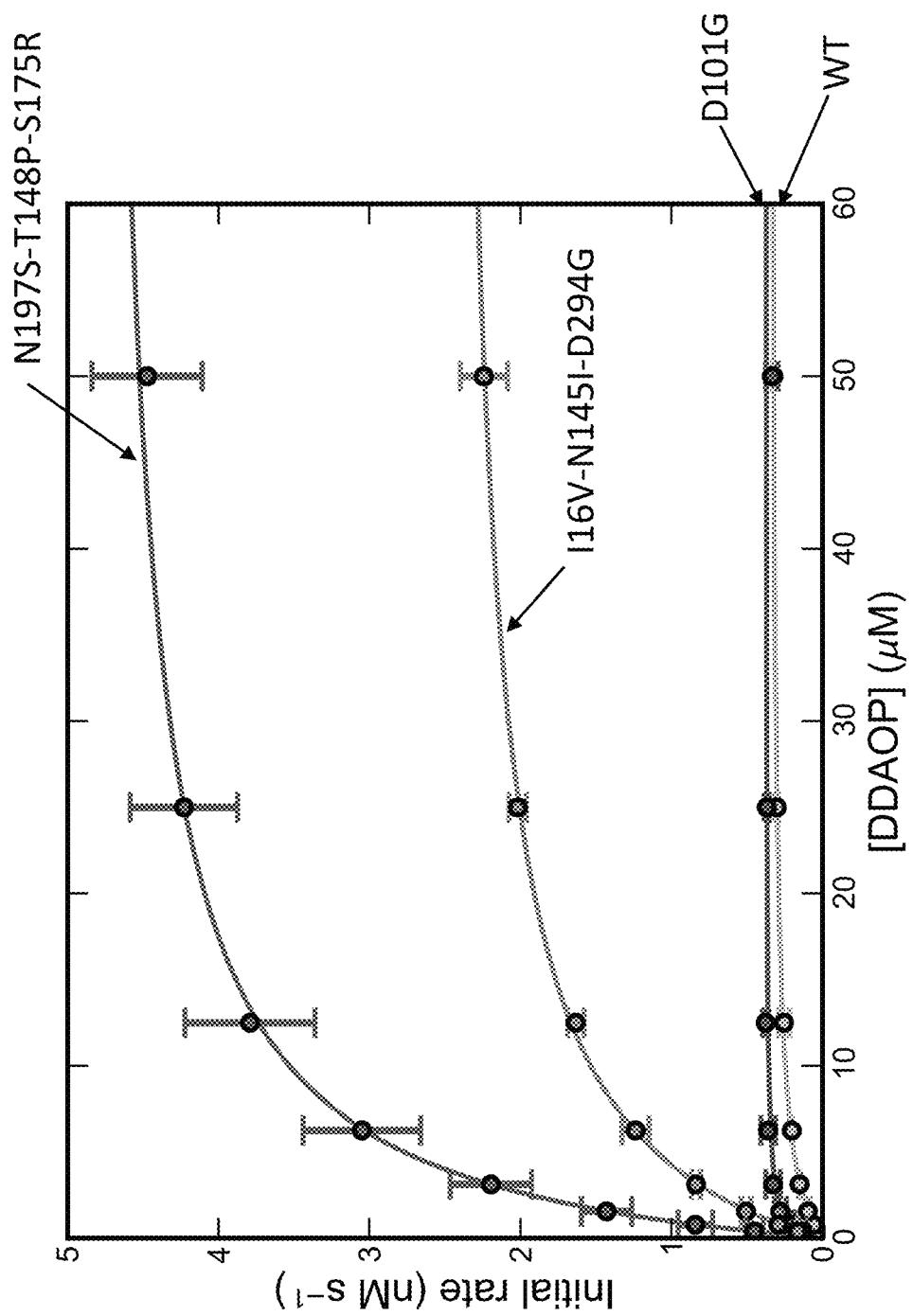
FIG. 36 shows kinetics of yeast-displayed WT AP and three variants isolated from μSCALE screens as a function of DDAOP concentration.
Figure 37:
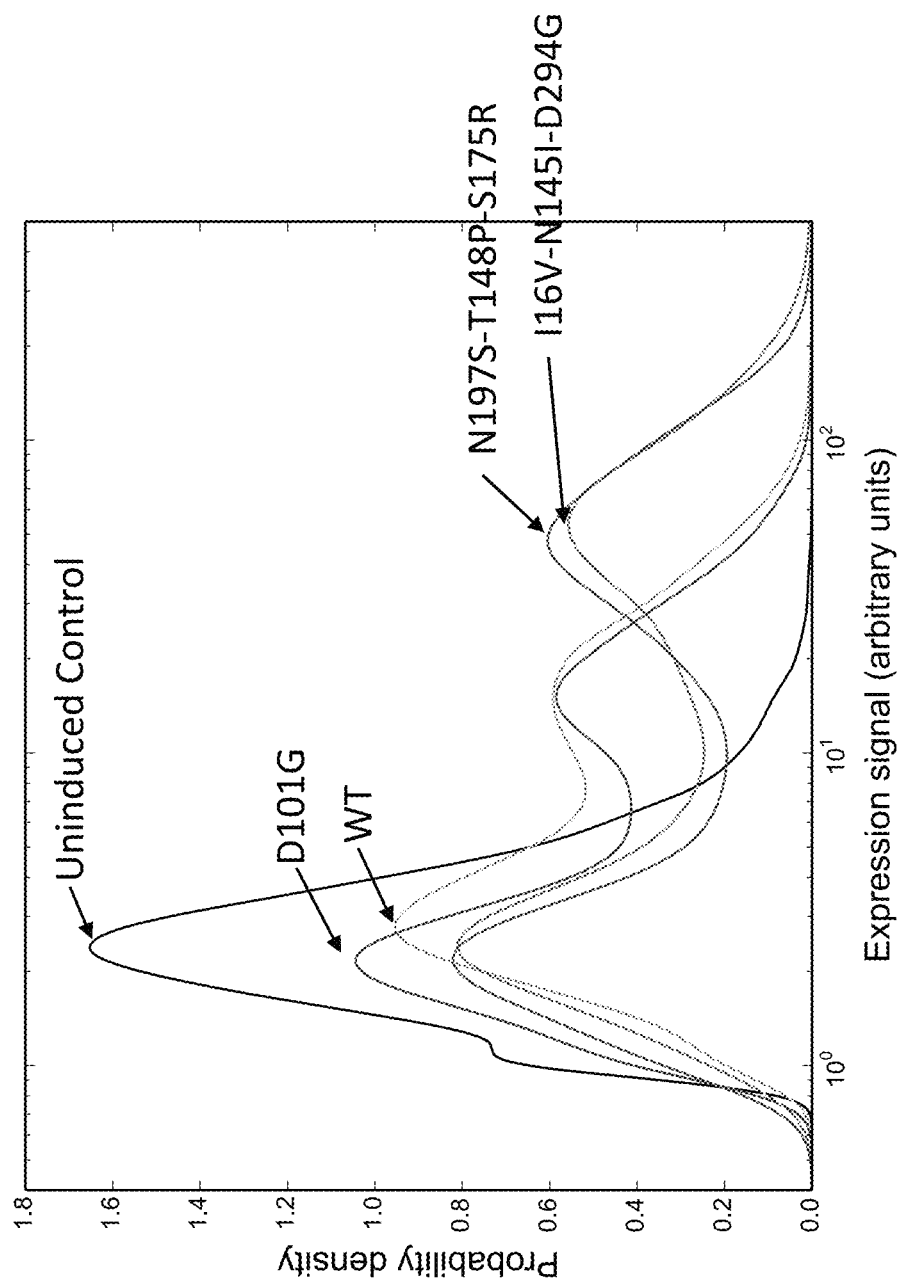
FIG. 37 shows expression profiles of AP mutants displayed on the surface of yeast.
Figure 38:
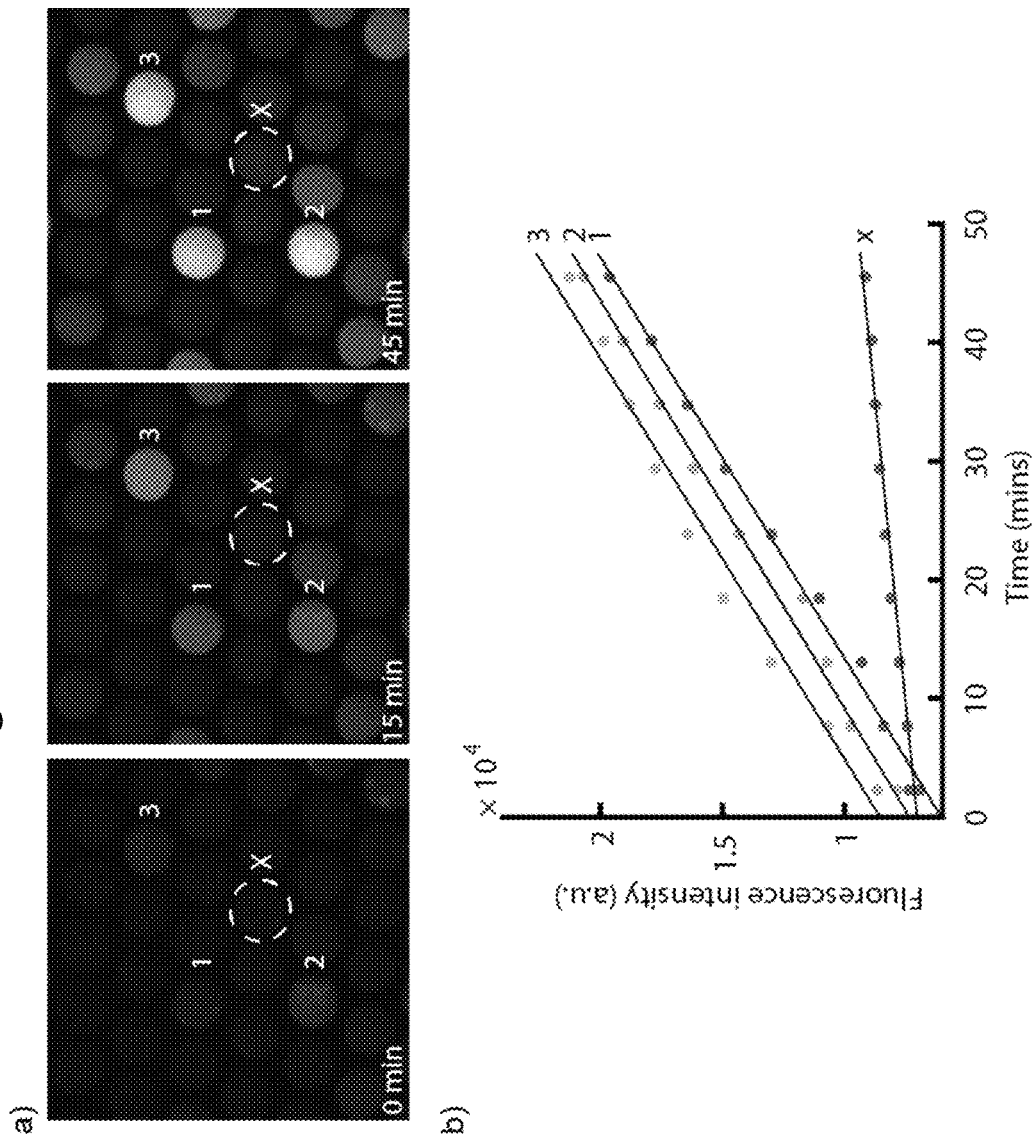
FIG. 38 shows representative images from a time-resolved enzymatic assays and the quantitation of the images according to a method of the disclosure.
Figure 39:
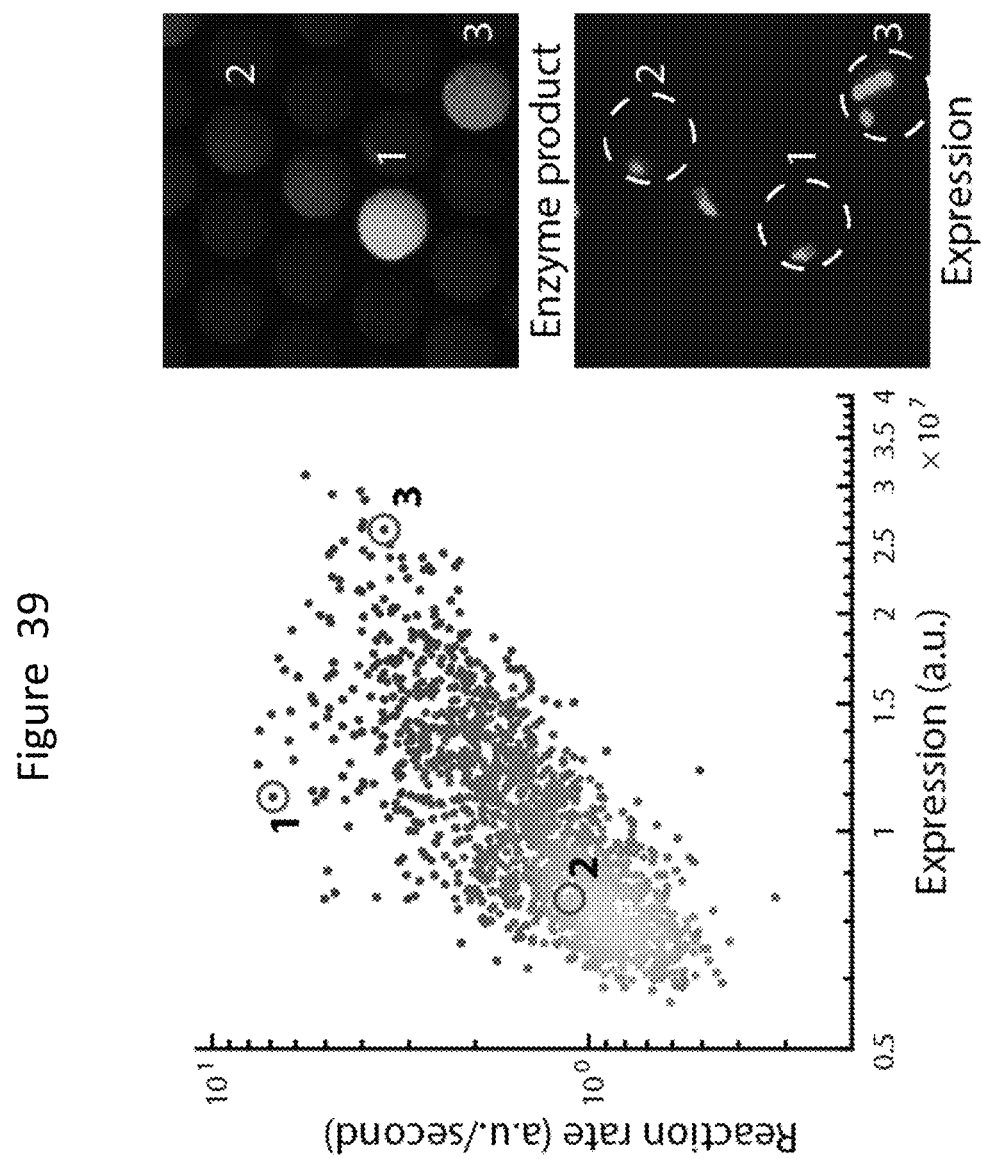
FIG. 39 shows pictures of microcapillaries and the reaction rates of microcavities harboring yeast cells expressing NPP according to an example method of the disclosure.

Improved performance of this D101G mutant relative to the WT enzyme in the presence of phosphate was preserved upon soluble expression and purification from *E. coli* (Table 8). As shown in FIG. 36, the other two variants exhibited higher basal levels of activity than WT alkaline phosphatase, which can be partially explained by enhanced yeast surface expression of these mutants. In FIG. 36, fits to the standard Michaelis-Menten model are overlaid above the data as solid lines. FIG. 37 shows expression profiles of AP mutants displayed on the surface of yeast. Protein display levels were measured via antibody labeling of the C-terminal myc tag fused to each enzyme and quantified using flow cytometry.

Neither variant could be purified in active form from *E. coli*, suggesting that the beneficial mutations acquired by these clones are specific to the yeast surface environment and incompatible with proper folding of the homodimer in solution.

Table 9 shows the measurement of inorganic phosphate contamination in AP reactions using fluorescently labeled phosphate-binding protein from *E. coli*. Fluorescence measurements were converted to phosphate concentrations using the calibration curve in FIG. 23. Errors reflect the standard deviation over two independently prepared samples. Limit of detection for the assay is 10 nM Pi.

TABLE 9

| Sample | [Pi] (nM) |
| --- | --- |
| AP Reaction Buffer | 292 +/− 7 |
| 0.5 µM DDAOP (in Milli-Q H$_2$O) | <10 |
| 5 µM DDAOP (in Milli-Q H$_2$O) | <10 |
| 50 µM DDAOP (in Milli-Q H$_2$O) | <10 |
| 50 pM WT AP (purified) | <10 |

Table 10 shows measurement of inorganic phosphate levels in alkaline phosphatase reactions using fluorescently labeled phosphate-binding protein from *E. coli*. Fluorescence measurements were converted to phosphate concentrations using the calibration curve in FIG. 23 (see Methods). Errors were propagated from uncertainties in the calibration curve using the parametric bootstrap method. Limit of detection for the assay is 10 nM $P_i$.

TABLE 10

| Sample | [$P_i$] |
| --- | --- |
| AP Reaction Buffer | 1.8 ± 0.2 µM |
| 0.2% BSA (in Milli-Q H$_2$O) | 150 ± 10 nM |
| 0.5 µM DDAOP (in Milli-Q H$_2$O) | <10 nM |
| 5 µM DDAOP (in Milli-Q H$_2$O) | <10 nM |
| 50 µM DDAOP (in Milli-Q H$_2$O) | <10 nM |
| 50 pM WT Enzyme (purified) | <10 nM |

Table 11 shows the relative rates of WT AP and the three variants isolated from µSCALE screens in both yeast-displayed and purified enzyme formats. All reactions were conducted using 1 µM DDAOP in the presence of 15 µM added inorganic phosphate. All yeast assays were carried out at a cell density of 3200 cells/μL using freshly transformed cells. Purified enzyme reactions with WT AP and the D101G mutant were carried out using 50 pM enzyme, while reactions with the I16V-N145I-D294G and N197S-T148P-S175R triple mutants were carried out using 50 nM enzyme (with rates scaled accordingly).

TABLE 11

| Mutant | $k_{rel}$ (yeast display) | $k_{rel}$ (purified protein) |
|---|---|---|
| WT | 1.00 +/− 0.07 | 1.00 +/− 0.03 |
| D101G | 10.39 +/− 0.07 | 49 +/− 6 |
| I16V-N145I-D294G | 6.4 +/− 0.1 | 0.0039 +/− 0.0006 |
| N197S-T148P-S175R | 19.2 +/− 0.5 | 0.011 +/− 0.002 |

Table 12 shows metal ion and phosphorous content in WT alkaline phosphatase and the two triple mutants isolated from μSCALE screens, as measured by atomic emission spectroscopy (AES). The expected Zn/Mg/protein stoichiometry for an alkaline phosphatase monomer is 2:1:1.3 In addition, WT alkaline phosphatase expresses with inorganic phosphate bound in the active site in a 1:1 stoichiometry. Deviations from these values in the WT alkaline phosphatase sample presumably reflect errors in sample preparation and determination of protein concentration. The lack of significant metal occupancy in the active sites of the I16V-N145I-D294G and N197S-T148P-S175R triple mutants helps explain the poor activity of these variants. The AES data, along with the crystal structure of WT alkaline phosphatase (PDB 1ALK), support a model in which mutations at N145 and T148 disrupt the folding of the soluble protein and hence its ability to bind the metal cofactors required for efficient catalysis.

TABLE 12

| Mutant | Zn/protein | Mg/protein | P/protein |
|---|---|---|---|
| WT | 2.50 | 0.82 | 0.85 |
| I16V-N145I-D294G | 0.08 | 0.01 | 0.62 |
| N197S-T148P-S175R | 0.08 | 0.01 | 0.10 |

Normalization of Enzyme Activity of Expression

Another well-studied enzyme in the AP superfamily is nucleotide pyrophosphatase/phosphodiesterase (NPP), which catalyzes phosphate diester hydrolysis. As other members of this super family, NPP is a bi-metalloenzyme containing a two $Zn^{2+}$ motif.

NPP are normally found as transmembrane proteins on eukaryotic cell surface, where they act on extracellular phosphate diesters. The NPP was isolated from *X. axonopodis* pv. *citri*, and there is no functional data for this enzyme in its native context. This variant was chosen for its overexpression and in vitro phosphodiesterase activity. This NPP variant is a monomer, which make yeast-surface display facile.

For NPP, catalytic activity was measured using the substrate bis (4-methylumbelliferyl) phosphate (Bis-MUP), which yields two fluorescent 4-methylumbelliferone (MU) upon hydrolysis. Unlike the AP substrate (DDAOP), Bis-MUP is not fluorescent before cleavage, and its product has a narrow fluorescence excitation and emission spectrum. Because of this property, the quantification of the level of yeast-surface protein expression could be determined. By staining the yeast cells with a fluorescently labeled secondary antibody to a C-terminal c-myc, enzyme activity can be normalized with expression, which can reduce the noise of the assay.

In this experiment, a black, hydrogen fired glass array was used. The black glass wall prevented fluorescence crosstalk between the microcavities, eliminating the "halo" effect observed in the clear glass array. Also, the black array enables extraction without the addition of magnetic microbeads. Without the microbeads, the image quality and measurement sensitivity improves dramatically.

Yeast for expression was stained and single-cell reaction time courses were measured for yeast-displayed NPP. After monitoring the reaction over time, the reaction rates of each microcapillary were calculated by linear regression and plotted rate against NPP expression. FIG. 38, panel a) shows pictures depicting the images of the highlighted data (circles). Three microcavities harboring yeast cells displaying active enzyme (white numbers) and a nearby empty capillary (dotted circle) are shown for comparison. FIG. 38, panel b), also shows quantification of the images. FIG. 39 depicts reaction rates of each microcavity harboring yeast cells expressing NPP calculated by linear regression and plotted against c-Myc tag expression. Pictures depict the images of the highlighted data (circles).

Example 6

Extraction and Growth of Cells on Culture Matrix

Yeast cells cultured in the array were extracted directly onto a culture matrix or a capture surface. The cells captured on the surface were transferred to a culture matrix or a culture media. Viability of the cells was measured.

Materials:

SD-CAA Media 10 g Dextrose 3.35 g Nitrogen base without amino acids 2.5 g Casamino acids 2.7 g Na2HPO4 anhydrous 4.28 g NaH2PO4*H2O In 500 mL of $H_2O$ SD-CAA Agar Plates 91 g Sorbitol 7.5 g Agar 3.35 g Nitrogen base without amino acids 2.5 g Casamino acids 2.7 g Na2HPO4 anhydrous 4.28 g NaH2PO4*H2O In 500 mL of $H_2O$ SG-CAA Media 10 g Galactose 3.35 g Nitrogen base without amino acids 2.5 g Casamino acids 2.7 g Na2HPO4 anhydrous 4.28 g NaH2PO4*H2O In 500 mL of $H_2O$ Yeast growth and protein induction: *Saccharomyces cerevisiae* yeast with the PCT-Con2 plasmid is cultured in SD-CAA cultures and grown 24 hours at 30° C. to OD600=3-6. The cells are centrifuged and resuspended in SG-CAA for a final OD600=1. The cells are then grown for an additional 24 hours to a final OD600=7. Growth in the SG-CAA induces the PCT-Con2 to express protein on the yeast cell surface.

Yeast staining and loading: To improve visibility, the induced yeast is stained with fluorescent antibodies targeted at the c-Myc tag which is displayed at the yeast surface via the PCT-Con2 plasmid. The yeast are incubated for 30 minute with an anti-cMyc antibody and then another 30 minutes with an secondary antibody for anti-cMyc antibody tagged with ALEXAFLUOR® 555 dye. After labeling, the yeast cells are diluted to a calculated concentration to result in single cell per core (3200 cells/uL for the 20 um pore array) and spread over the micropore array.

Capture surface preparation and extraction: To prepare the capture surface, 20 uL of hydration fluid (glycerol) is spread uniformly over a 18 mm by 24 mm glass cover slip. This coverslip is then positioned approximately 1 mm under pore array.

With the appropriate laser intensity, a selected pore is extracted directly onto a culture matrix or the capture surface. The cells were then cultured for 2 days or until colonies form.

Figure 40:
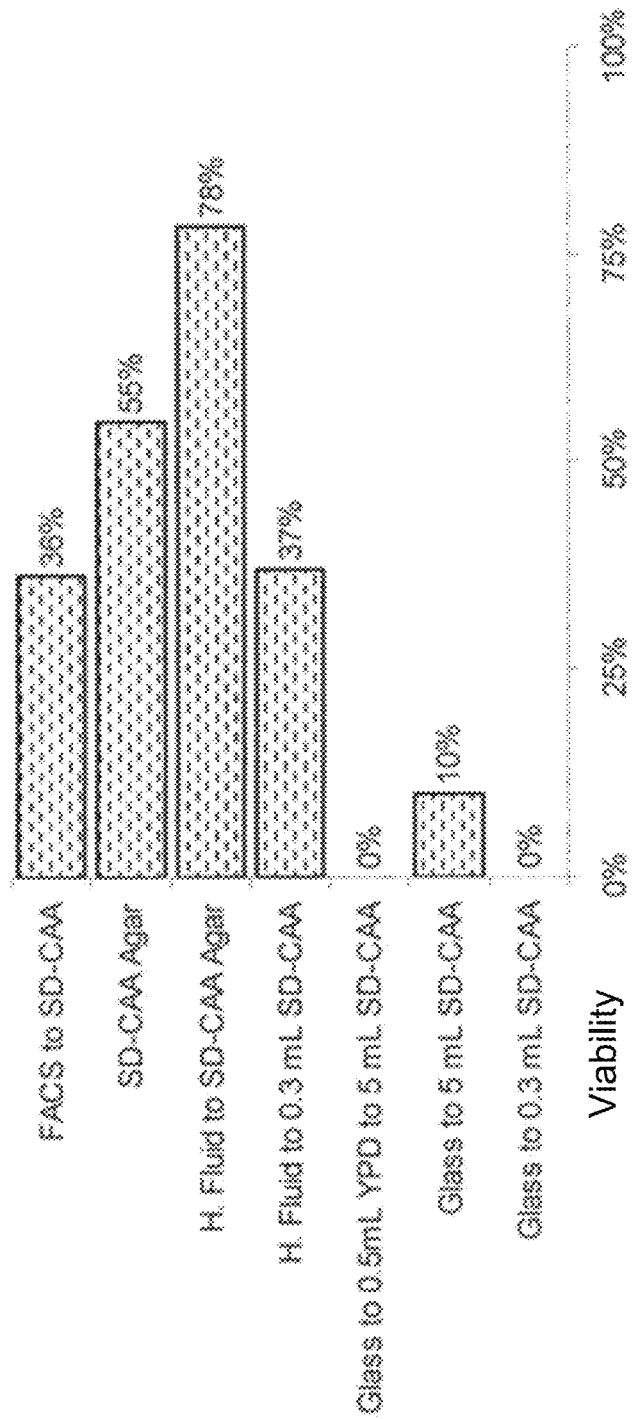
FIG. 40 shows the results of a cell viability experiment in accordance with a method of the disclosure.

FIG. 40 shows a bar chart with all the results of the different types of single cell extraction configurations tested: (1) FACS to SD-CAA shows the results of the cells sorted by FACS directly into the SD-CAA culture media in a 96 well plate (one cell per well); (2) SD-CAA Agar is the result of cells extracted directly from the array on to an agar coated capture surface; (3) H. Fluid to SD-CAA Agar is the results of cells extracted onto a capture surface coated with an hydration fluid (glycerol) and inverted onto an agar SD-CAA agar matrix; (4) H. Fluid to 0.3 mL SD-CAA shows the results of cells extracted onto a capture surface (with hydration fluid) and then transferred directly into the SD-CAA media; (5) Glass to 0.5 mL YPD to 5 mL SD CAA shows the results of cells captured on a uncoated glass capture surface, transferred to YPD media (Sigma-Aldrich) and then the media transferred to a SD-CAA media; (6) Glass to 5 mL SD-CAA shows the results of cell captured on an uncoated glass surface transferred directly into 5 mL SD-CAA media; (7) Glass to 0.3 mL SD-CAA shows the results of cell captured on an uncoated glass surface transferred directly into 0.3 mL SD-CAA media. The highest single cell viability comes from the combination of extracting the cell onto a coated capture surface and placing the transferring the cells onto agar with SD-CAA media immediately after.

Although preferred embodiments of the disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

What is claimed is:

1. A method for screening a library of cells having a plurality of genotypes for a cell having a phenotype of interest for producing a molecule of interest, the method comprising
   (a) loading a microcavity array with the library of cells;
   (b) incubating the array under conditions that allow for production of the molecule of interest;
   (c) imaging the array to identify a cavity comprising cells having the phenotype of interest; and
   (d) extracting the contents of the cavity comprising cells having the phenotype of interest by directing electromagnetic radiation from a pulsed diode laser that delivers electromagnetic radiation in 2-20 pulses having pulse length of 1-10milliseconds with a pulse separation of 10 to 100 millisecond at a radiation absorbing material associated with the cavity.

2. The method of claim 1, wherein the directing of electromagnetic radiation comprising applying the electromagnetic radiation to the radiation absorbing material to avoid heating a sample liquid in the cavity that is not in contact with the material.

3. The method of claim 1, wherein the cells are expanded in the array.

4. The method of claim 1, wherein the cells are selected from the group consisting of a mammalian cell, a yeast cell, and a bacterial cell.

5. The method of claim 4, wherein the molecule of interest is displayed on the surface of a yeast cell or a bacterial cell.

6. The method of claim 4, wherein the molecule of interest is secreted by a yeast cell or a bacterial cell.

7. The method of claim 1, further comprising culturing the extracted contents of the cavities to produce a second-generation library of cells and repeating steps (a)-(d) with the second generation library.

8. The method of claim 1, further comprising (1) extracting DNA from the cells comprising a gene for the phenotype of interest, (2) amplifying the DNA under conditions to introduce mutations in the gene; (3) creating a second generation library of cells comprising the amplified DNA, and (4) repeating steps (a)-(d) with the second generation library.

9. The method of claim 1, wherein the phenotype of interest comprises a cell producing a binding agent.

10. The method of claim 9, wherein the binding agent is a cell surface binding agent, an antibody, an antibody fragment, a ligand, a small molecule or a receptor.

11. The method of claim 1, wherein the molecule of interest comprises a fluorescent protein that has at least one of an emission intensity of interest and an emission spectra of interest.

12. The method of claim 11, wherein the scanning comprises identifying cavities emitting the at least one of the emission intensity of interest and the emission spectra of interest.

13. The method of claim 1, wherein the phenotype of interest is a protein having an enzymatic activity, a protein having a lack of inhibition of enzyme activity, and a protein having activity in the presence of an inhibitor for the enzyme.

14. A method for engineering a property of interest in a fluorescent protein, wherein the property of interest comprises at least one of an emission spectra, an emission intensity, a stokes shift, and an absorption spectra, the method comprising creating a library of cells producing a mutant form of a fluorescent protein, and screening the library for cells producing the mutant form having the property of interest, wherein the screening method comprises:
(a) loading a microcavity array with the library of cells;
(b) incubating the array under conditions that allow for production of the mutant form;
(c) imaging the array to identify a cavity comprising cells producing the mutant form; and
(d) extracting the contents of the cavity comprising cells producing the mutant form by directing electromagnetic radiation from a pulsed diode laser that delivers electromagnetic radiation in 2-20 pulses having pulse length of 1-10milliseconds with a pulse separation of 10 to 100 millisecond at a radiation absorbing material associated with the cavity.

15. A method for measuring enzyme kinetics for a member of a protein enzyme library produced by a library of cells having a plurality of genotypes for producing mutant forms of a protein enzyme; the method comprising
(a) loading a microcavity array with the library of cells;
(b) incubating the array in the presence of a substrate for the protein enzyme under conditions that allow for production of the enzyme of interest;
(c) imaging the array at selected intervals;
(d) measuring difference in enzyme activity for one or more cavities of the array;
(e) extracting the contents of a cavity comprising cells having the phenotype of interest by directing electromagnetic radiation from a pulsed diode laser that delivers electromagnetic radiation in 2-20 pulses having pulse length of 1-10milliseconds with a pulse separation of 10 to 100 millisecond at a radiation absorbing material associated with the cavity.

16. The method of claim 15, wherein the library of cells is a library of yeast cells or library of bacterial cells.

17. The method of claim 16, wherein the protein enzymes are displayed on the surface of the cells.

18. The method of claim 16, wherein the protein enzymes are secreted by the cells.

19. The method of claim 15, further comprising adding an inhibitor for the enzyme.

* * * * *

SEQUENCE LISTING

```
<160> NUMBER OF SEQ ID NOS: 2

<210> SEQ ID NO 1
<211> LENGTH: 224
<212> TYPE: PRT
<213> ORGANISM: Artificial Sequence
<220> FEATURE:
<223> OTHER INFORMATION: ddOFP

<400> SEQUENCE: 1

Val Ile Lys Glu Phe Met Arg Phe Lys Val Arg Leu Glu Gly Ser Met
1               5                   10                  15

Asn Gly His Glu Phe Glu Ile Glu Gly Glu Gly Glu Gly Arg Pro Tyr
            20                  25                  30

Glu Gly Thr Gln Thr Ala Lys Leu Lys Val Thr Lys Gly Gly Pro Leu
        35                  40                  45

Pro Phe Ala Trp Asp Ile Leu Ser Pro Gln Ile Thr Tyr Gly Ser Lys
    50                  55                  60

Ala Tyr Val Lys His Pro Ala Asp Val Pro Asp Tyr Met Lys Leu Ser
65                  70                  75                  80

Phe Pro Glu Gly Phe Lys Trp Glu Arg Val Met His Phe Glu Asp Gly
                85                  90                  95

Gly Leu Val Thr Val Thr Gln Asp Thr Ser Leu Gln Asp Gly Thr Leu
            100                 105                 110

Ile Tyr Lys Val Lys Met Arg Gly Thr Asn Phe Pro Pro Asp Gly Pro
        115                 120                 125

Val Met Gln Arg Lys Thr Leu Gly Trp Asp Tyr Ser Thr Glu Arg Leu
    130                 135                 140

Tyr Pro Glu Asn Gly Val Leu Lys Gly Glu Leu Leu Gly Arg Leu Lys
145                 150                 155                 160

Leu Lys Asp Gly Gly Leu Tyr Leu Val Glu Phe Lys Thr Ile Tyr Met
                165                 170                 175
```

```
Ala Lys Lys Pro Val Gln Leu Pro Gly Tyr Tyr Phe Val Asp Thr Lys
            180                 185                 190

Leu Asp Ile Thr Ser His Asn Glu Asp Tyr Thr Ile Val Glu Gln Tyr
            195                 200                 205

Glu Arg Ser Glu Gly Arg His His Leu Gly Met Asp Glu Leu Tyr Lys
            210                 215                 220

<210> SEQ ID NO 2
<211> LENGTH: 231
<212> TYPE: PRT
<213> ORGANISM: Artificial Sequence
<220> FEATURE:
<223> OTHER INFORMATION: ddRFP

<400> SEQUENCE: 2

Met Val Ser Lys Ser Glu Glu Val Ile Lys Glu Phe Met Arg Phe Lys
1               5                   10                  15

Val Arg Leu Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
            35                  40                  45

Val Thr Lys Gly Gly Pro Leu Pro Phe Ala Trp Asp Ile Leu Ser Pro
        50                  55                  60

Gln Ile Met Tyr Gly Ser Lys Ala Tyr Val Lys His Pro Ala Asp Val
65                  70                  75                  80

Pro Asp Tyr Met Lys Leu Ser Phe Pro Glu Gly Phe Lys Trp Glu Arg
                85                  90                  95

Val Met His Phe Glu Asp Gly Gly Leu Val Thr Val Thr Gln Asp Thr
            100                 105                 110

Ser Leu Gln Asp Gly Thr Leu Ile Tyr Lys Val Lys Met Arg Gly Thr
            115                 120                 125

Asn Phe Pro Pro Asp Gly Pro Val Met Gln Lys Lys Thr Leu Gly Trp
            130                 135                 140

Asp Tyr Ala Thr Glu Arg Leu Tyr Pro Glu Asp Gly Val Leu Lys Gly
145                 150                 155                 160

Glu Leu Leu Gly Arg Leu Lys Leu Lys Asp Gly Gly Leu Asn Leu Val
                165                 170                 175

Glu Phe Lys Thr Ile Tyr Met Ala Lys Lys Pro Val Gln Leu Pro Gly
            180                 185                 190

Tyr Tyr Phe Val Asp Thr Lys Leu Gly Ile Thr Ser His Asn Glu Asp
            195                 200                 205

Tyr Thr Ile Val Glu Gln Tyr Glu Arg Ser Glu Gly Arg His His Leu
        210                 215                 220

Gly Met Asp Glu Leu Tyr Lys
225                 230
```